United States Patent
Grimm et al.

(10) Patent No.: US 6,552,168 B1
(45) Date of Patent: Apr. 22, 2003

(54) GAMMA-KETOACID TETRAPEPTIDES AS INHIBITORS OF CASPASE-3

(75) Inventors: Erich L. Grimm, Quebec (CA); Johanne Renaud, Base (CH); Renee Aspiotis, Quebec (CA); Christopher I. Bayly, Quebec (CA); Robert Zamboni, Quebec (CA); Shawn Black, Ivoryton, CT (US)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/453,201

(22) Filed: Dec. 2, 1999

Related U.S. Application Data

(60) Provisional application No. 60/110,567, filed on Dec. 2, 1998.

(51) Int. Cl.[7] .................................................. C07K 5/08
(52) U.S. Cl. .......................... 530/331; 530/330; 514/18
(58) Field of Search ................................. 530/331, 330; 514/18

(56) References Cited

U.S. PATENT DOCUMENTS

| | | | |
|---|---|---|---|
| 5,498,616 A | 3/1996 | Mallamo et al. ............ 514/300 |
| 5,565,429 A | 10/1996 | Vincent et al. ............... 514/18 |
| 5,610,297 A | 3/1997 | Power ........................ 544/168 |
| 5,716,929 A | 2/1998 | Golec et al. .................. 514/18 |

FOREIGN PATENT DOCUMENTS

| | | |
|---|---|---|
| EP | 0 393 457 B1 | 4/1990 |
| EP | 0 393 457 | 4/1990 |
| EP | 0 519 748 A3 | 6/1992 |
| EP | 0 519 748 B1 | 6/1992 |
| EP | 0 519 748 A2 | 12/1992 |
| WO | 96/16080 | 5/1996 |
| WO | 98/49190 | 11/1998 |

OTHER PUBLICATIONS

Mjalli, E. A.—Bioorganic and Medicinal Chemistry Letters, vol. 3, No. 12, pp. 2689–2692, 1993.
Nicholson, D. W., et al.—Nature, vol. 376, No. 6335, pp. 37–43, 1995.
Nicholson, E. A.—Tibs Trends in Biochemical Science, vol. 22, pp. 299–306, 1997.
Brady, E. A.—Biochemistry, vol. 37, pp. 8508–8515, 1998.

*Primary Examiner*—Christopher S. F. Low
*Assistant Examiner*—David Lukton
(74) *Attorney, Agent, or Firm*—Raynard Yuro; David L. Rose

(57) ABSTRACT

The invention encompasses the novel class of compounds represented by formula I, which are caspase-3 inhibitors.

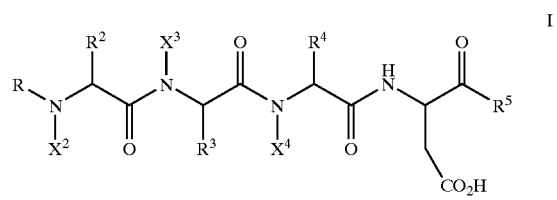

The invention also encompasses certain pharmaceutical compositions for treatment of caspase-3 mediated diseases comprising compounds of formula I.

26 Claims, No Drawings

GAMMA-KETOACID TETRAPEPTIDES AS INHIBITORS OF CASPASE-3

CROSS REFERENCE TO RELATED APPLICATIONS

This application is a non-provisional application related to U.S. Application Serial No. 60/110,567, filed on Dec. 2, 1998 priority of which is claimed hereunder.

BACKGROUND OF THE INVENTION

Apoptotic cell suicide is a fundamentally important biological process that is required to maintain the integrity and homeostasis of multicellular organisms. Inappropriate apoptosis, however, underlies the etiology of many of the most intractable of human diseases. In only the last few years, many of the molecules that participate in a conserved biochemical pathway that mediates the highly ordered process of apoptotic cell suicide have been identified. At the heart of this pathway are a family of cysteine proteases, the 'caspases', that are related to mammalian interleukin-1β converting enzyme (ICE/caspase-1) and to CED-3, the product of a gene that is necessary for apoptotic suicide in the nematode *C. elegans* (Nicholson et al., 1997, Trends Biochem Sci 22:299–306). The role of these proteases in cell suicide is to disable critical homeostatic and repair processes as well as to cleave key structural components, resulting in the systematic and orderly disassembly of the dying cell.

The central importance of caspases in these processes has been demonstrated with both macromolecular and peptide-based inhibitors (which prevent apoptosis from occurring in vitro and in vivo) as well as by genetic approaches. Inhibition of apoptosis via attenuation of caspase activity should therefore be useful in the treatment of human diseases where inappropriate apoptosis is prominent or contributes to disease pathogenesis. Caspase inhibitors would thus be useful for the treatment of human diseases including, but not limited to, acute disorders such as cardiac and cerebral ischemia/reperfusion injury (e.g. stroke), spinal cord injury and organ damage during transplantation, as well as chronic disorders such as neurodegenerative diseases (e.g. Alzheimer's, polyglutamine-repeat disorders, Down's, spinal muscular atrophy, multiple sclerosis), immunodeficiency (e.g. HIV), diabetes, alopecia and aging.

Ten caspases have so far been identified in human cells. Each is synthesized as a catalytically dormant proenzyme containing an amino-terminal prodomain followed by the large and small subunits of the heterodimeric active enzyme. The subunits are excised from the proenzyme by cleavage at Asp-X junctions (Nicholson et al., 1997, Trends Biochem Sci 22:299–306). The strict requirement by caspases for Asp in the $P_1$ position of substrates is consistent with a mechanism whereby proenzyme maturation can be either autocatalytic or performed by other caspases. The three dimensional crystal structures of mature caspase-1 and -3 show that the large subunit contains the principle components of the catalytic machinery, including the active site Cys residue which is harbored within the conserved pentapeptide motif, QACxG,[1] and residues that stabilize the oxyanion of the tetrahedral transition state (Wilson et al., 1994, Nature 370:270–75; Walker et al., 1994, Cell 78:342–52; Rotonda et al., 1996, Nat Struct Biol 3:619–25). Both subunits contribute residues which stabilize the $P_1$ Asp of substrates while the small subunit appears to contain most of the determinants that dictate substrate specificity and, in particular, those which form the specificity-determining $S_4$ subsite. One distinctive feature of these proteases is the absolute requirement for an aspartic acid residue in the substrate $P_1$ position. The carboxylate side chain of the substrate $P_1$ Asp is tethered by four residues in caspase-1 ($Arg^{179}$, $Gln^{238}$ from p20 and $Arg^{341}$, $Ser^{347}$ from p10) that are absolutely conserved in all caspase family members. Catalysis involves a typical cysteine protease mechanism involving a catalytic dyad, composed of $His^{237}$ and $Cys^{285}$ (contained within an absolutely conserved QACxG pentapeptide) and an 'oxyanion hole' involving $Gly^{238}$ and $Cys^{285}$. Inhibitors bind, however, in an unexpected non-transition state configuration (which raises important considerations for inhibitor design) with the oxyanion of the thiohemiacetal being stabilized by the active site $His^{237}$.

Members of the caspase family can be divided into three functional subgroups based on their substrate specificities which have been defined by a positional-scanning combinatorial substrate approach. The principle effectors of apoptosis (group II caspases, which include caspases-2, -3 and -7 as well as *C. elegans* CED-3) have specificity for $[P_4]$DExD$[P_1]$, a motif found at the cleavage site of most proteins known to be cleaved during apoptosis. On the other hand, the specificity of group III caspases (caspases-6, -8, -9 and -10, as well as CTL-derived granzyme B) is $[P_4](I,V,L)ExD[P_1]$ which corresponds to the activation site at the junction between the large and small subunits of other caspase proenzymes including group II (effector) family members. This and other evidence indicates that group III caspases function as upstream activators of group II caspases in a proteolytic cascade that amplifies the death signal. The role of group I caspases (caspases-1, -4 and -5) appears to be to mediate cytokine maturation and their role in apoptosis, if any, has not been substantiated.

A tetrapeptide corresponding to the substrate $P_4$-$P_1$ residues is sufficient for specific recognition by caspases and as a consequence has formed the basis for inhibitor design. In addition to the requirement for a $P_1$ Asp, the $P_4$ residue in particular appears to be most important for substrate recognition and specificity. Caspase-1, for example, prefers a hydrophobic residue such as Tyr in $P_4$ (which corresponds to its YVHD cleavage site within proIL-1β) whereas caspase-3 (and other group II enzymes) has a preference for an anionic Asp residue (which corresponds to the DXXD cleavage sites within most polypeptides that are cleaved by these enzymes during apoptosis). Peptide aldehydes, nitriles and ketones are potent reversible inhibitors of these proteases while compounds that form thiomethylketone adducts with the active site cysteine (e.g. peptide (acyloxy)methylketones) are potent irreversible inhibitors. For example, the tetrapeptide aldehyde Ac-YVAD-CHO (SEQ ID NO: 24) (which was designed to mimic the YVHD caspase-1 recognition sequence within proIL-1β) is a potent inhibitor of caspase-1 ($K_i$<1 nM) but a poor inhibitor of caspase-3 ($K_i$=12 μM) (Thornberry et al., 1992, Nature 356:768–74). In contrast, the Ac-DEVD-CHO (SEQ ID NO: 25) tetrapeptide aldehyde (which was designed to mimic the caspase-3 recognition site) is a very potent inhibitor of caspase-3 ($K_i$<1 nM) although it is also a weaker but reasonable inhibitor of caspase-1, presumably owing to promiscuity in the $S_4$ subsite of this enzyme (Nicholson et al., 1995, Nature 376:37–43).

Several features plague these peptide-derived inhibitors as a platform for drug design. In addition to their metabolic instability and membrane impermeability, the slow-binding time-dependent inhibition of activity (e.g. $k_{on}$ caspase-1:Ac-YVAD-CHO (SEQ ID NO: 24)=3.8×10$^5$ M$^{-1}$s$^{-1}$; $k_{on}$ caspase-3:Ac-DEVD-CHO (SEQ ID NO: 25)=1.3×10$^5$ M$^{-1}$s$^{-1}$) precludes them from the rapid inhibition characteristics that may be necessary to abolish enzymatic activity in vivo. The present patent application describes the resolution of this issue with the discovery of several novel ketones that make highly suitable caspase inhibitors.

SUMMARY OF THE INVENTION

The invention encompasses the novel class of compounds represented by formula I:

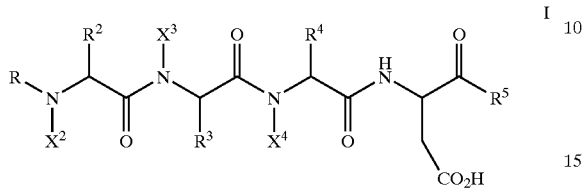

or a pharmaceutically acceptable salt thereof, wherein:
R is selected from the group consisting of:
  (a) H and
  (b) $C(O)R^1$;
$R^1$ is selected from the group consisting of:
  (a) hydrogen,
  (b) $C_{1-6}$alkoxy,
  (c) $NR^6R^7$,
  (d) benzyloxy or mono- or disubstituted benzyloxy, wherein the substituent is selected from the group consisting of:
    (1) methyl,
    (2) halogen,
    (3) methoxy and
    (4) cyano,
  (e) $C_{1-6}$alkyl or substituted $C_{1-6}$alkyl, wherein the substituent is selected from the group consisting of:
    (1) hydroxy,
    (2) halo,
    (3) $C_{1-3}$alkoxy,
    (4) $C_{1-3}$alkylthio,
    (5) phenyl $C_{1-3}$alkoxy,
    (6) phenyl $C_{1-3}$alkylthio,
    (7) phenylcarboxy and
    (8) carboxy,
  (f) aryl or aryl$C_{1-6}$alkyl wherein the aryl group is selected from the group consisting of:
    (1) phenyl,
    (2) naphthyl,
    (3) pyridyl,
    (4) furyl,
    (5) thienyl,
    (6) thiazolyl,
    (7) isothiazolyl,
    (8) imidazolyl,
    (9) benzimidazolyl,
    (10) pyrazinyl,
    (11) pyrimidyl,
    (12) quinolyl,
    (13) isoquinolyl,
    (14) benzofuryl,
    (15) benzothienyl,
    (16) pyrazolyl,
    (17) indolyl,
    (18) purinyl,
    (19) isoxazolyl and
    (20) oxazolyl, and
  (g) mono and di-substituted aryl as defined above in items (1) to (20) of (f), wherein the substituents are independently selected from:
    (1) halo,
    (2) amino,
    (3) nitro,
    (4) hydroxy,
    (5) cyano,
    (6) carboxy,
    (7) formyl,
    (8) amino carbonyl,
    (9) $C_{1-6}$alkyl,
    (10) $C_{1-6}$fluoroalkyl,
    (11) $C_{1-6}$alkylcarbonyl,
    (12) $C_{1-6}$alkoxycarbonyl,
    (13) $C_{1-6}$alkoxy,
    (14) $C_{1-6}$alkylthio,
    (15) $C_{1-6}$alkylsulfonyl and
    (16) deuterio;
$R^2$ is selected from the group consisting of:
  (a) H,
  (b) $CH_3$,
  (c) $CH(CH_3)_2$,
  (d) $CH_2CH(CH_3)_2$,
  (e) $CH_2Ph$,
  (f) $CH_2PhOH$,
  (g) $CH_2OH$,
  (h) $CH_2SH$,
  (i) $CH_2CH_2SCH_3$,
  (j) $CH(CH_3)CH_2CH_3$,
  (k) $CH(CH_3)OH$,
  (l) $CH_2COOH$,
  (m) $CH_2CH_2COOH$,
  (n) $CH_2CH_2CH_2NHCNH(NH_2)$,
  (o) $CH_2CH_2CH_2CH_2NH_2$,
  (p) $CH_2C(O)NH_2$,
  (q) $CH_2CH_2C(O)NH_2$,
  (r) $CH_2CO_2C_{1-4}$alkyl,
  (s) $CH_2SC_{1-4}$alkyl,
  (t) $CH_2S(O)_2C_{1-4}$alkyl,

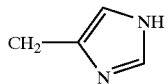 (u)

and

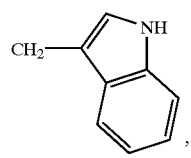 (v)

or $R^2$ and $X^2$ together form a saturated monocyclic ring having the following structure:

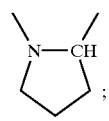

$R^3$ is selected from the group consisting of:
  (a) H,
  (b) $CH_3$,
  (c) $CH(CH_3)_2$,
  (d) $CH_2CH(CH_3)_2$,
  (e) $CH_2Ph$,
  (f) $CH_2PhOH$, (g) $CH_2OH$,
(h) $CH_2SH$,
(i) $CH_2CH_2SCH_3$,
(j) $CH(CH_3)CH_2CH_3$,
(k) $CH(CH_3)OH$,
(l) $CH_2COOH$,
(m) $CH_2CH_2COOH$,
(n) $CH_2CH_2CH_2NHCNH(NH_2)$,
(o) $CH_2CH_2CH_2CH_2NH_2$,
(p) $CH_2C(O)NH_2$,
(q) $CH_2CH_2C(O)NH_2$,
(r) $CH_2CH_2CO_2C_{1-4}$alkyl,
(s) $CH_2CH_2S(O)_2C_{1-4}$alkyl, (t)

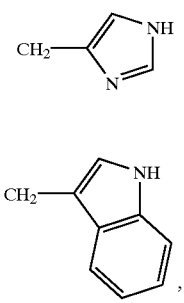

and (u)

or $R^3$ and $X^3$ together form a saturated monocyclic ring having the following structure:

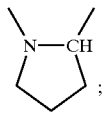

;

$R^4$ is selected from the group consisting of:
(a) H,
(b) $CH_3$,
(c) $CH(CH_3)_2$,
(d) $CH_2CH(CH_3)_2$,
(e) $CH_2Ph$,
(f) $CH_2PhOH$,
(g) $CH_2OH$,
(h) $CH_2SH$,
(i) $CH_2CH_2SCH_3$,
(j) $CH(CH_3)CH_2CH_3$,
(k) $CH(CH_3)OH$,
(l) $CH_2COOH$,
(m) $CH_2CH_2COOH$,
(n) $CH_2CH_2CH_2NHCNH(NH_2)$,
(o) $CH_2CH_2CH_2CH_2NH_2$,
(p) $CH_2C(O)NH_2$,
(q) $CH_2CH_2C(O)NH_2$, (r)

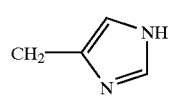

and (s)

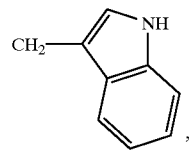

, or $R^4$ and $X^4$ together form a saturated monocyclic ring having the following structure:

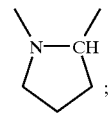

;

$R^5$ is selected from the group consisting of:
(a) $C_{1-6}$alkyl,
(b) aryl$C_{1-8}$alkyl wherein the aryl is selected from the group consisting of:
(1) phenyl,
(2) naphthyl,
(3) pyridyl,
(4) furyl,
(5) thienyl,
(6) thiazolyl,
(7) isothiazolyl,
(8) imidazolyl,
(9) benzimidazolyl,
(10) pyrazinyl,
(11) pyrimidyl,
(12) quinolyl,
(13) isoquinolyl,
(14) benzofuryl,
(15) benzothienyl,
(16) pyrazolyl,
(17) indolyl,
(18) purinyl,
(19) isoxazolyl,
(20) oxazolyl and
(21) coumarinyl and
(c) aryl as defined above in items (1) to (21) of (b), wherein the aryl portions may be optionally mono- or di-substituted with a substituent independently selected from:
(1) halo,
(2) amino,
(3) nitro,
(4) hydroxy,
(5) cyano,
(6) carboxy,
(7) formyl,
(8) amino carbonyl,
(9) $C_{1-6}$alkyl,
(10) $C_{1-6}$fluoroalkyl,
(11) $C_{1-6}$alkylcarbonyl,
(12) $C_{1-6}$alkoxycarbonyl,
(13) $C_{1-6}$alkoxy,
(14) $C_{1-6}$alkylthio and
(15) $C_{1-6}$alkylsulfonyl;
$R^6$ and $R^7$ are independently selected from the group consisting of:
(a) $C_{1-4}$alkyl,
(b) $C_{1-4}$fluoroalkyl and
(c) benzyl or mono- or disubstituted benzyl wherein the substituent is selected from the group consisting of:

(1) methyl,
(2) halogen,
(3) methoxy and
(4) cyano,
or $R^6$ and $R^7$ may be joined to form a pyrrolidine, piperidine, morpholine, thiamorpholine or N—$R^8$ substituted piperazine wherein $R^8$ is H or $C_{1-3}$alkyl; and $X^2$, $X^3$ and $X^4$ are independently H or $X^2$ and $R^2$, $X^3$ and $R^3$, or $X^4$ and $R^4$ may together form a saturated monocyclic ring having the following structure:

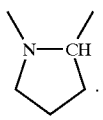

The invention also encompasses a pharmaceutical composition comprising a compound of formula I in combination with a pharmacuetically acceptable carrier.

The invention also encompasses a method of treating cardiac and cerebral ischemia/reperfusion injury (e.g. stroke), type I diabetes, immune deficiency syndrome (including AIDS), cerebral and spinal cord trauma injury, organ damage during transplantation, alopecia, aging, Parkinson's disease, Alzheimer's disease, Down's syndrome, spinal muscular atrophy, multiple sclerosis and neurodegenerative disorders, comprising administering to a mammalian patient in need of such treatment an effective amount of a compound of formula I.

DETAILED DESCRIPTION OF THE INVENTION

The invention encompasses the novel class of compounds represented by formula I, which are caspase-3 inhibitors.

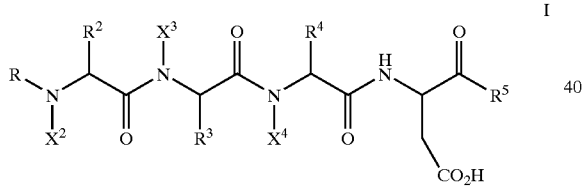

I or a pharmaceutically acceptable salt thereof, are disclosed, wherein:
R is selected from the group consisting of:
(a) H and
(b) $C(O)R^1$;
$R^1$ is selected from the group consisting of:
(a) hydrogen,
(b) $C_{1-6}$alkoxy,
(c) $NR^6R^7$,
(d) benzyloxy or mono- or disubstituted benzyloxy, wherein the substituent is selected from the group consisting of:
(1) methyl,
(2) halogen,
(3) methoxy and
(4) cyano,
(e) $C_{1-6}$alkyl or substituted $C_{1-6}$alkyl, wherein the substituent is selected from the group consisting of:
(1) hydroxy,
(2) halo,
(3) $C_{1-3}$alkoxy,
(4) $C_{1-3}$alkylthio,
(5) phenyl $C_{1-3}$alkoxy,
(6) phenyl $C_{1-3}$alkylthio,
(7) phenylcarboxy and
(8) carboxy,
(f) aryl or aryl$C_{1-6}$alkyl wherein the aryl group is selected from the group consisting of:
(1) phenyl,
(2) naphthyl,
(3) pyridyl,
(4) furyl,
(5) thienyl,
(6) thiazolyl,
(7) isothiazolyl,
(8) imidazolyl,
(9) benzimidazolyl,
(10) pyrazinyl,
(11) pyrimidyl,
(12) quinolyl,
(13) isoquinolyl,
(14) benzofuryl,
(15) benzothienyl,
(16) pyrazolyl,
(17) indolyl,
(18) purinyl,
(19) isoxazolyl and
(20) oxazolyl, and
(g) mono and di-substituted aryl as defined above in items (1) to (20) of (f), wherein the substituents are independently selected from:
(1) halo,
(2) amino,
(3) nitro,
(4) hydroxy,
(5) cyano,
(6) carboxy,
(7) formyl,
(8) amino carbonyl,
(9) $C_{1-6}$alkyl,
(10) $C_{1-6}$fluoroalkyl,
(11) $C_{1-6}$alkylcarbonyl,
(12) $C_{1-6}$alkoxycarbonyl,
(13) $C_{1-6}$alkoxy,
(14) $C_{1-6}$alkylthio,
(15) $C_{1-6}$alkylsulfonyl and
(16) deuterio;
$R^2$ is selected from the group consisting of:
(a) H,
(b) $CH_3$,
(c) $CH(CH_3)_2$,
(d) $CH_2CH(CH_3)_2$,
(e) $CH_2Ph$,
(f) $CH_2PhOH$,
(g) $CH_2OH$,
(h) $CH_2SH$,
(i) $CH_2CH_2SCH_3$,
(j) $CH(CH_3)CH_2CH_3$,
(k) $CH(CH_3)OH$,
(l) $CH_2COOH$,
(m) $CH_2CH_2COOH$,
(n) $CH_2CH_2CH_2NHCNH(NH_2)$,
(o) $CH_2CH_2CH_2CH_2NH_2$,
(p) $CH_2C(O)NH_2$,
(q) $CH_2CH_2C(O)NH_2$,
(r) $CH_2CO_2C_{1-4}$alkyl,
(s) $CH_2SC_{1-4}$alkyl,
(t) $CH_2S(O)_2C_{1-4}$alkyl,

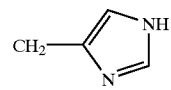

and

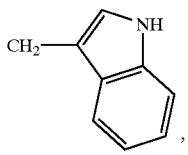

, or R² and X² together form a saturated monocyclic ring having the following structure:

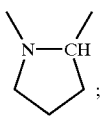

;

R³ is selected from the group consisting of:
(a) H,
(b) CH₃,
(c) CH(CH₃)₂,
(d) CH₂CH(CH₃)₂,
(e) CH₂Ph,
(f) CH₂PhOH,
(g) CH₂OH,
(h) CH₂SH,
(i) CH₂CH₂SCH₃,
(j) CH(CH₃)CH₂CH₃,
(k) CH(CH₃)OH,
(l) CH₂COOH,
(m) CH₂CH₂COOH,
(n) CH₂CH₂CH₂NHCNH(NH₂),
(o) CH₂CH₂CH₂CH₂NH₂,
(p) CH₂C(O)NH₂,
(q) CH₂CH₂C(O)NH₂,
(r) CH₂CH₂CO₂C₁₋₄alkyl,
(s) CH₂CH₂S(O)₂C₁₋₄alkyl, (t)

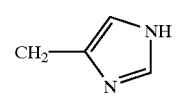

and (u)

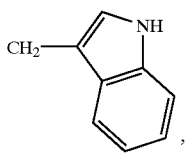

, or R³ and X³ together form a saturated monocyclic ring having the following structure:

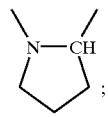

;

R⁴ is selected from the group consisting of:
(a) H,
(b) CH₃,
(c) CH(CH₃)₂,
(d) CH₂CH(CH₃)₂,
(e) CH₂Ph,
(f) CH₂PhOH,
(g) CH₂OH,
(h) CH₂SH,
(i) CH₂CH₂SCH₃,
(j) CH(CH₃)CH₂CH₃,
(k) CH(CH₃)OH,
(l) CH₂COOH,
(m) CH₂CH₂COOH,
(n) CH₂CH₂CH₂NHCNH(NH₂),
(o) CH₂CH₂CH₂CH₂NH₂,
(p) CH₂C(O)NH₂,
(q) CH₂CH₂C(O)NH₂, (r)

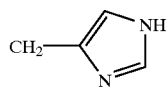

and (s)

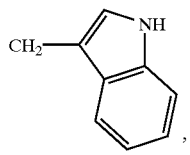

, or R⁴ and X⁴ together form a saturated monocyclic ring having the following structure:

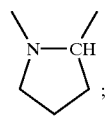

;

R⁵ is selected from the group consisting of:
(a) C₁₋₆alkyl,
(b) arylC₁₋₈alkyl wherein the aryl is selected from the group consisting of:
(1) phenyl,
(2) naphthyl,
(3) pyridyl,
(4) furyl,
(5) thienyl,
(6) thiazolyl,
(7) isothiazolyl,
(8) imidazolyl,
(9) benzimidazolyl,
(10) pyrazinyl,
(11) pyrimidyl,
(12) quinolyl,
(13) isoquinolyl,
(14) benzofuryl,
(15) benzothienyl,

(16) pyrazolyl,
(17) indolyl,
(18) purinyl,
(19) isoxazolyl,
(20) oxazolyl and
(21) coumarinyl, and
(c) aryl as defined above in items (1) to (21) of (b), wherein the aryl portions may be optionally mono- or di-substituted with a substituent independently selected from:
(1) halo,
(2) amino,
(3) nitro,
(4) hydroxy,
(5) cyano,
(6) carboxy,
(7) formyl,
(8) amino carbonyl,
(9) $C_{1-6}$alkyl,
(10) $C_{1-6}$fluoroalkyl,
(11) $C_{1-6}$alkylcarbonyl,
(12) $C_{1-6}$alkoxycarbonyl,
(13) $C_{1-6}$alkoxy,
(14) $C_{1-6}$alkylthio and
(15) $C_{1-6}$alkylsulfonyl;

$R^6$ and $R^7$ are independently selected from the group consisting of:
(a) $C_{1-4}$alkyl,
(b) $C_{1-4}$fluoroalkyl and
(c) benzyl or mono- or disubstituted benzyl wherein the substituent is selected from the group consisting of:
(1) methyl,
(2) halogen,
(3) methoxy and
(4) cyano,
or $R^6$ and $R^7$ may be joined to form a pyrrolidine, piperidine, morpholine, thiamorpholine or N—$R^8$ substituted piperazine wherein $R^8$ is H or $C_{1-3}$alkyl; and
$X^2$, $X^3$ and $X^4$ are independently H or $X^2$ and $R^2$, $X^3$ and $R^3$, or $X^4$ and $R^4$ may together form a saturated monocyclic ring having the following structure:

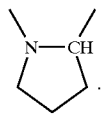

In a preferred embodiment, the compounds are represented by formula Ia

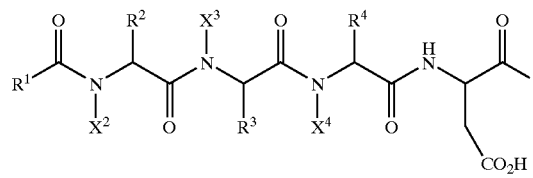

or a pharmaceutically acceptable salt thereof, wherein the amino acids from which the structure is constructed, represented in formula Ia as $AA^1$, $AA^2$ and $AA^3$, are selected from a group consisting of the L- and D-forms of the amino acids including alanine, arginine, asparagine, aspartic acid, cysteine, glutamine, glutamic acid, glycine, histidine, isoleucine, leucine, lysine, methionine, phenylalanine, proline, serine, threonine, tryptophane, tyrosine and valine. The structures of the L-amino acids are shown below.

L-amino acids and abbreviations:

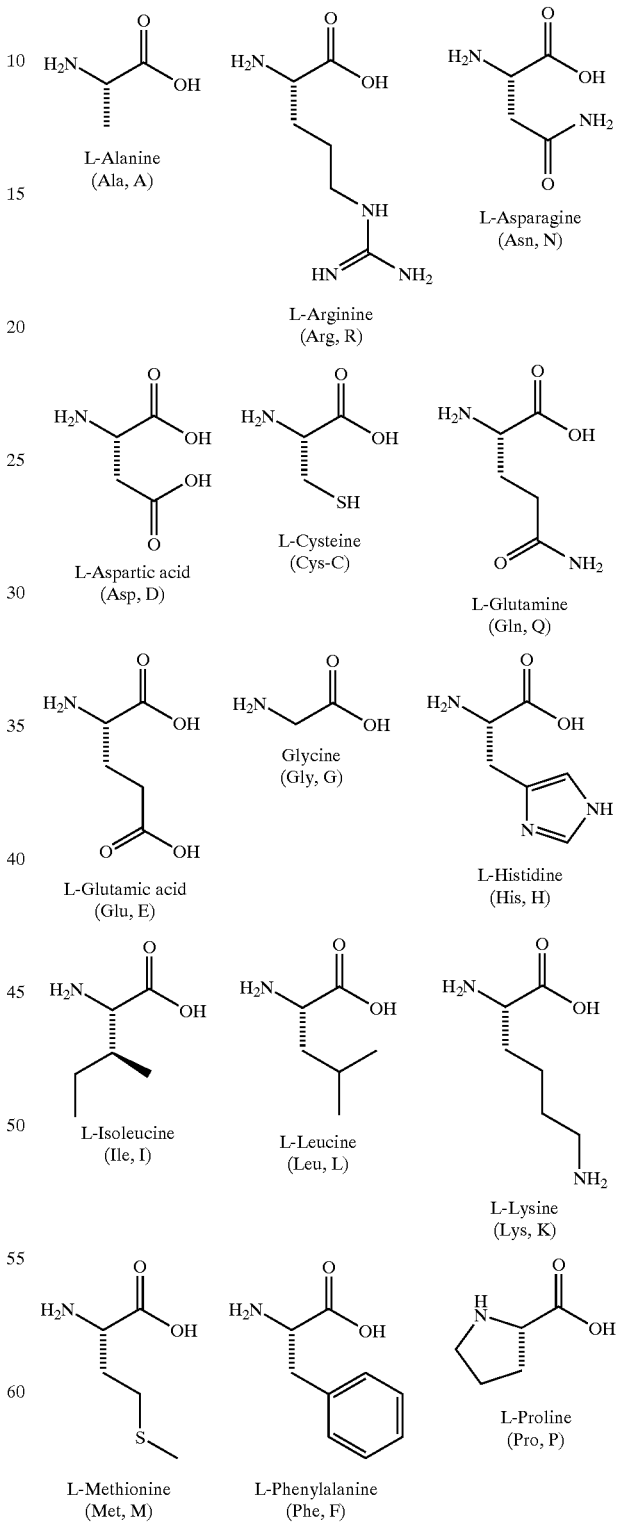

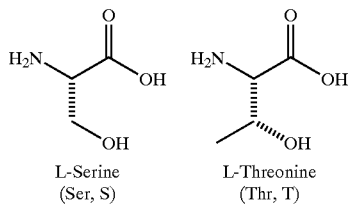

L-Serine (Ser, S)

L-Threonine (Thr, T)

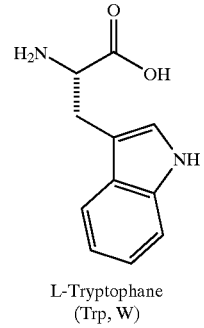

L-Tryptophane (Trp, W)

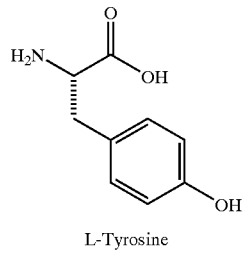

L-Tyrosine (Tyr, Y)

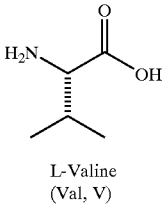

L-Valine (Val, V)

A preferred embodiment of the invention is that wherein $R^1$ is $C_{1-6}$alkyl or phenyl.

Another preferred embodiment of the invention is that wherein $R^5$ is aryl$C_{1-8}$alkyl, wherein aryl is selected from the group consisting of phenyl, naphthyl, pyridyl, and mono-, or di-substituted derivatives thereof, wherein the substituents are individually selected from the group consisting of:
(1) halo,
(2) amino,
(3) nitro,
(4) hydroxy,
(5) cyano,
(6) carboxy,
(7) formyl,
(8) amino carbonyl,
(9) $C_{1-3}$alkyl,
(10) $C_{1-3}$fluoroalkyl,
(11) $C_{1-3}$alkylcarbonyl,
(12) $C_{1-3}$alkoxycarbonyl,
(13) $C_{1-3}$alkoxy,
(14) $C_{1-3}$alkylthio and
(15) $C_{1-3}$alkylsulfonyl;

Another preferred embodiment of the present invention is that wherein:

$R^1$ is selected from the group consisting of:
(a) $C_{1-6}$alkoxy,
(b) benzyloxy or mono- or disubstituted benzyloxy, wherein the substituent is selected from methyl, halogen, methoxy and cyano,
(c) $C_{1-6}$alkyl or substituted $C_{1-6}$alkyl, wherein the substituent is selected from the group consisting of:
(1) hydroxy,
(2) halo,
(3) $C_{1-3}$alkoxy,
(4) $C_{1-3}$alkylthio,
(5) phenyl$C_{1-3}$alkoxy,
(6) phenyl$C_{1-3}$alkylthio,
(7) phenylcarboxy and
(8) carboxy,
(d) aryl or aryl$C_{1-6}$alkyl wherein the aryl group is selected from the group consisting of:
(1) phenyland
(2) naphthyl, and
(e) mono and di-substituted aryl as defined above in items (1) to (2) wherein the substituents are independently selected from:
(1) halo,
(2) hydroxy,
(3) cyano,
(4) carboxy,
(5) amino carbonyl,
(6) $C_{1-3}$alkyl,
(7) $C_{1-3}$fluoroalkyl,
(8) $C_{1-3}$alkylcarbonyl,
(9) $C_{1-3}$alkoxycarbonyl,
(10) $C_{1-3}$alkoxy,
(11) $C_{1-3}$alkylthio,
(12) $C_{1-3}$alkylsulfonyl and
(13) deuterio; and $R^5$ is aryl$C_{1-8}$alkyl wherein aryl is selected from the group consisting of phenyl, naphthyl, pyridyl, and mono-, or di-substituted derivatives thereof, wherein the substituents are individually selected from the group consisting of:
(1) halo,
(2) hydroxy,
(3) cyano,
(4) carboxy,
(5) amino carbonyl,
(6) $C_{1-3}$alkyl,
(7) $C_{1-3}$fluoroalkyl,
(8) $C_{1-3}$alkylcarbonyl,
(9) $C_{1-3}$alkoxycarbonyl,
(10) $C_{1-3}$alkoxy,
(11) $C_{1-3}$alkylthio and
(12) $C_{1-3}$alkylsulfonyl.

Another preferred embodiment of the invention is that wherein $R^1$ is selected from the group consisting of:
(a) $C_{1-6}$alkyl or substituted $C_{1-6}$alkyl, wherein the substituent is selected from the group consisting of:
(1) hydroxy,
(2) halo,
(3) $C_{1-3}$alkoxy,
(4) $C_{1-3}$alkylthio,
(5) phenyl$C_{1-3}$alkoxy,
(6) phenyl$C_{1-3}$alkylthio,
(7) phenylcarboxy and
(8) carboxy,
(b) aryl or aryl$C_{1-6}$alkyl wherein the aryl group is selected from the group consisting of:
(1) phenyl and
(2) naphthyl, and
(c) mono and di-substituted aryl as defined above in items (1) to (2) wherein the substituents are independently selected from:
(1) halo,
(2) hydroxy,
(3) cyano,
(4) carboxy,
(5) amino carbonyl,
(6) $C_{1-3}$alkyl,
(7) $C_{1-3}$fluoroalkyl,
(8) $C_{1-3}$alkylcarbonyl,
(9) $C_{1-3}$alkoxycarbonyl,
(10) $C_{1-3}$alkoxy,

(11) $C_{1-3}$alkylthio,
(12) $C_{1-3}$alkylsulfonyl and
(13) deuterio.

Another preferred embodiment of the present invention is that wherein $R^2$ is selected from the group consisting of:
(a) $CH_2CO_2H$,
(b) $CH_2CO_2C_{1-4}$alkyl,
(c) $CH_2SC_{1-4}$alkyl and
(d) $CH_2S(O)_2C_{1-4}$alkyl.

Another preferred embodiment of the invention is that wherein $R^3$ is selected from the group consisting of:
(a) $CH_3$,
(b) $CH_2CH_2CO_2H$,
(c) $CH_2CH_2CO_2C_{1-4}$alkyl,
(d) $CH_2CH_2S(O)_2C_{1-4}$alkyl.

A preferred embodiment of the present invention is that wherein $R^4$ is isopropyl.

Another preferred embodiment of the invention is that wherein $R^5$ is selected from the group consisting of:
(a) $C_{1-6}$alkyl,
(b) aryl$C_{1-8}$alkyl wherein the aryl is selected from the group consisting of:
(1) phenyl,
(2) naphthyl,
(3) pyridyl and
(4) coumarinyl, and
(c) aryl as defined above in items (1) to (4) of (b), wherein the aryl portions may be optionally mono- or di-substituted with a substituent independently selected from:
(1) halo,
(2) hydroxy,
(3) cyano,
(4) carboxy,
(5) amino carbonyl,
(6) $C_{1-3}$alkyl,
(7) $C_{1-3}$fluoroalkyl,
(8) $C_{1-3}$alkylcarbonyl,
(9) $C_{1-3}$alkoxycarbonyl,
(10) $C_{1-3}$alkoxy,
(11) $C_{1-3}$alkylthio and
(12) $C_{1-3}$alkylsulfonyl.

In one subset that is of particular interest, the compounds are represented by formula II:

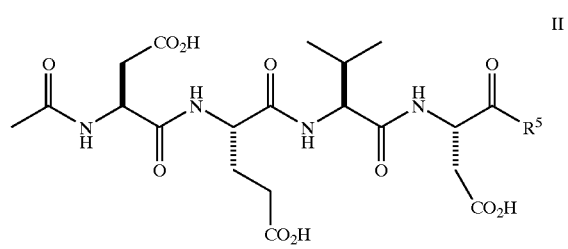

including pharmaceutically acceptable salts thereof, wherein:
$R^5$ is selected from the group consisting of:
(a) $C_{1-6}$alkyl,
(b) aryl$C_{1-8}$alkyl wherein the aryl is selected from the group consisting of:
(1) phenyl,
(2) naphthyl,
(3) pyridyl and
(4) coumarinyl and
(c) aryl as defined above in items (1) to (4) of (b), wherein the aryl portions may be optionally mono- or di-substituted with a substituent independently selected from:
(1) halo,
(2) hydroxy,
(3) cyano,
(4) carboxy,
(5) amino carbonyl,
(6) $C_{1-3}$alkyl,
(7) $C_{1-3}$fluoroalkyl,
(8) $C_{1-3}$alkylcarbonyl,
(9) $C_{1-3}$alkoxycarbonyl,
(10) $C_{1-3}$alkoxy,
(11) $C_{1-3}$alkylthio and
(12) $C_{1-3}$alkylsulfonyl.
(13)

Another subset of compounds that is of particular interest relates to compounds of formula II wherein:
$R^5$ is selected from the group consisting of:
(a) methyl,
(b) propyl,
(c) phenyl,
(d) phenyl$C_{1-5}$alkyl,
(e) 4-methoxyphenylpropyl,
(f) napthylpropyl and
(g) 4-methylcoumarinyl.
(h)

Representative compounds that are of particular interest are the following:

(SEQ ID NO 1)

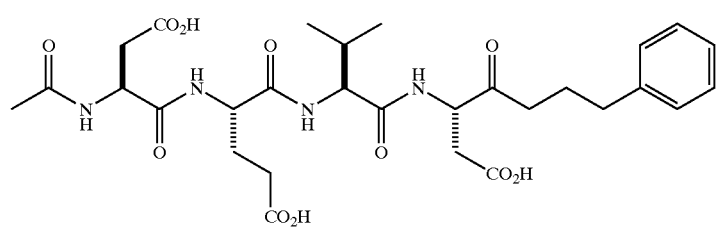

(SEQ ID NO 2)
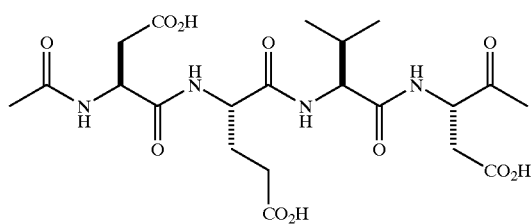
(SEQ ID NO 3)
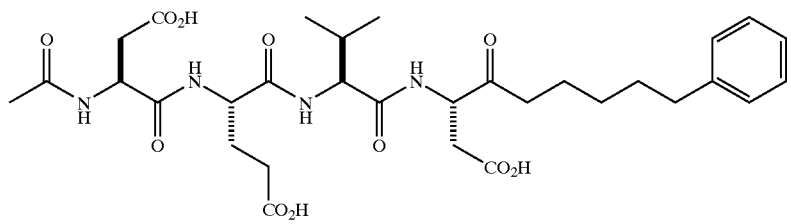
(SEQ ID NO 4)
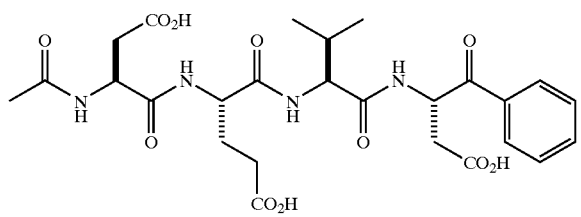
(SEC ID NO 5)
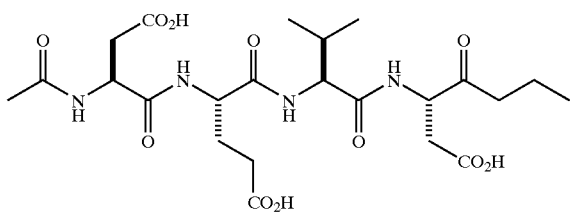
(SEQ ID NO 6)
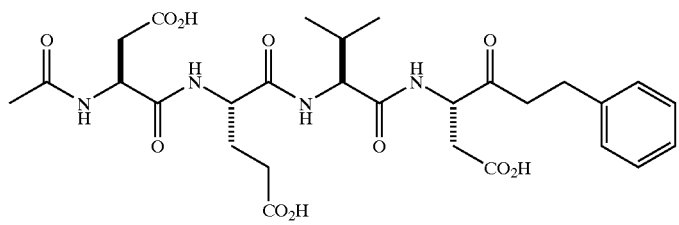
(SEC ID NO 7)
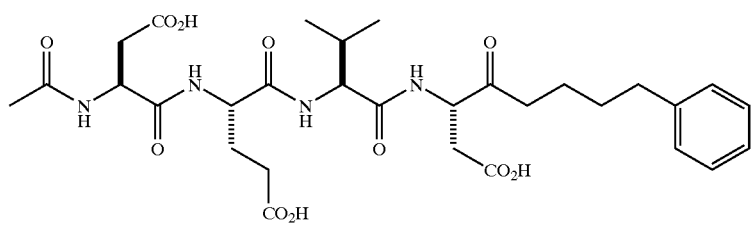
(SEQ ID NO 8)
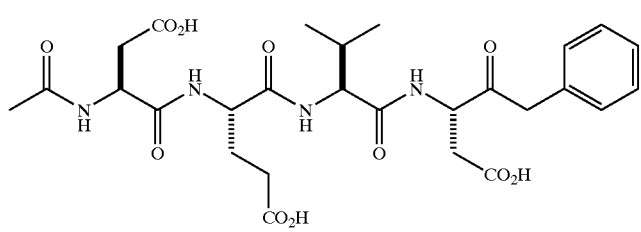
(SEQ ID NO 9)
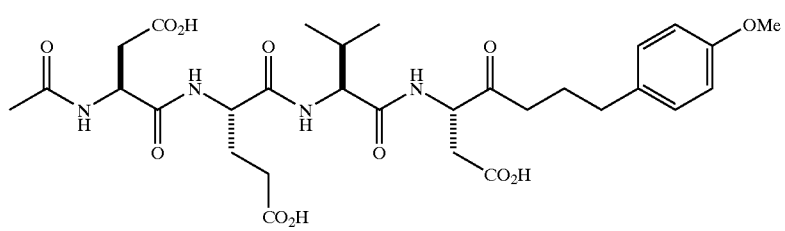

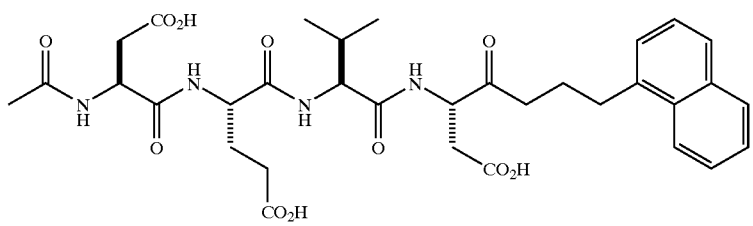

(SEQ ID NO 10)

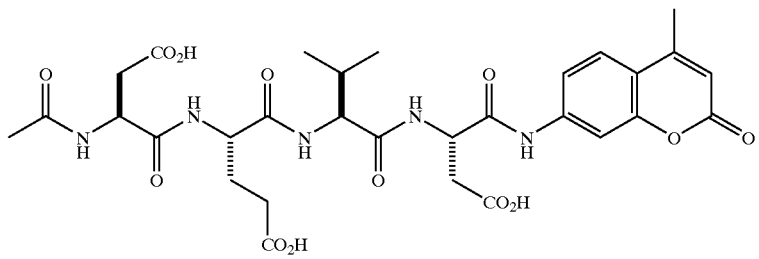

(SEQ ID NO 11)

In another embodiment that is of particular interest, the compounds are represented by formula III:

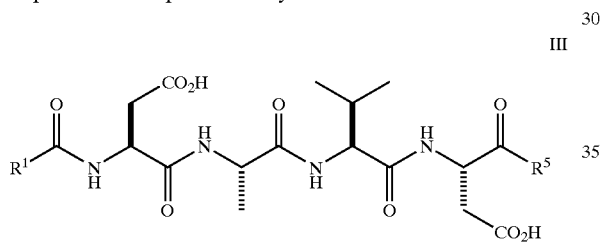

including pharmaceutically acceptable salts thereof, wherein:

$R^1$ is selected from the group consisting of:
(a) $C_{1-6}$alkyl or substituted $C_{1-6}$alkyl, wherein the substituent is selected from the group consisting of:
  (1) hydroxy,
  (2) halo,
  (3) $C_{1-3}$alkoxy,
  (4) $C_{1-3}$alkylthio,
  (5) phenyl$C_{1-3}$alkoxy,
  (6) phenyl$C_{1-3}$alkylthio,
  (7) phenylcarboxy and
  (8) carboxy,
(b) aryl or aryl$C_{1-6}$alkyl wherein the aryl group is selected from the group consisting of:
  (1) phenyl and
  (2) naphthyl, and
(c) mono and di-substituted aryl as defined above in items (1) to (2) wherein the substituents are independently selected from:
  (1) halo,
  (2) hydroxy,
  (3) cyano,
  (4) carboxy,
  (5) amino carbonyl,
  (6) $C_{1-3}$alkyl,
  (7) $C_{1-3}$fluoroalkyl,
  (8) $C_{1-3}$alkylcarbonyl,
  (9) $C_{1-3}$alkoxycarbonyl,
  (10) $C_{1-3}$alkoxy,
  (11) $C_{1-3}$alkylthio,
  (12) $C_{1-3}$alkylsulfonyl and
  (13) deuterio; and $R^5$ is aryl$C_{1-8}$alkyl wherein aryl is selected from the group consisting of phenyl, naphthyl, pyridyl, and mono-, or di-substituted derivatives thereof, wherein the substituents are individually selected from the group consisting of:
  (1) halo,
  (2) hydroxy,
  (3) cyano,
  (4) carboxy,
  (5) amino carbonyl,
  (6) $C_{1-3}$alkyl,
  (7) $C_{1-3}$fluoroalkyl,
  (8) $C_{1-3}$alkylcarbonyl,
  (9) $C_{1-3}$alkoxycarbonyl,
  (10) $C_{1-3}$alkoxy,
  (11) $C_{1-3}$alkylthio and
  (12) $C_{1-3}$alkylsulfonyl.

A subset of compounds that are of particular interest are defined in accordance with formula III wherein:

R1 is selected from the group consisting of:
  (a) methyl,
  (b) phenyl and
  (c) mono- or disubstituted phenyl, wherein the substituents are selected from the group consisting of:
    (1) halo and
    (2) deuterio; and R5 is aryl$C_{3-5}$alkyl wherein aryl is selected from the group consisting of phenyl and naphthyl.

Representative compounds that are of particular interest are the following:

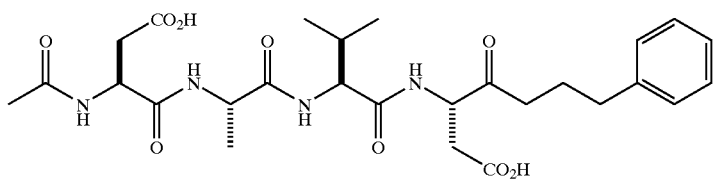
(SEC ID NO 12)
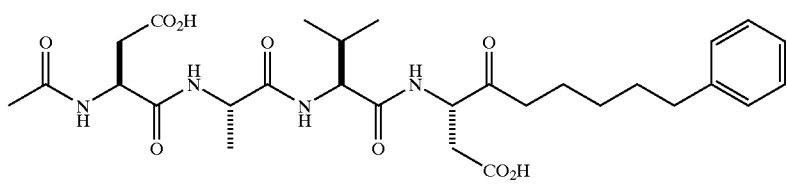
(SEC ID NO 13)
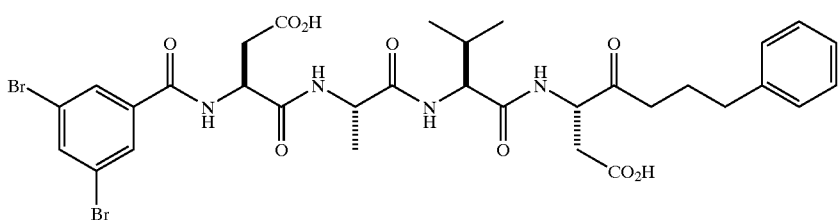
(SEC ID NO 14)
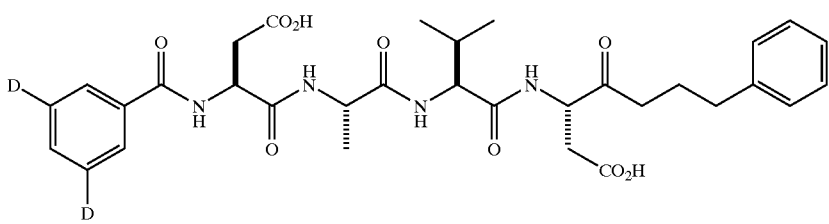
(SEC ID NO 15)
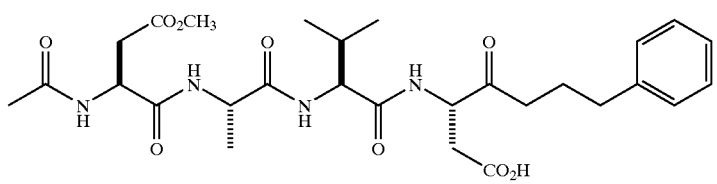
(SEC ID NO 26)
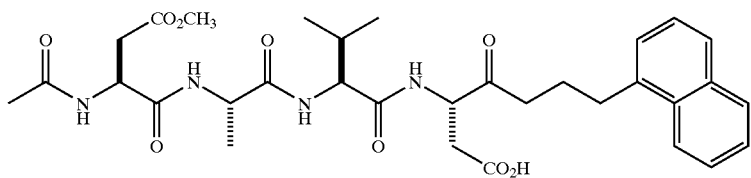
(SEQ ID NO 17)
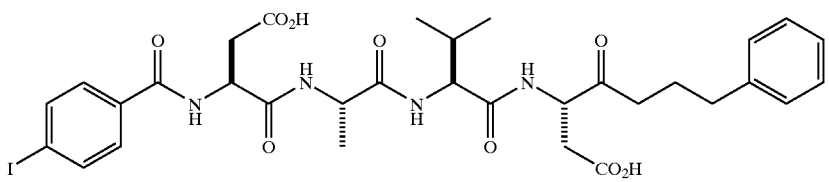
(SEQ ID NO 18)

Yet another embodiment that is of particular interest is represented by formula IV:

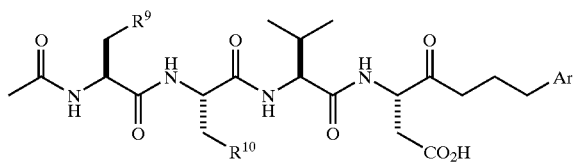

IV including pharmaceutically acceptable salts thereof, wherein:

$R^9$ is selected from the group consisting of:
(a) $CO_2H$,
(b) $CO_2C_{1-4}$alkyl,
(c) $SC_{1-4}$alkyl and
(d) $S(O)_2C_{1-4}$alkyl;

$R^{10}$ is selected from the group consisting of:
(a) H,
(b) $CH_2CO_2H$,
(c) $CH_2CO_2C_{1-4}$alkyl,
(d) $CH_2S(O)_2C_{1-4}$alkyl; and Ar is selected from the group consisting of:
(a) phenyl and
(b) napthyl.

A subset of compounds that are of particular interest are defined in accordance with formula IV wherein:

$R^9$ is selected from the group consisting of:
(a) $CO_2H$,
(b) $SCH_3$ and
(c) $S(O)_2CH_3$;

$R^{10}$ is selected from the group consisting of:
(a) H and
(d) $CH_2S(O)_2CH_3$; and Ar is phenyl or napthyl.

Representative compounds that are of particular interest are the following:

(SEQ ID NO 19)

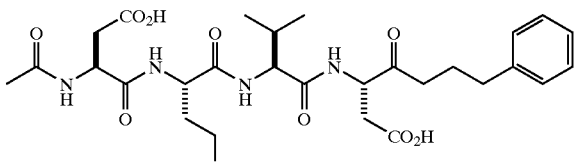

(SEQ ID NO 20)

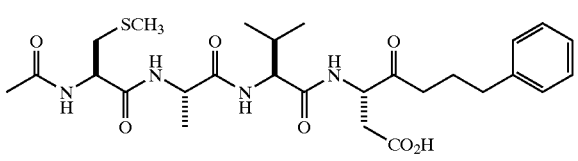

(SEQ ID NO 21)

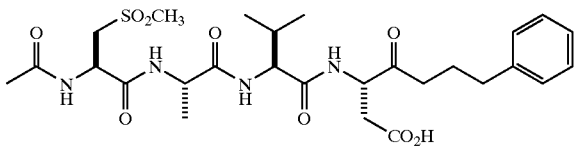

(SEQ ID NO 22)

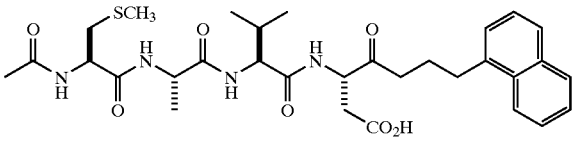

(SEQ ID NO 23)

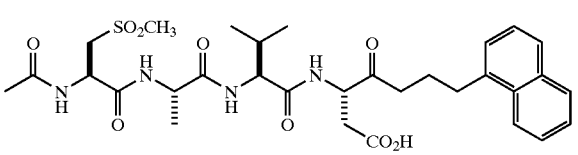

The invention also encompasses the following compound:

(SEQ ID NO 16)

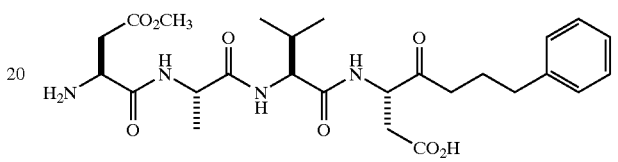

In a preferred embodiment, the invention encompasses a method of treating a caspase-3 mediated disease in a mammalian patient in need of such treatment, comprising administering to said patient a compound of formula I in an amount effective to treat said caspase-3 mediated disease.

In another embodiment, the invention encompasses a method of treating cardiac and cerebral ischemia/reperfusion injury (e.g. stroke), type I diabetes, immune deficiency syndrome (including AIDS), cerebral and spinal cord trauma injury, organ damage during transplantation, alopecia, aging, Parkinson's disease, Alzheimer's disease, Down's syndrome, spinal muscular atrophy, multiple sclerosis and neurodegenerative disorders, comprising administering to a mammalian patient in need of such treatment an effective amount of a compound of formula I.

In another embodiment, the invention encompasses a method of treating acute disorders, including cardiac and cerebral ischemia/reperfusion injury (e.g. stroke), spinal cord injury and organ damage during transplantation, in a mammalian patient in need of such treatment, comprising administering to said patient a compound of formula I in an amount effective to treat said acute disorder.

In another embodiment, the invention encompasses a method of treating chronic disorders, including neurodegenerative diseases (e.g. Alzheimer's, polyglutamine-repeat disorders, Down's, spinal muscular atrophy, multiple sclerosis), immunodeficiency (e.g. HIV), diabetes, alopecia and aging, in a mammalian patient in need of such treatment, comprising administering to said patient a compound of formula I in an amount effective to treat said chronic disorder.

In another embodiment, the invention encompasses a method of treating a caspase-3 mediated disease in a mammalian patient in need of such treatment, comprising administering to said patient a compound of formula II in an amount effective to treat said caspase-3 mediated disease.

In another embodiment, the invention encompasses a method of treating a caspase-3 mediated disease in a mammalian patient in need of such treatment, comprising administering to said patient a compound of formula III in an amount effective to treat said caspase-3 mediated disease.

In another embodiment, the invention encompasses a method of treating a caspase-3 mediated disease in a mammalian patient in need of such treatment, comprising administering to said patient a compound of formula IV in an amount effective to treat said caspase-3 mediated disease.

For purposes of this specification, the following abbreviations have the indicated meanings:

| | | |
|---|---|---|
| BOC | = | t-butyloxycarbonyl |
| CBZ | = | carbobenzoxy |
| DCC | = | 1,3-dicyclohexylcarbodiimide |
| DIBAL | = | diisobutyl aluminum hydride |
| DIEA | = | N,N-diisoproylethylamine |
| DMAP | = | 4-(dimethylamino)pyridine |
| EDCI | = | 1-(3-dimethylaminopropyl)-3-ethylcarbodiimide hydrochloride |
| EDTA | = | ethylenediaminetetraacetic acid, tetrasodium salt hydrate |
| FAB | = | fast atom bombardment |
| FMOC | = | 9-fluorenylmethoxycarbonyl |
| HMPA | = | hexamethylphosphoramide |
| HATU | = | O-(7-Azabenzotriazol-1-yl)N,N,N',N'-tetramethyluronium hexafluorophosphate |
| HOBt | = | 1-hydroxybenzotriazole |
| HRMS | = | high resolution mass spectrometry |
| ICBF | = | isobutyl chloroformate |
| KHMDS | = | potassium hexamethyldisilazane |
| LDA | = | lithium diisopropylamide |
| MCPBA | = | metachloroperbenzoic acid |
| Ms | = | methanesulfonyl = mesyl |
| MsO | = | methanefulfonate = mesylate |
| NBS | = | N-bromosuccinimide |
| NMM | = | 4-methylmorpholine |
| PCC | = | pyridinium chlorochromate |
| PDC | = | pyridinium dichromate |
| Ph | = | phenyl |
| PPTS | = | pyridinium p-toluene sulfonate |
| pTSA | = | p-toluene sulfonic acid |
| r.t. | = | room temperature |
| rac. | = | racemic |
| TfO | = | trifluoromethanesulfonate = triflate |
| TLC | = | thin layer chromatography |
| Alkyl group abbreviations | | |
| Me | = | methyl |
| Et | = | ethyl |
| n-Pr | = | normal propyl |
| i-Pr | = | isopropyl |
| n-Bu | = | normal butyl |
| i-Bu | = | isobutyl |
| s-Bu | = | secondary butyl |
| t-Bu | = | tertiary butyl |

For purposes of this specification alkyl means linear, branched or cyclic structures and combinations thereof, containing one to twenty carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclopentyl, cycloheptyl, adamantyl, cyclododecylmethyl, 2-ethyl-1-bicyclo[4.4.0]decyl and the like.

Alkylcarbonyl signifies groups having the formula —C(O)— alkyl, wherein alkyl is defined as above.

Alkylsulfonyl signifies groups having the formula —S(O)$_2$— alkyl, wherein alkyl is defined as above.

For purposes of this specification fluoroalkyl means linear, branched or cyclic alkyl groups and combinations thereof, of one to ten carbon atoms, in which one or more hydrogen but no more than six is replaced by fluorine. Examples are —CF$_3$, —CH$_2$CH$_2$F, and —CH$_2$CF$_3$, and the like.

Alkoxy means alkoxy groups of one to ten carbon atoms of a straight, branched or cyclic configuration. Examples of alkoxy groups include methoxy, ethoxy, propoxy, isopropoxy, and the like.

Alkoxycarbonyl signifies groups having the formula —C(O)— alkoxy, wherein alkoxy is defined as above.

Alkylthio means alkylthio groups of one to ten carbon atoms of a straight, branched or cyclic configuration. Examples of alkylthio groups include methylthio, propylthio, isopropylthio, etc. By way of illustration, the propylthio group signifies —SCH$_2$CH$_2$CH$_3$.

Aryl is, for example, phenyl, naphthyl, pyridyl, furyl, thienyl, thiazolyl, isothiazolyl, imidazolyl, benzimidazolyl, pyrazinyl, pyrimidyl, quinolyl, isoquinolyl, benzofuryl, benzothienyl, pyrazolyl, indolyl, purinyl, isoxazolyl, oxazolyl and coumarinyl.

Halo includes F, Cl, Br and I.

The compounds described typically contain asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of formula I as an active ingredient or a pharmaceutically acceptable salt thereof in combination with a pharmaceutically acceptable carrier, and optionally other therapeutic ingredients. The term "pharmaceutically acceptable salts" refers to salts prepared from pharmaceutically acceptable bases including inorganic bases and organic bases. Representative salts derived from inorganic bases include aluminum, ammonium, calcium, copper, ferric, ferrous, lithium, magnesium, manganic salts, manganous, ammonium, potassium, sodium, zinc and the like. Particularly preferred are the calcium, magnesium, potassium, and sodium salts. Representative salts derived from pharmaceutically acceptable organic bases include salts of primary, secondary and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable non-toxic acids, including inorganic and organic acids. Examples of such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric and tartaric acids.

In the discussion of methods of treatment which follows, reference to the compounds of formula I are meant to also include the pharmaceutically acceptable salts.

The ability of the compounds of formula I to inhibit caspase-3 make them useful research tools in the field of apoptosis. These compounds are also useful to treat, prevent or ameliorate in mammals and especially in humans, diseases including but not limited to:

1. cardiac and cerebral ischemia/reperfusion injury (e.g. stroke)
2. type I diabetes
3. immune deficiency syndrome (including AIDS)
4. cerebral and spinal cord trauma injury
5. organ damage during transplantation
6. alopecia
7. aging
8. Parkinson's disease
9. Alzheimer's disease
10. Down's syndrome
11. spinal muscular atrophy
12. multiple sclerosis
13. neurodegenerative disorders The magnitude of therapeutic dose of a compound of formula I will, of course, vary with the nature of the severity of the condition to be treated and with the particular compound of formula I and its route of administration and vary upon the clinician's judgement. It will also vary according to the age, weight and response of the individual patient. An effective dosage amount of the active component can thus be determined by the clinician after a consideration of all the criteria and using is best judgement on the patient's behalf. A representative dose will range from 0.001 mpk/d to about 100 mpk/d.

An ophthalmic preparations for ocular administration comprising 0.001–1% by weight solutions or suspensions of the compounds of formula I in an acceptable ophthalmic formulation may be used.

Any suitable route of administration may be employed for providing an effective dosage of a compound of the present invention. For example, oral, parenteral and topical may be employed. Dosage forms include tablets, troches, dispersions, suspensions, solutions, capsules, creams, ointments, aerosols, and the like.

The compositions include compositions suitable for oral, parenteral and ocular (ophthalmic). They may be conveniently presented in unit dosage form and prepared by any of the methods well-known in the art of pharmacy.

In practical use, the compounds of formula I can be combined as the active ingredient in intimate admixture with a pharmaceutical carrier according to conventional pharmaceutical compounding techniques. The carrier may take a wide variety of forms depending on the form of preparation desired for administration. In preparing the compositions for oral dosage form, any of the usual pharmaceutical media may be employed, such as, for example, water, alcohols, oils, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case or oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil emulsion. Such compositions may be prepared by any of the methods of pharmacy but all methods include the step of bringing into active ingredient with the carrier which constitutes one or more necessary ingredients. In general, the compositions are prepared by uniformLy and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. For example, each dosage unit may contain from about 0.01 mg to about 1.0 g of the active ingredient.

Method of Synthesis

Compounds of the instant invention are conveniently prepared using the procedures described generally below and more explicitly described in the Example section thereafter.

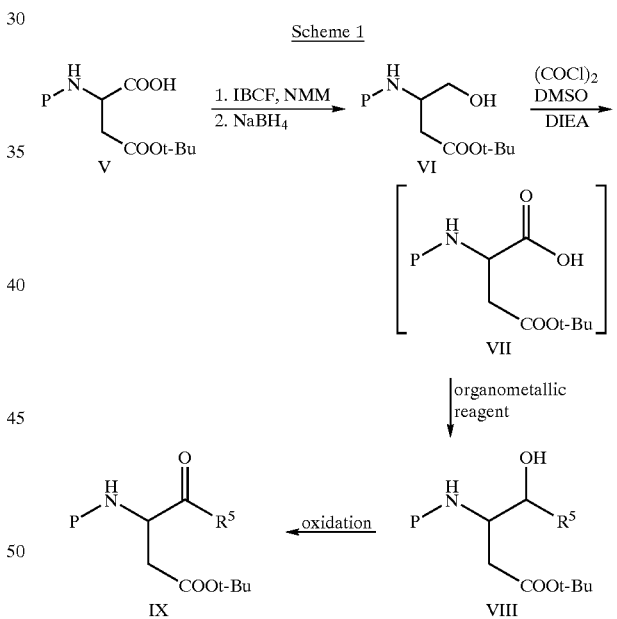

Scheme 1

A mixed anhydride of N-protected-L-aspartic acid β-tert-butyl ester (protected-L-Asp (OtBu)-OH)(V) and isobutyl-chloroformate (IBCF) is formed in the presence of N-methylmorpholine (NMM). This anhydride is reduced to the corresponding alcohol VI using sodium borohydride at −78° C. The alcohol VI is then oxidized using dimethyl sulfoxide (DMSO), oxalyl chloride, and N,N-diisopropylethylamine to the corresponding aldehyde. The aldehyde (VII) is not isolated but reacted immediately with an organometallic reagent to afford the secondary alcohol (VIII) which can be oxidized to the corresponding ketone (IX).

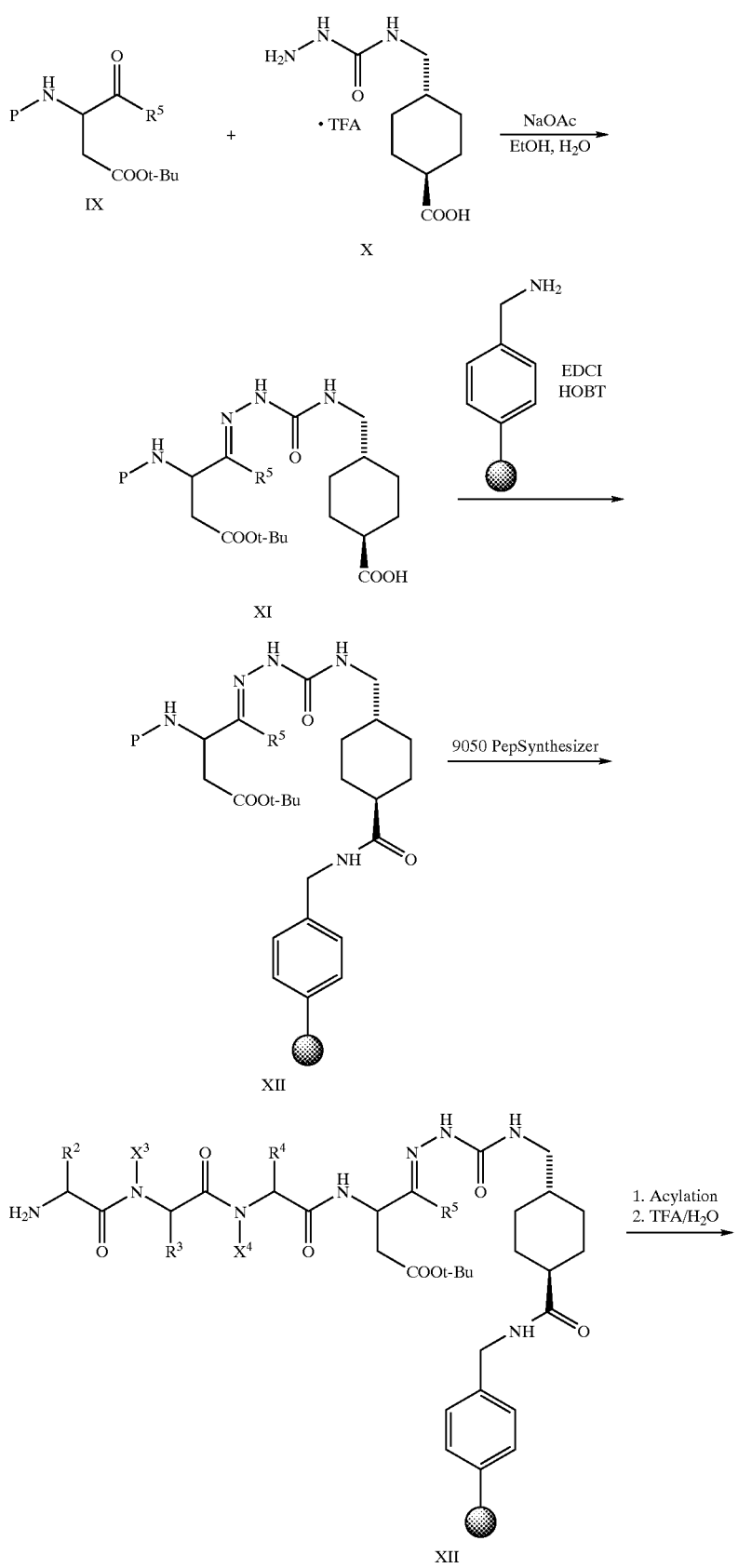

-continued

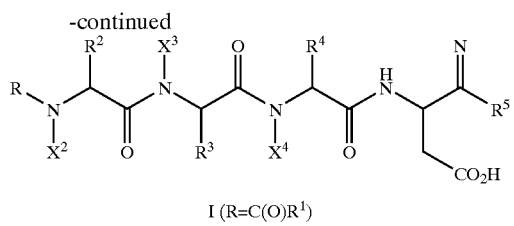

I (R=C(O)R¹)

The ketones IX are loaded onto a solid support using the technology described by Webb et al. (J. Am. Chem. Soc. 114, 3156 (1992)). This method uses the solution synthesis of the complete semicarbazone carboxylic acid linker XI by first reacting ketone IX with semicarbazidyl-trans-4-methyl cyclohexanecarboxylic acid trifluoroacetate salt (X) to give XI. Coupling of XI to the commercially available Merrifield resin gives the insoluble support XII. This material has all the physical and chemical properties for the automated synthesis of peptides.

Toward this end the 9050 Plus PepSynthesizer from PerSeptive Biosystems is used (Millipore Corporation, 34 Maple Street, Milford, Mass. 01757, User's Guide 9050 Plus OM 1.0). The synthesis procedure given in the user's guide is followed for the preparation of the tetrapeptide XIII on solid support.

O-(7-Azabenzotriazol-1-yl)N,N,N',N'-tetramethyluronium hexafluorophosphate (HATU) and N,N-diisoproylethylamine (DIEA) are used as coupling reagents instead of of TBTU and HOBt as described in the user's guide.

The uncapped tetrapeptide XIII is acylated and peptide I can be obtained by simultaneous deesterification and cleavage from solid support via exposure to a 9:1 mixture of TFA:H₂O.

The invention will now be illustrated by the following non-limiting examples in which, unless stated otherwise:
  (i) all operations were carried out at room or ambient temperature, that is, at a temperature in the range 18–25° C.,
  (ii) evaporation of solvent was carried out using a rotary evaporator under reduced pressure (600–4000 pascals: 4.5–30 mm. Hg) with a bath temperature of up to 60° C.,
  (iii) the course of reactions was followed by thin layer chromatography (TLC) and reaction times are given for illustration only;
  (iv) melting points are uncorrected and 'd' indicates decomposition; the melting points given are those obtained for the materials prepared as described; polymorphism may result in isolation of materials with different melting points in some preparations;
  (v) the structure and purity of all final products were assured by at least one of the following techniques: TLC, mass spectrometry, nuclear magnetic resonance (NMR) spectrometry or microanalytical data;
  (vi) yields are given for illustration only;
  (vii) when given, NMR data is in the form of delta (δ) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;
  (viii) chemical symbols have their usual meanings; the following abbreviations have also been used v (volume), w (weight), b.p. (boiling point), m.p. (melting point), L (litre(s)), mL (millilitres), g (gram (s)), mg (milligrams(s)), mol (moles), mmol (millimoles), eq (equivalent(s)).

EXAMPLE 1

(3S)-3-((2S)-2-[((2S)-2-[(2S)-2-(Acetylamino)-3-carboxypropanoyl]amino-4-carboxybutanoyl) amino]-3-methylbutanoylamino)-4-oxo-7-phenylheptanoic acid (SEQ ID NO 1)

Step 1: tert-Butyl (3S)-3-[(9H-9-fluorenylmethoxy) carbonyl]amino-4-hydroxybutanoate

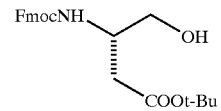

To a solution of N-Fmoc-L-aspartic acid b-tert-butyl ester (19.0 g, 46.2 mmol) in 300 mL of tetrahydrofuran (THF) at −78° C. was added N-methyl morpholine (NMM, 5.9 mL, 53.3 mmol) followed by isobutyl chloroformate (IBCF, 6.9 mL, 53.3 mmol). After 10 minutes this mixture was warmed to 0° C. for 40 minutes and then recooled to −78° C. A suspension of sodium borohydride (3.85 g, 102 mmol) in 25 mL of methanol was added and the mixture was stirred at −78° C. for 2 h. The reaction was quenched into 400 mL saturated aqueous ammonium chloride and extracted with ethyl acetate (4×100 mL). The combined organic layers were washed with brine and dried over anhydrous magnesium sulfate, filtered and concentrated. The residue was purified on silica gel (50% ethyl acetate/hexane) to give the desired product: 1H NMR (400 MHz, CD₃COCD₃) d 7.85 (d, 2H, J=7.30 Hz), 7.67 (d, 2H, J=7.37 Hz), 7.40 (t, 2H, J=7.30 Hz), 7.30 (t, 2H, J=7.30 Hz), 6.32 (brd, 1H), 4.40–4.15 (m, 3H), 4.10–3.98 (m, 1H), 3.92 (t, 1H), 3.65–3.48 (m, 2H), 2.60 (dd, 1H, J=6.24, 16.80 Hz), 2.41 (dd, 1H, J=6.30, 16.91 Hz), 1.40 (5, 9H).

Step 2: tert-Butyl (3S)-3-[(9H-9-fluorenylmethoxy) carbonyl]amino-4-oxo-7-phenylheptanoate

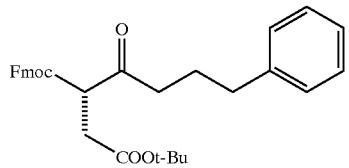

a) Oxalyl chloride (960 mL, 11 mmol) was added to a solution of DMSO (852 mL, 12 mmol) in 50 mL CH2Cl2 at -78° C. The resulting mixture was stirred at -78° C. for 30 minutes and the N-Fmoc-b-tert-butyl aspartic alcohol (3.98 g, 10 mmol) in CH$_2$Cl$_2$ (15 mL) was added dropwise. The mixture was stirred at -78° C. for 1 h, then i-Pr2NEt (5.20 mL, 30 mmol) was added dropwise. The resulting mixture was stirred at -78° C. for 50 min. and at 0° C. for 25 min. The mixture was recooled to -78° C. and phenylpropylmagnesium bromide (1.0M in Et2O, 30 mL) was added dropwise. The mixture was stirred at -78° C. for 2 h and at 0° C. for 75 min. Saturated aqueous NH$_4$Cl (100 mL) was added and the two layers were separated. The aqueous layer was further extracted with Et2O (4×100 mL). The combined organic layers were washed with 5% aq. HCl, 5% aq.NaHCO$_3$, brine, and dried over magnesium sulfate. The solvent was removed in vacuo and the residue was chromatographed over silica gel (15% EtOAc/toluene) to provide the secondary alcohol (4.48 g, 87%).

b) The secondary alcohol (1.5 g., 2.90 mmol) was dissolved in CH$_2$Cl$_2$ (20 mL) and Dess-Martin reagent (1.23 g., 2.90 mmol) was added. The resulting mixture was stirred for 2 h at room temperature and then filtered through a block of silica gel (15% EtOAc/toluene) to provide the phenylpropylketone (1.23 g, 83%): 1H NMR (400 MHz, CD$_3$COCD$_3$) d 7.85 (d, 2H, J=7.59 Hz), 7.68 (d, 2H, J=7.44 Hz), 7.40 (t, 2H, J=7.47 Hz), 7.31 (t, 2H, J=7.86 Hz), 7.25–7.08 (m, 5H), 6.85 (brd, 1H), 4.55–4.35 (m, 3H), 4.22 (t, 1H, J=6.95 Hz), 2.80 (dd, 1H, J=7.1, 16.1 Hz), 2.70–2.50 (m, 5H), 1.88 (q, 2H), 1.40 (s, 9H); MS (+APCI) m/z 514(M+H)+.

Step 3: 4-[(2-[(E,2S)-4-(tert-Butoxy)-2-[(9H-9-fluorenylmethoxy)carbonyl]amino-4-oxo-1-(3-phenylpropyl)butylidene]hydrazinocarbonyl)amino]methyl-1-cyclohexanecarboxylic acid

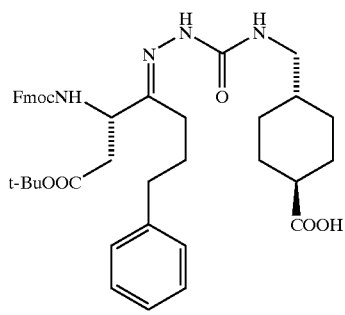

The following procedure is an adaption of Webb, T. R. et al., J. Am. Chem. Soc. 114, 3156 (1992); to a suspension of the phenylpropylketone (1.23 g, 2.39 mmol) and semicarbazidyl-trans-4-methyl cyclohexane carboxylic acid trifluoroacetate salt (0.79 g, 2.39 mmol) in EtOH/H2O (28 mL, 4:1) was added NaOAc (0.22 g, 2.63 mmol) followed by 8.5 mL THF. The clear solution was stirred at room emperature for 21 h. The mixture was poured into 100 mL brine, H$_2$O was added to dissolve the solid and extracted with EtOAc (4×25 mL). The organic layers were washed with saturated aq. NH4Cl and dried over MgSO4. Flash chromatography using 10% EtOAc/toluene, then 5% MeOH/CHCl3 gave 505 mg of recovered ketone and 1.1 g of the desired product: 1H NMR (400 MHz, CD$_3$COCD$_3$) d 9.12 (s, 1H), 8.00 (s,1H), 7.85 (d, 2H, J=7.52 Hz), 7.69 (t, 2H, J=6.60 Hz), 7.41 (t, 2H, J=7.50 Hz), 7.31 (t, 2H, J=7.44 Hz), 7.23–7.05 (m, 5H), 6.76 (brd, 1H, J=9.45 Hz), 6.64 (brt, 1H, J=5.69 Hz), 4.85–4.75 (m, 1H), 4.45–4.18 (m, 3H), 3.20–3.02 (m, 2H), 2.76–2.15 (m, 7H), 2.10–1.75 (m, 6H), 1.57–1.28 (m, 3H), 1.38 (s, 9H), 1.10–0.95 (m, 2H); MS (+APCI) m/z 711 (M+H)+.

Step 4: Resin IXa

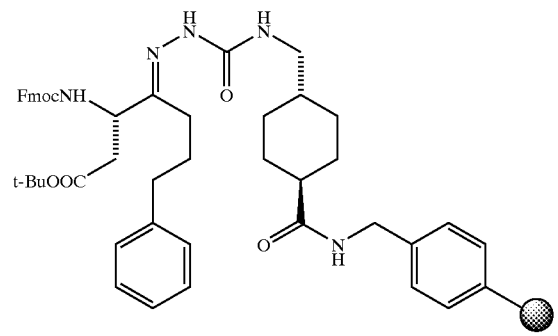

Merrifield's amino resin (2.02 g, 1.42 mmol, ca. 0.7 meq/g loading) is placed in a fritted reaction vessel. The resin is washed three times with DMF (10 mL each). After the last wash each of the following are added: carboxylic acid from step 3 (1.41 g, 1.98 mmol) in 36 mL CH$_2$Cl$_2$, 1-hydroxybenzotriazole (HOBT) (0.39 g, 2.55 mmol), 1-(3-dimethylaminopropyl) 3-ethycarbodiimide hydrochloride, (EDCI) (0.49 g, 2.55 mmol). The mixture is agitated overnight, filtered and then washed with CH$_2$Cl$_2$ (2×), sat. aq. NH$_4$Cl (3×), H$_2$O (2×), sat. aq. NaHCO$_3$ (2×), H$_2$O (2×), H$_2$O/THF (1:1, 2×), THF (2×), EtOAc (1×), CH$_2$Cl$_2$ (1×) (25 mL each). After drying 3.25 g of resin is obtained.

Step 5: (3S)-3-((2S)-2-[((2S)-2-[(2S)-2-(Acetylamino)-3-carboxypropanoyl]amino-4-carboxybutanoyl)amino]-3-methylbutanoylamino)-4-oxo-7-phenylheptanoic acid (SEQ ID NO 1)

(SEQ ID NO 1)

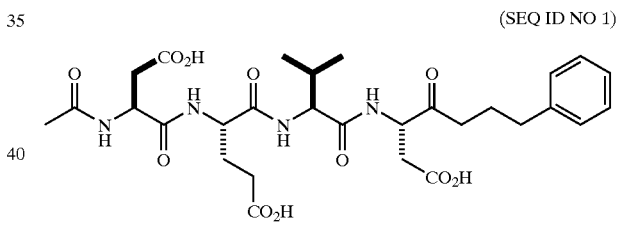

The PerSeptive 9050 Plus PepSynthesizer (Millipore Corporation, 34 Maple Street, Milford, Mass. 01757, User's Guide 9050 Plus OM 1.0) was used for the preparation of the tetrapeptide on solid support.

Preparation of the Tetrapeptide on Solid Support

Using the synthesis procedure given in the user's guide the tetrapeptide was prepared with the following reagents: 290 mg of polymer from Step 4 (0.7 meq/g loading), Fmoc-L-Val-OH (1.65 g), Fmoc-L-Glu (OtBu)-OH (1.83 g), Fmoc-L-Asp (OtBu)-OH (1.80 g); O-(7-azabenzotriazol-1-yl)N,N,N',N'-tetramethyluronium hexafluorophosphate (HATU) and N,N-diisopropylethylamine (DIEA) were used as coupling reagents instead of TBTU and HOBt as described in the user's guide.

Acetylation

The uncapped tetrapeptide on solid support was transferred into a fritted reaction vessel and treated with acetylimidazole (550 mg, 5 mmol) in 5 mL DMF. The mixture is agitated for 1.5 h, filtered and then washed with DMF (3×), THF (3×), CH$_2$Cl$_2$ (4×) (2 mL each).

Cleavage from Solid Support

The above polymer was treated with TFA:H$_2$O (9:1, 2 mL) and agitated for 30 min. The solution was filtered, the solid support washed with TFA (2×0.5 mL) and the filtrate was evaporated. Trituration from Et$_2$O gives 58 mg of the tetrapeptide derivative as a colorless solid. $^1$H NMR (400 MHz, CD$_3$OD) δ8.32 (d, 1H, J=7.20 Hz), 7.90 (d, 1H, J=8.08 Hz), 7.30–7.10 (m, 5H), 4.67 (t, 1H, J=6.60 Hz), 4.62 (t, 1H, J=6.23 Hz), 4.40–4.32 (m, 1H), 4.13 (t, 1H, J=7.60 Hz), 2.90–2.80 (m, 2H), 2.78–2.35 (m, 8H), 2.20–2.05 (m, 2H), 2.02–1.90 (m, 1H) 1.98 (s, 3H), 1.89–1.79 (m, 2H), 0.94 (d, 6H, J=6.71 Hz); MS (+APCI) m/z 621 (M+H)$^+$.

EXAMPLE 2

(4S)-4-[(2S)-2-(Acetylamino)-3-carboxypropanoyl]amino-5-[(1S)-1-([(1S)-1-(carboxymethyl)-2-oxopropyl]aminocarbonyl)-2-methylpropyl]amino-5-oxopentanoic acid (SEQ ID NO 2)

Step 1: tert-Butyl (3S)-3-[(9H-9-fluorenylmethoxy)carbonyl]amino-4-oxopentanoate

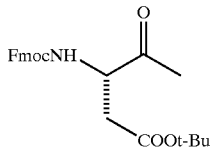

Following the procedure of Example 1, Step 2, substituting phenylpropylmagnesium bromide for methylmagnesium bromide the title compound was obtained: $^1$H NMR (400 MHz, CD$_3$COCD$_3$) δ7.85 (d, 2H, J=7.60 Hz), 7.68 (d, 2H, J=7.45 Hz), 7.41 (t, 2H, J=7.47 Hz), 7.32 (t, 2H, J=7.80 Hz), 6.85 (brd, 1H), 4.55–4.35 (m, 3H), 4.26 (t, 1H, J=6.95 Hz), 2.80 (dd, 1H, J=7.1, 16.1 Hz), 2.65 (dd, 1H), 2.18 (s, 3H), 1.41 (s, 9H).

Step 2: 4-[([2-((E,2S)-4-(tert-Butoxy)-2-[(9H-9-fluorenylmethoxy)carbonyl]amino-1-methyl-4-oxobutylidene)hydrazino]carbonylamino)methyl]-1-cyclohexanecarboxylic acid

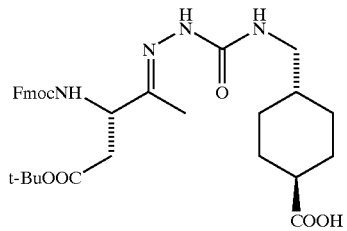

Following the procedure of Example 1, step 3, the title compound was obtained: $^1$H NMR (400 MHz, CD$_3$COCD$_3$) δ8.51 (s, 1H), 7.85 (d, 2H, J=7.50 Hz), 7.69 (d, 2H, J=6.60 Hz), 7.40 (t,2H, J=7.50 Hz), 7.31 (t, 2H, J=7.44 Hz), 6.75 (brd, 1H), 6.58 (brt, 1H), 4.74–4.62 (m, 1H), 4.45–4.20 (m, 3H), 3.20–3.00 (m, 2H), 2.88–2.55 (m, 3H), 2.28–1.70 (m, 5H), 1.98 (s, 3H), 1.55–1.28 (m, 3H), 1.45 (s, 9H), 1.10–0.95 (m, 2H); MS (+APCI) m/z 607 (M+H)$^+$.

Step 3: Resin IX (R$^5$=Me)

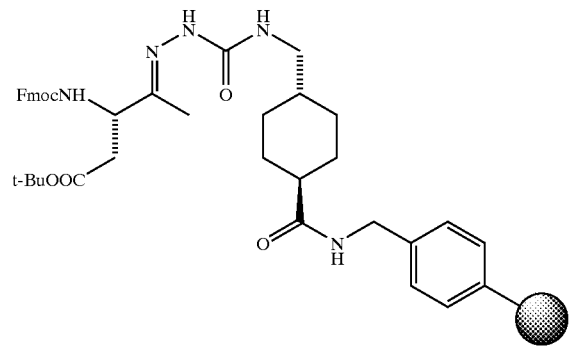

Following the procedure of Example 1, step 4, the title resin was obtained.

Step 4: (4S)-4-[(2S)-2-(Acetylamino)-3-carboxypropanoyl]amino-5-[(1S)-1-([(1S)-1-(carboxymethyl)-2-oxopropyl]aminocarbonyl)-2-methylpropyl]amino-5-oxopentanoic acid (SEQ ID NO 2)

(SEQ ID NO 2)

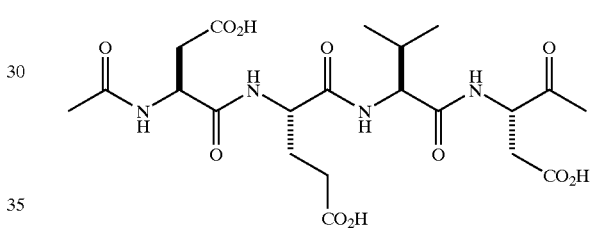

Following the procedure of Example 1, step 5, the title compound was obtained: $^1$H NMR (400 MHz, CD$_3$OD) δ8.33 (d, 1H, J=6.95 Hz), 7.92 (d, 1H, J=7.90 Hz), 4.67 (t, 1H, J=6.70 Hz), 4.60 (t, 1H, J=6.20 Hz), 4.40–4.33 (m, 1H), 4.14 (t, 1H, J=7.70 Hz), 2.91–2.81 (m, 2H), 2.78–2.65 (m, 2H), 2.50–2.34 (m, 2H), 2.20–2.08 (m, 2H), 2.17 (s, 3H), 2.01–1.89 (m, 1H), 1.99 (s, 3H), 0.96 (d, 6H, J=6.79 Hz); MS (+APCI) m/z 517 (M+H)$^+$.

EXAMPLE 3

(3S)-3-((2S)-2-[((2S)-2-[(2S)-2-(Acetylamino)-3-carboxypropanoyl]amino-4-carboxybutanoyl)amino]-3-methylbutanoylamino)-4-oxo-9-phenylnonanoic acid (SEQ ID NO 3)

Step 1: tert-Butyl (3S)-3-[(9H-9-fluorenylmethoxy)carbonyl]amino-4-oxo-9-phenylnonanoate

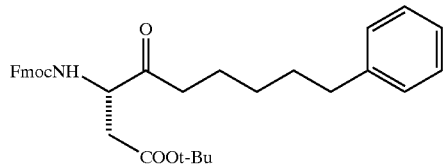

Following the procedure of Example 1, Step 2, substituting phenylpropylmagnesium bromide for phenylpentylmagnesium bromide the title compound was obtained: $^1$H NMR (400 MHz, CD$_3$COCD$_3$) δ7.85 (d, 2H, J=7.6 Hz), 7.68 (d, 2H, J=7.4 Hz), 7.40 (t, 2H, J=7.5 Hz), 7.31 (t, 2H, J=7.4 Hz), 7.11–7.27 (5H, m), 6.83 (brd, 1H, J=8.4 Hz), 4.35–4.51 (m, 3H), 4.24 (t, 1H, J=6.8 Hz), 2.80 (dd, 1H, J=6.0, 9.0 Hz), 2.46–2.65 (m, 5H), 1.55–1.64 (m, 4H), 1.28–1.41 (m, 2H), 1.41 (s, 9H).

Step 2: 4-[(2-[(E)-1-((1S)-3-(tert-Butoxy)-1-[(9H-9-fluorenylmethoxy)carbonyl]amino-3-oxopropyl)-6-phenylhexylidene]hydrazinocarbonyl)amino]methyl-1-cyclohexanecarboxylic acid

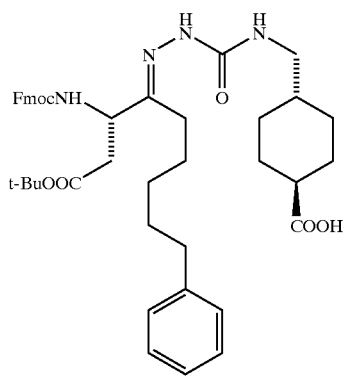

Following the procedure of Example 1, step 3, the title compound was obtained: 1H NMR (400 MHz, CD$_3$COCD$_3$) δ9.66 (s, 1H), 7.84 (d, 2H, J=7.5 Hz), 7.67 (d, 2H, J=7.5 Hz), 7.39 (t, 2H, J=7.5 Hz), 7.08–7.32 (m, 8H), 6.72 (brt, 1H, J=4.3 Hz), 4.79 (dd, 1H, J=8.5, 14.7 Hz), 4.33–4.43 (m, 2H), 4.21 (brt, 1H, J=6.9 Hz), 3.03–3.21 (m, 2H), 2.72 (dd, 1H, J=8.7, 14.8 Hz), 2.40–2.65 (m, 4H), 2.17–2.39 (m, 2H), 1.97–2.08 (m, 2H), 1.87 (brd, 2H, J=10.4 Hz), 1.30–1.68 (m, 5H), 1.40 (s, 9H), 0.95–1.10 (m, 2H).

Step 3: Resin IX (R$^5$=5-phenylpent-1-yl)

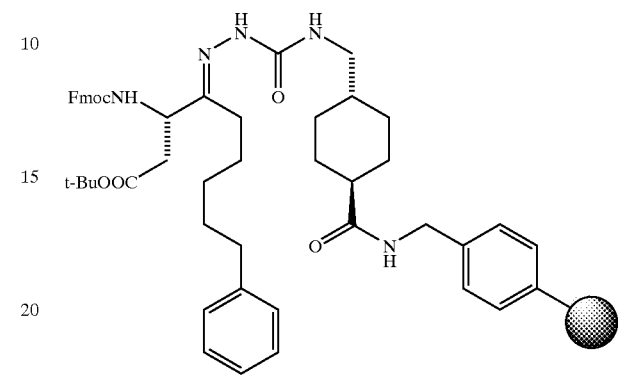

Following the procedure of Example 1, step 4, the title resin was obtained.

Step 4: (3S)-3-((2S)-2-[((2S)-2-[(2S)-2-(Acetylamino)-3-carboxypropanoyl]amino-4-carboxybutanoyl)amino]-3-methylbutanoylamino)-4-oxo-9-phenylnonanoic acid (SEQ ID NO 3)

(SEQ ID NO 3)

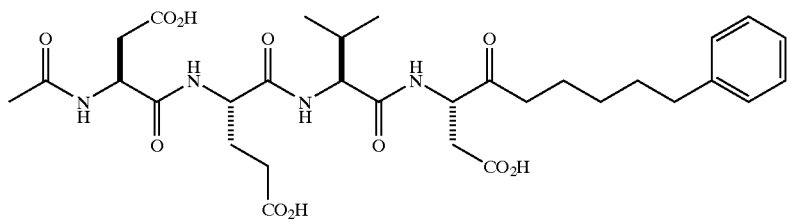

Following the procedure of Example 1, step 5, the title compound was obtained: $^1$H NMR (400 MHz, CD$_3$OD) δ7.86 (d, 1H, J=8.4 Hz), 7.09–7.24 (m, 5H), 4.62–4.69 m, 2H), 4.35 (dd, 1H, J=4.8, 8.8 Hz), 4.13–4.18 (m, 1H), 2.79–2.90 (m, 2H), 2.33–2.77 (m, 8H), 2.05–2.20 (m, 2H), 1.99 (s, 3H), 1.86–2.00 (m, 1H), 1.50–1.64 (m, 4H), 1.24–1.87 (m, 2H), 0.95 (d, 6H, J=6.7 Hz); MS (–APCI) m/z 647 (M–H)$^-$.

EXAMPLE 4

(4S)-4-[(2S)-2-(Acetylamino)-3-carboxypropanoyl]amino-5-[(1S)-1-([(1S)-1-(carboxymethyl)-2-oxo-2-phenylethyl]aminocarbonyl)-2-methylpropyl]amino-5-oxopentanoic acid (SEQ ID NO 4)

Step 1: tert-Butyl (3S)-3-[(9H-9-fluorenylmethoxy)carbonyl]amino-4-oxo-4-phenylbutanoate

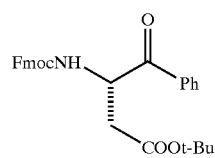

Following the procedure of Example 1, Step 2, substituting phenylpropylmagnesium bromide for phenylmagnesium bromide the title compound was obtained: $^1$H NMR (400 MHz, CD$_3$COCD$_3$) δ8.05 (d, 2H, J=7.6 Hz), 7.83 (d, 2H, J=7.6 Hz), 7.61–7.65 (m, 3H), 7.53 (t, 2H, J=7.8 Hz), 7.38 (d, 1H, J=7.5 Hz), 7.27 (dt, 2H, J=0.9, 7.5 Hz), 7.05 (brd, 1H, J=8.7 Hz), 5.55 (brq, 1H, J=8.6 Hz), 4.32–4.34 (m, 2H), 4.19 (t, 1H, J=7.0 Hz), 2.95 (dd, 1H, J=7.1, 16.1 Hz), 2.66 (dd, 1H, J=6.3, 16.1 Hz), 1.38 (s, 9H).

Step 2: 4-[((2-((E,2S)-4-(tert-Butoxy)-2-[(9H-9-fluorenylmethoxy)carbonyl]amino-4-oxo-1-phenylbutylidene)hydrazino]carbonylamino)methyl]-1-cyclohexanecarboxylic acid

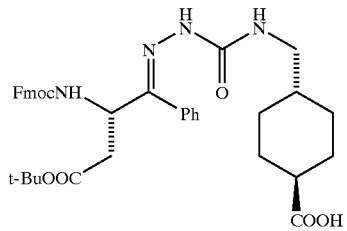

Following the procedure of Example 1, step 3, the title compound was obtained: $^1$H NMR (400 MHz, CD$_3$COCD$_3$) δ8.00 (s, 1H), 7.83 (d, 2H, J=7.6 Hz), 7.59 (t, 2H, J=7.7 Hz), 7.50 (t, 2H, J=7.5 Hz), 7.11–7.45 (m, 7H), 6.88 (d, 1H, J=9.3 Hz), 6.76 (brt, 1H, J=5.8 Hz), 5.01–5.64 (m, 1H), 4.21–4.91 (m, 2H), 4.13 (brt, 1H, J=7.1 Hz), 3.03–3.22 (m, 2H), 2.85 (dd, 1H, J=7.7, 14.9 Hz), 2.66 (dd, 1H, J=6.3, 15.1 Hz), 2.20 (brt, 1H, J=3.3 Hz), 1.98 (brd, 2H, J=13.0 Hz), 1.86 (brd, 2H, J=12.8 Hz), 1.44 (s, 9H), 1.28–1.60 (m, 3H), 0.94–1.06 (m, 2H).

Step 3: Resin IX (R$^5$=phenyl)

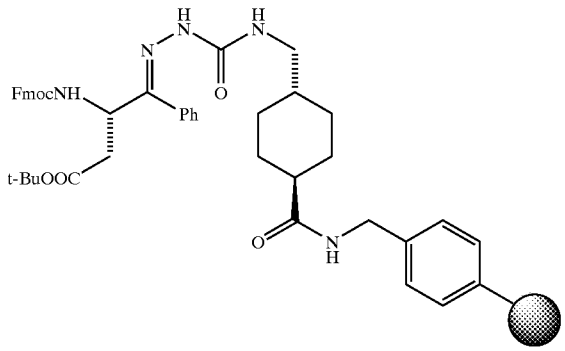

Following the procedure of Example 1, step 4, the title resin was obtained.

Step 4: (4S)-4-[(2S)-2-(Acetylamino)-3-carboxypropanoyl]amino-5-[(1S)-1-([(1S)-1-(carboxymethyl)-2-oxo-2-phenylethyl]aminocarbonyl)-2-methylpropyl]amino-5-oxopentanoic acid (SEQ ID NO 4)

(SEQ ID NO 4)

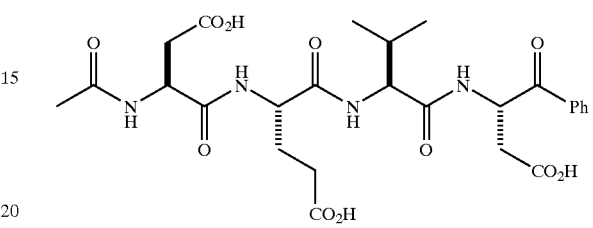

Following the procedure of Example 1, step 5, the title compound was obtained: $^1$H NMR (400 MHz, CD$_3$OD) δ7.96 (d, 1H, J=7.2 Hz), 7.59 (t, 1H, J=7.4 Hz), 7.47 (t, 2H, J=7.8 Hz), 5.70 (dd, 1H, J=5.9, 7.7 Hz), 4.68 (t, 1H, J=7.0 Hz), 4.33 (dd, 1H, J=5.1, 9.1 Hz), 4.06 (d, 1H, J=7.2 Hz), 3.02 (dd, 1H, J=7.8, 16.7 Hz), 2.85 (dd, 1H, J=6.1, 17.0 Hz), 2.71 (dd, 1H, J=7.2, 17.0 Hz), 2.66 (dd, 1H, J=5.8, 16.7 Hz), 2.31–2.40 (m, 2H), 1.83–2.10 (m, 3H), 1.99 (s, 3H), 0.82 (d, 3H, J=6.8 Hz), 0.77 (d, 3H, J=6.8 Hz); MS (−APCI) m/z 577 (M−H)$^-$.

EXAMPLE 5

(3S)-3-((2S)-2-[((2S)-2-[(2S)-2-(Acetylamino)-3-carboxypropanoyl]amino-4-carboxybutanoyl)amino]-3-methylbutanoylamino)-4-oxoheptanoic acid (SEQ ID NO 5)

Step 1: tert-Butyl (3S)-3-[(9H-9-fluorenylmethoxy)carbonyl]amino-4-oxoheptanoate

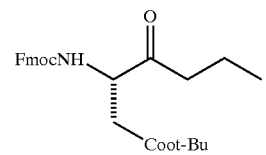

Following the procedure of Example 1, Step 2, substituting phenylpropylmagnesium bromide for n-propylmagnesium bromide, the title compound was obtained: $^1$H NMR (400 MHz, CD$_3$COCD$_3$) δ7.84 (d, 2H, J=7.5 Hz), 7.68 (d, 2H, J=7.5 Hz), 7.40 (t, 2H, J=7.4 Hz), 7.31 (t, 2H, J=7.4 Hz), 6.83 (d, 1H, J=8.3 Hz), 4.36–4.55 (m, 3H), 4.23 (t, 1H, J=6.9 Hz), 2.82 (dd, 1H, J=6.9, 22.1 Hz), 2.48–2.67 (m, 3H), 1.51–1.61 (m, 2H), 1.41 (s, 9H), 0.88 (t, 3H, J=7.4 Hz).

Step 2: 4-[([2-((E,2S)-4-(tert-Butoxy)-2-[(9H-9-fluorenylmethoxy)carbonyl]amino-4-oxo-1-propylbutylidene)hydrazino]carbonylamino)methyl]-1-cyclohexanecarboxylic acid

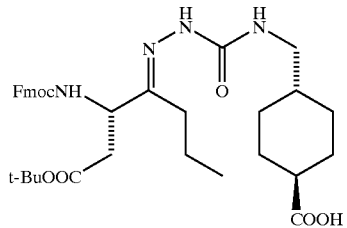

Following the procedure of Example 1, step 3, the title compound was obtained: $^1$H NMR (400 MHz, CD$_3$COCD$_3$) δ7.83 (d, 2H, J=7.5 Hz), 7.63 (d, 2H, J=7.3 Hz), 7.37 (t, 2H, J=7.3 Hz), 7.29 (t, 2H, J=7.4 Hz), 7.19 (d, 1H, J=7.3 Hz), 7.14 (s, 1H), 6.75 (brt, 1H, J=6.0 Hz), 4.68 (dd, 1H, J=6.2, 8.7 Hz), 4.35–4.49 (m, 2H), 4.19 (t, 1H, J=6.5 Hz), 3.01–3.16 (m, 2H), 2.66 (dd, 1H, J=8.8, 14.8 Hz), 2.51 (dd, 1H, J=7.9, 14.7 Hz), 2.10–2.34 (m, 3H), 1.99 (brd, 2H, J=12.6 Hz), 1.86 (brd, 2H, J=14.6 Hz), 1.30–1.58 (m, 5H), 1.39 (s, 9H), 0.86–1.06 (m, 2H), 0.96 (t, 3H, J=7.3 Hz).

Step 3: Resin IX (R$^5$=n-Pr)

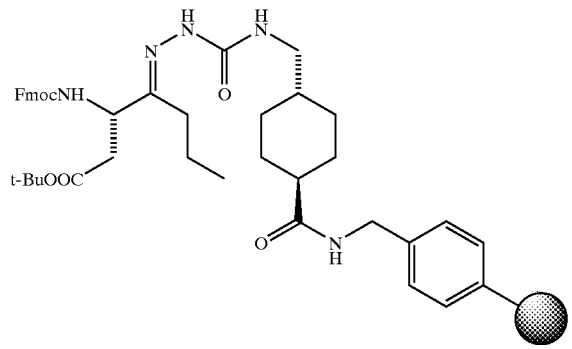

Following the procedure of Example 1, step 4, the title resin was obtained.

Step 4: (3S)-3-((2S)-2-[((2S)-2-[(2S)-2-(Acetylamino)-3-carboxypropanoyl]amino-4-carboxybutanoyl)amino]-3-methylbutanoylamino)-4-oxoheptanoic acid (SEQ ID NO 5)

(SEQ ID NO 5)

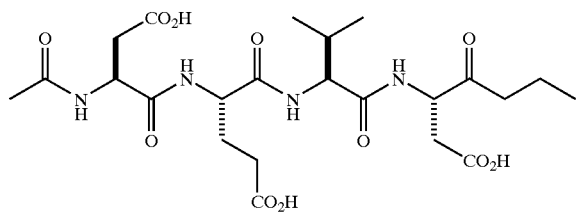

Following the procedure of Example 1, step 5, the title compound was obtained: $^1$H NMR (400 MHz, CD$_3$OD) δ4.68 (t, 1H, J=6.7 Hz), 4.63 (t, 1H, J=6.3 Hz), 4.37 (dd, 1H, J=5.0, 9.1 Hz), 4.14 (d, 1H, J=7.2 Hz),), 2.86 (dd, 1H, J=6.4, 16.9 Hz), 2.85 (dd, 1H, J=6.2, 16.9 Hz), 2.72 (dd, 1H, J=7.0, 17.0 Hz), 2.68 (dd, 1H, J=6.4, 18.2 Hz), 2.34–2.54 (m, 4H), 2.08–2.16 (m, 2H), 1.99 (s, 3H), 1.90–1.99 (m, 1H), 1.51–1.58 (m, 2H), 0.96 (d, 6H, J=6.7 Hz), 0.89 (d, 3H, J=7.4 Hz); MS (-APCI) m/z 543 (M-H)$^-$.

EXAMPLE 6

(3S)-3-((2S)-2-[((2S)-2-[(2S)-2-(Acetylamino)-3-carboxypropanoyl]amino-4-carboxybutanoyl)amino]-3-methylbutanoylamino)-4-oxo-6-phenylhexanoic acid (SEQ ID NO 6)

Step 1: tert-Butyl (3S)-3-[(9H-9-fluorenylmethoxy)carbonyl]amino-4-oxo-6-phenylhexanoate

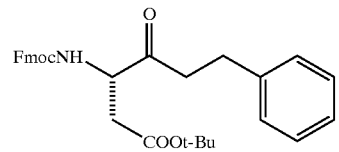

Following the procedure of Example 1, Step 2, substituting phenylpropylmagnesium bromide for phenylethylmagnesium bromide, the title compound was obtained: $^1$H NMR (400 MHz, CD$_3$COCD$_3$) δ7.84 (d, 2H, J=7.6 Hz), 7.18 (d, 2H, J=7.6 Hz), 7.37 (t, 2H, J=7.5 Hz), 7.14–7.32 (m, 7H), 6.87 (d, 1H, J=8.2 Hz), 4.49–4.58 (m, 1H), 4.35–4.46 (m, 3H), 4.23 (t, 1H, J=6.9 Hz), 2.74–3.02 (m, 5H), 2.66 (dd, 1H, J=7.0, 16.1 Hz), 1.41 (s, 9H).

Step 2: 4-[([2-((E,2S)-4-(tert-Butoxy)-2-[(9H-9-fluorenylmethoxy)carbonyl]amino-4-oxo-1-phenethylbutylidene)hydrazino]carbonylamino)methyl]-1-cyclohexanecarboxylic acid

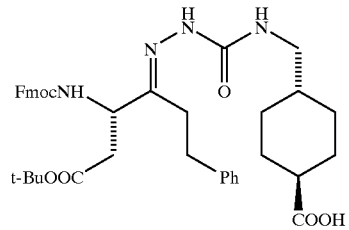

Following the procedure of Example 1, step 3, the title compound was obtained: $^1$H NMR (400 MHz, CD$_3$COCD$_3$) δ9.94 (s, 1H), 7.82 (d, 2H, J=7.6 Hz), 7.67 (t, 2H, J=7.2 Hz), 7.10–7.39 (m, 9H), 6.75–6.80 (m, 2H), 4.85–4.91 (m, 1H), 4.38–4.47 (m, 2H), 4.22 (brt, 1H, J=6.8 Hz), 3.04–3.16 (m, 2H), 2.72–2.92 (m, 2H), 2.54–2.73 (m, 2H), 2.23 (brt, 1H, J=12.1 Hz), 2.02–2.05 (m, 2H), 1.84 (brd, 2H, J=12.2 Hz), 1.14–1.50 (m, 14H), 0.97–1.03 (m, 2H).

Step 3: Resin IX ($R^5$=2-phenylethyl)

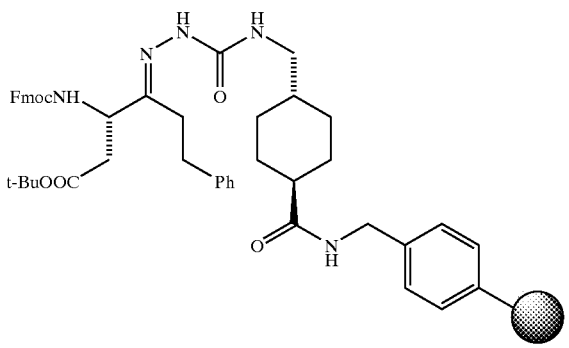

Following the procedure of Example 1, step 4, the title resin was obtained.

Step 4: (3S)-3-((2S)-2-[((2S)-2-[(2S)-2-(Acetylamino)-3-carboxypropanoyl]amino-4-carboxybutanoyl]amino]-3-methylbutanoylamino)-4-oxo-6-phenylhexanoic acid (SEQ ID NO 6)

(SEQ ID NO 6)

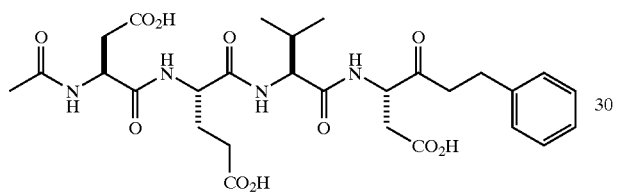

Following the procedure of Example 1, step 5, the title compound was obtained: 1H NMR (400 MHz, $CD_3OD$) δ8.25 (d, 1H, J=7.2 Hz), 7.85 (d, 1H, J=8.1 Hz), 7.11–7.25 (m, 5H), 4.67 (t, 1H, J=6.7 Hz), 4.62 (t, 1H, J=6.4 Hz), 4.31–4.36 (m, 1H) 4.13 (t, 1H, J=7.4 Hz), 2.64–2.95 (m, 8H), 2.32–2.43 (m, 2H), 2.06–2.14 (m, 2H), 1.98 (s, 3H), 1.89–1.97 (m, 1H), 0.93 (d, 6H, J=6.8 Hz); MS (–APCI) m/z 606 (M–H)$^-$.

EXAMPLE 7

(3S)-3-((2S)-2-[((2S)-2-[(2S)-2-(Acetylamino)-3-carboxypropanoyl]amino-4-carboxybutanoyl)amino]-3-methylbutanoylamino)-4-oxo-8-phenyloctanoic acid (SEQ ID NO 7)

Step 1: tert-Butyl (3S)-3-[(9H-9-fluorenylmethoxy)carbonyl]amino-4-oxo-8-phenyloctanoate

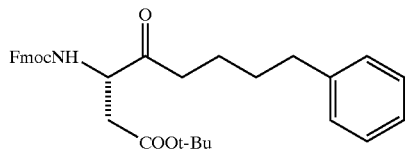

Following the procedure of Example 1, Step 2, substituting phenylpropylmagnesium bromide for phenylbutylmagnesium bromide, the title compound was obtained: $^1$H NMR (400 MHz, $CD_3COCD_3$) δ7.84 (d, 2H, J=7.5 Hz), 7.68 (d, 2H, J=7.4 Hz), 7.11–7.46 (9H, m), 6.80 (brd, 1H, J=7.9 Hz), 4.32–4.55 (m, 3H), 4.24 (t, 1H, J=6.7 Hz), 2.33–2.84 (m, 6H), 1.23–1.63 (m, 4H), 1.40 (s, 9H).

Step 2: 4-[(2-[(E)-1-((1S)-3-(tert-Butoxy)-1-[(9H-9-fluorenylmethoxy)carbonyl]amino-3-oxopropyl)-5-phenylpentylidene]hydrazinocarbonyl)amino]methyl-1-cyclohexanecarboxylic acid

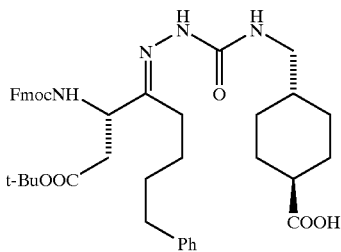

Following the procedure of Example 1, step 3, the title compound was obtained: $^1$H NMR (400 MHz, $CD_3COCD_3$) δ9.06 (s, 1H), 7.85 (d, 2H, J=7.4 Hz), 7.69 (d, 2H, J=7.4 Hz), 7.40 (t, 2H, J=7.5 Hz), 7.31 (t, 2H, J=7.5 Hz), 7.09–7.24 (m, 5H), 6.72 (d, 1H, J=9.2 Hz), 6.61 (brt, 1H, J=6.6 Hz), 4.70–4.83 (m, 1H), 4.31–4.44 (m, 2H), 4.23 (brt, 1H, J=7.0 Hz), 2.98–3.17 (m, 2H), 2.43–2.88 (m, 5H), 2.13–2.42 (m, 2H), 1.95–2.05 (m, 2H), 1.87 (brd, 2H, J=10.4 Hz), 1.30–1.68 (m, 5H), 1.40 (s, 9H), 0.95–1.10 (m, 2H).

Step 3: Resin IX ($R^5$=4-phenylbut-1-yl)

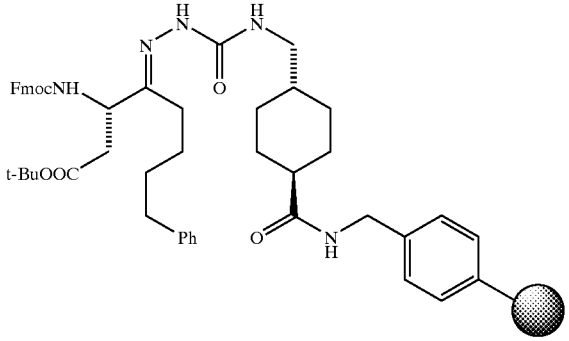

Following the procedure of Example 1, step 4, the title resin was obtained.

Step 4: (3S)-3-((2S)-2-[((2S)-2-[(2S)-2-(Acetylamino)-3-carboxypropanoyl]amino-4-carboxybutanoyl)amino]-3-methylbutanoylamino)-4-oxo-8-phenyloctanoic acid (SEQ ID NO 7)

(SEQ ID NO 7)

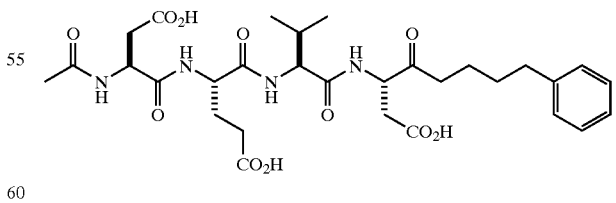

Following the procedure of Example 1, step 5, the title compound was obtained: $^1$H NMR (400 MHz, $CD_3OD$) δ8.27 (d, 1H, J=7.3 Hz), 7.85 (d, 1H, J=8.0 Hz), 7.08–7.17 (m, 5H), 4.67 (t, 1H, J=6.6 Hz), 4.63 (t, 1H, J=6.4 Hz), 4.31–4.40 (m, 1H), 4.14 (t, 1H, J=7.9 Hz), 2.79–2.90 (m, 2H), 2.49–2.76 (m, 6H), 2.30–2.45 (m, 2H), 2.06–2.19 (m, 2H), 1.98 (s, 3H), 1.86–1.98 (m, 1H), 1.47–1.64 (m, 4H), 0.95 (d, 6H, J=6.8 Hz); MS (–APCI) m/z 634 (M–H)⁻.

EXAMPLE 8

(3S)-3-((2S)-2-[((2S)-2-[(2S)-2-(Acetylamino)-3-carboxypropanoyl]amino-4-carboxybutanoyl)amino]-3-methylbutanoylamino)-4-oxo-5-phenylpentanoic acid (SEQ ID NO 8)

Step 1: tert-Butyl (3S)-3-[(9H-9-fluorenylmethoxy)carbonyl]amino-4-oxo-5-phenylpentanoate

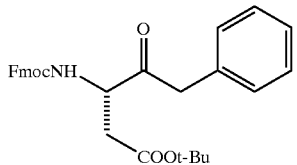

Following the procedure of Example 1, Step 2, substituting phenylpropylmagnesium bromide for benzylmagnesium bromide, the title compound was obtained; ¹H NMR (400 MHz, CD₃COCD₃) δ7.85 (d, 2H, J=7.4 Hz), 7.71 (d, 2H, J=7.5 Hz), 7.10–7.46 (m, 9H), 6.87 (brd, 1H, J=7.7 Hz), 4.52–4.65 (m, 1H), 4.38–4.50 (m, 2H), 4.26 (m, 1H, J=6.9 Hz), 2.72–2.87 (m, 3H), 2.65 (dd, 1H, J=6.7, 16.2Hz), 1.39 (s, 9H).

Step 2: 4-[([2-((E,2S)-1-Benzyl-4-(tert-butoxy)-2-[(9H-9-fluorenylmethoxy)carbonyl]amino-4-oxobutylidene)hydrazino]carbonylamino)methyl]-1-cyclohexanecarboxylic acid

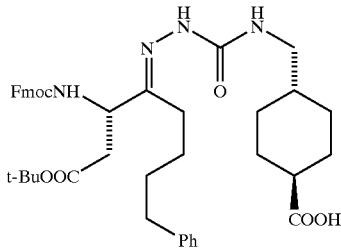

Following the procedure of Example 1, step 3, the title compound was obtained: ¹H NMR (400 MHz, CD₃COCD₃) δ8.93 (s, 1H), 7.85 (d, 2H, J=8.2 Hz), 7.68 (t, 2H, J=6.5 Hz), 7.40 (t, 2H, J=7.4 Hz), 7.09–7.35 (m, 7H), 6.76 (d, 1H, J=9.6 Hz), 6.61 (t, 1H, J=5.6 Hz), 4.80–4.86 (m, 1H), 4.33–4.45 (m, 2H), 4.22 (t, 1H, J=7.0 Hz), 3.99 (d, 1H, J=15.3 Hz), 3.64 (t, 1H, J=15.5 Hz), 3.01–3.15 (m, 2H), 2.65–2.83 (m, 2H), 2.61 (dd, 1H, J=5.7, 14.8 Hz), 2.16–2.28 (m, 1H), 1.93–2.04 (m, 2H), 1.80–1.89 (m, 2H), 1.27–1.53 (m, 2H), 1.31 (s, 9H), 0.95–1.09 (m, 2H).

Step 3: Resin IX (R⁵=benzyl)

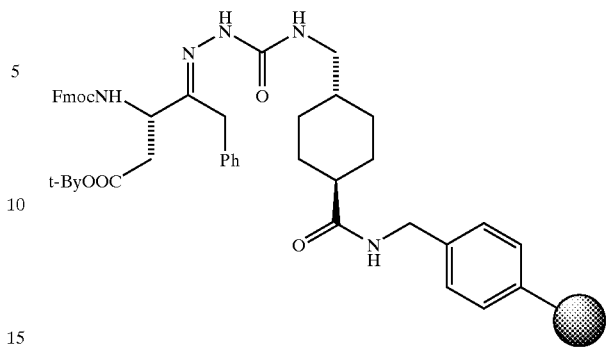

Following the procedure of Example 1, step 4, the title resin was obtained.

Step 4: (3S)-3-((2S)-2-[((2S)-2-[(2S)-2-(Acetylamino)-3-carboxypropanoyl]amino-4-carboxybutanoyl)amino]-3-methylbutanoylamino)-4-oxo-5-phenylpentanoic acid (SEQ ID NO 8)

(SEQ ID NO 8)

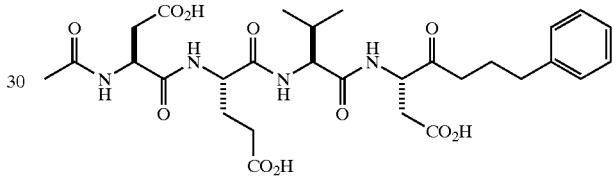

Following the procedure of Example 1, step 5, the title compound was obtained: ¹H NMR (400 MHz, CD₃OD) δ7.91 (d, 1H, J=7.3 Hz), 7.15–7.19 (m, 5H), 4.62–4.69 (m, 2H), 4.35–4.42 (m, 1H), 4.11–4.17 (m, 1H), 3.96 (brs, 2H), 2.81–2.90 (m, 2H), 2.64–2.76 (m, 2H), 2.36–2.45 (m, 2H), 2.07–2.20 (m, 2H), 1.98 (s, 3H), 1.89–2.00 (m, 1H), 0.96 (d, 6H, J=6.8 Hz); MS (–APCI) m/z 591 (M–H)⁻.

EXAMPLE 9

(3S)-3-((2S)-2-[((2S)-2-[(2S)-2-(Acetylamino)-3-carboxypropanoyl]amino-4-carboxybutanoyl)amino]-3-methylbutanoylamino)-7-(4-methoxyphenyl)-4-oxoheptanoic acid (SEQ ID NO 9)

Step 1: tert-Butyl (3S)-3-[(9H-9-fluorenylmethoxy)carbonyll amino-7-(4-methoxyphenyl)-4-oxoheptanoate (SEQ ID NO 9)

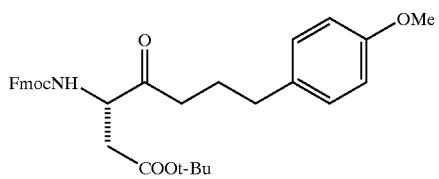

Following the procedure of Example 1, Step 2, substituting phenylpropylmagnesium bromide for 4-methoxyphenylpropylmagnesium bromide, the title compound was obtained: ¹H NMR (400 MHz, CD₃COCD₃)

δ 7.85 (d, 2H, J=7.5 Hz), 7.69 (d, 2H, J=7.5 Hz), 7.41 (t, 2H, J=7.3 Hz), 7.32 (t, 2H, J 7.5 Hz), 7.08 (d, 2H, J=8.6 Hz), 6.82 (brd, 1H, J=8.4 Hz), 6.78 (d, 2H, J=8.6 Hz), 4.32–4.50 (m, 3H), 4.24 (t, 1H, J=6.9 Hz), 2.77–2.82 (m, 1H), 2.48–2.66 (m, 5H), 1.79–1.86 (m, 2H), 1.41 (s, 9H).

Step 2: 4-([[(2-(E,2S)-4-(tert-Butoxy)-2-[(9H-9-fluorenylmethoxy)carbonyl]amino-1-(3-(4-methoxyphenyl)propyl]-4-oxobutylidenehydrazino)carbonyl]aminomethyl)-1-cyclohexanecarboxylic acid

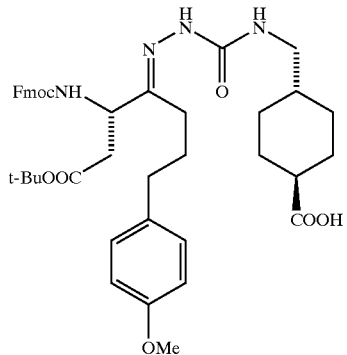

Following the procedure of Example 1, step 3, the title compound was obtained: ¹H NMR (400 MHz, CD₃COCD₃) δ 9.81 (s, 1H), 7.84 (d, 2H, J=7.6 Hz), 7.68 (t, 2H, J=7.6 Hz), 7.40 (t, 2H, J=7.4 Hz), 7.30 (t, 2H, J=7.4 Hz), 7.08 (d, 2H, J=7.4 Hz), 6.65–6.80 (m, 4H), 4.75–4.85 (m, 1H), 4.32–4.44 (m, 2H), 4.21 (brt, 1H, J=7.0 Hz), 3.67 (s, 3H), 3.09–3.22 (m, 2H), 2.33–2.79 (m, 6H), 2.16–2.28 (m, 1H), 1.95–2.05 (m, 2H), 1.70–1.80 (m, 2H), 1.30–1.55 (m, 5H), 1.38 (s, 9H), 0.98–1.10 (m, 2H).

Step 3: Resin IX (R⁵=3-(p-OMe)-phenylprop-1-yl)

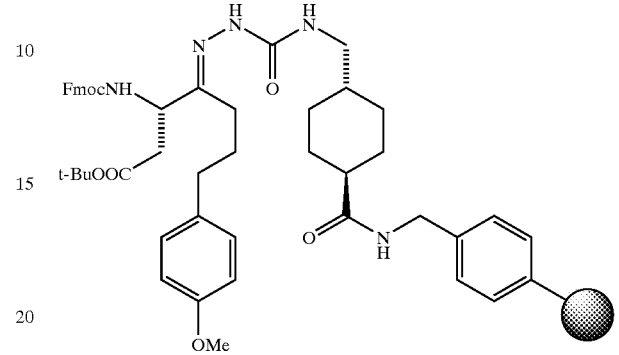

Following the procedure of Example 1, step 4, the title resin was obtained.

Step 4: (3S)-3-((2S)-2-[((2S)-2-[(2S)-2-(Acetylamino)-3-carboxypropanoyl]amino-4-carboxybutanoyl)amino]-3-methylbutanoylamino)-7-(4-methoxyphenyl)-4-oxoheptanoic acid (SEQ ID NO 9)

(SEQ ID NO 9)

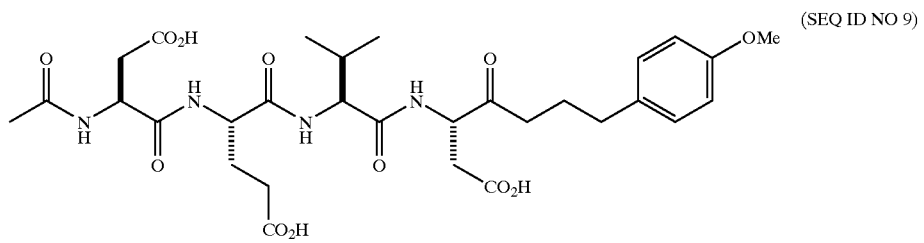

Following the procedure of Example 1, step 5, the title compound was obtained: ¹H NMR (400 MHz, CD₃OD) δ 8.25 (d, 1H, J=6.7 Hz), 7.84 (d, 1H, J=8.0 Hz), 7.06 (d, 2H, J=8.2 Hz), 6.79 (d, 2H, J=8.4 Hz), 4.66 (t, 1H, J=6.2 Hz), 4.60 (t, 1H, J=6.3 Hz), 4.32–4.40 (m, 1H), 4.12 (brt, 1H, J=7.2 Hz), 3.72 (s, 1H), 2.30–2.90 (m, 10H), 2.03–2.18 (m, 2H), 1.85–2.00 (m, 1H), 1.97 (s, 3H), 1.72–1.85 (m, 2H), 0.92 (d, 6H, J=6.6 Hz); MS (−APCI) m/z 650 (M−H)⁻.

EXAMPLE 10

(3S)-3-((2S)-2-[((2S)-2-[(2S)-2-(Acetylamino)-3-carboxypropanoyl]amino-4-carboxybutanoyl)amino]-3-methylbutanoylamino)-7-(1-naphthyl)-4-oxoheptanoic acid (SEQ ID NO 10)

Step 1: tert-Butyl (3S)-3-[(9H-9-fluorenylmethoxy)carbonyl]amino-7-(1-naphthyl)-4-oxoheptanoate

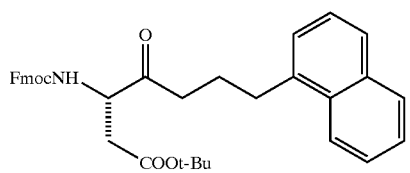

Following the procedure of Example 1, Step 2, substituting phenylpropylmagnesium bromide for 1-naphthylpropylmagnesium bromide, the title compound was obtained: $^1$H NMR (400 MHz, CD$_3$COCD$_3$) δ8.16 (d, 1H, J=8.4 Hz), 7.84–7.88 (m, 3H), 7.68–7.73 (m, 3H), 7.29–7.53 (m, 8H), 6.87 (d, 1H, J=8.4 Hz), 4.51–4.57 (m, 1H), 4.37–4.47 (m, 2H), 4.23 (t, 1H, J=6.8 Hz), 3.05–3.09 (m, 2H), 2.64–2.87 (m, 4H), 1.96–2.03 (m, 2H), 1.41 (s, 9H).

Step 2: 4-([[(2-(E,2S)-4-(tert-Butoxy)-2-[(9H-9-fluorenylmethoxy)carbonyl]amino-1-[3-(1-naphthyl)propyl]-4-oxobutylidenehydrazino)carbonyl]aminomethyl)-1-cyclohexanecarboxylic acid

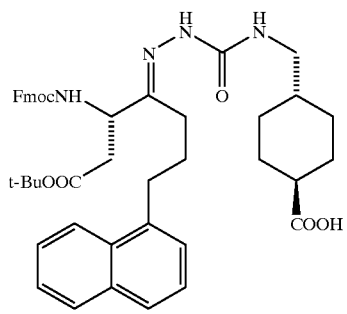

Following the procedure of Example 1, step 3, the title compound was obtained: $^1$H NMR (400 MHz, CD$_3$COCD$_3$) δ9.97 (s, 1H), 8.17 (d, 1H, J=8.2 Hz), 7.81–7.84 (m, 3H), 7.81–7.84 (m, 3H), 7.25–7.50 (m, 8H), 6.73–6.81 (m, 2H), 4.80–4.90 (m, 1H), 4.30–4.42 (m, 2H), 4.18 (brt, 1H, J=7.0 Hz), 3.07–3.27 (m, 4H), 2.53–2.79 (m, 3H), 2.14–2.27 (m, 1H), 1.91–2.02 (m, 2H), 1.75–1.88 (m, 2H), 1.23–1.55 (m, 4H), 1.98 (s, 9H), 0.80–1.55 (m, 3H).

Step 3: Resin IX (R$^5$=3-(1-naphthyl)prop-1-yl)

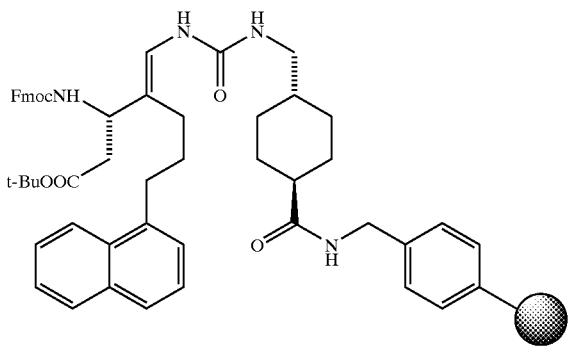

Following the procedure of Example 1, step 4, the title resin was obtained.

Step 4: (3S)-3-((2S)-2-[((2S)-2-[(2S)-2-(Acetylamino)-3-carboxypropanoyl]amino-4-carboxybutanoyl)amino]-3-methylbutanoylamino)-7-(1-naphthyl)-4-oxoheptanoic acid (SEQ ID NO 10)

(SEQ ID NO 10)

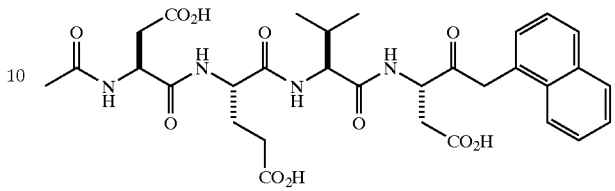

Following the procedure of Example 1, step 5, the title compound was obtained: $^1$H NMR (400 MHz, CD$_3$OD) δ8.12 (d, 1H, J=8.1 Hz), 7.86 (d, 1H, J=8.1 Hz), 7.82 (d, 1H, J=7.7 Hz), 7.68 (d, 1H, J=8.1 Hz), 7.31–7.50 (m, 4H), 4.60–4.70 (m, 2H), 4.35 (dd, 1H, J=4.7, 8.9 Hz), 4.14 (brt, 1H, J=7.9 Hz), 3.00–3.08 (m, 2H), 2.83–2.92 (m, 2H), 2.55–2.78 (m, 4H), 2.35–2.45 (m, 2H), 2.07–2.19 (m, 2H), 1.90–2.03 (m, 5H), 0.94 (d, 6H, J=6.8 Hz); MS (−APCI) m/z 670 (M−H)$^-$.

EXAMPLE 100

(3S)-3-((2S)-2-[((2S)-2-[(2S)-2-(Acetylamino)-3-carboxypropanoyl]aminopropanoyl)amino]-3-methylbutanoylamino)-4-oxo-7-phenylheptanoic acid (SEQ ID NO 12)

(SEQ ID NO 12)

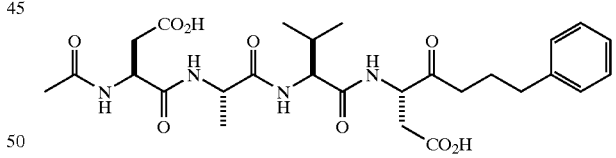

Using the resin from Example 1, Step 4, and substituting Fmoc-L-Glu(OtBu)-OH for Fmoc-L-Ala-OH(1.56 g) in Step 5, the title compound was obtained as colorless solid: $^1$H NMR (400 MHz, CD$_3$OD) δ8.32 (d, 1H, J=7.20 Hz), 7.82 (d, 1H, J=8.12 Hz), 7.30–7.10 (m, 5H), 4.68 (t, 1H, J=6.70 Hz), 4.63 (t, 1H, J=6.21 Hz), 4.30–4.10 (m, 1H), 4.13 (brt, 1H, J=7.62 Hz), 2.91–2.80 (m, 2H), 2.75–2.45 (m, 6H), 2.20–2.05 (m, 1H), 1.97 (s, 3H), 1.90–1.78 (m, 2H), 1.37 (d, 3H, J=7.20 Hz), 0.94 (d, 6H, J=6.80 Hz); MS (+APCI) m/z 563 (M+H)$^+$.

EXAMPLE 101

(3S)-3-((2S)-2-[((2S)-2-[(2S)-2-(Acetylamino)-3-carboxypropanoyl]aminopropanoyl)amino]-3-methylbutanoylamino)-4-oxo-9-phenylnonanoic acid
(SEQ ID NO 13)

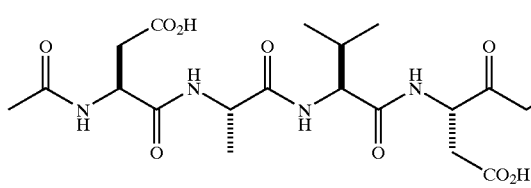

(SEQ ID NO 13)

Using the resin from Example 3, Step 3, and following the procedure of Example 1, Step 5, substituting Fmoc-L-Glu (OtBu)-OH for Fmoc-L-Ala-OH (1.56 g), the title compound was obtained as a colorless solid: $^1$H NMR (400 MHz, CD$_3$OD) δ8.27 (d, 1H, J=6.1 Hz), 7.78 (d, 1H, J=8.4 Hz), 7.09–7.24 (m, 5H), 4.68 (t, 1H, J=6.7 Hz), 4.64 (t, 1H, J=6.3 Hz), 4.27–4.31 (m, 1H), 4.13 (t, 1H, J=7.9 Hz), 2.42–2.90 (m, 8H), 2.08–2.19 (m, 1H), 1.97 (s, 3H), 1.53–1.66 (m, 4H), 1.25–1.38 (m, 2H), 1.36 (d, 3H, J=7.2 Hz), 0.95 (d, 6H, J=7.8 Hz); MS (−APCI) m/z 590 (M−H)$^-$.

EXAMPLE 102

(3S)-3-[((2S)-2-[(2S)-2-((2S)-3-Carboxy-2-[(3,5-dibromobenzoyl)amino]propanoylamino)propanoyl]amino-3-methylbutanoyl)amino]-4-oxo-7-phenylheptanoic acid (SEQ ID NO 14)

O-(7-azabenzotriazol-1-yl)N,N,N',N'-tetramethyluronium hexafluorophosphate (HATU) and N,N-diisopropylethylamine (DIEA) were used as coupling reagents instead of TBTU and HOBt as described in the user's guide.

b) Cleavage from Solid Support

The above polymer was transferred into a fritted reaction vessel and treated with TFA/H$_2$O (9:1, 2 mL) and agitated for 30 min. The solution was filtered, the solid support was washed with TFA (2×0.5 mL) and the filtrate was evaporated. Trituration from Et$_2$O gave 83 mg of the title compound as a colorless solid: $^1$H NMR (400 MHz, DC$_3$D) δ8.01 (d, 2H, J=1.67 Hz), 7.90 (t, 1H, 1.69 Hz), 7.81 (d, 1H, J=7.85 Hz), 7.28–7.05 (m, 5H), 4.87 (t, 1H, J=6.30 Hz) 4.63 (t, 1H, J=6.20 Hz), 4.40–4.30 (m, 1H), 4,18–4.10 (m, 1H), 3.00 (dd, 1H, 6.12, 16.88 Hz), 2.90–2.78 (m, 2H), 2.75–2.45 (m, 5H), 2.20–2.05 (m, 1H), 1.90–1.78 (m, 2H), 1.38 (d, 3H, J=7.18 Hz), 0.94 (d, 6H, J=6.73 Hz); MS (+APCI) m/z 783 (M+H)$^+$.

(SEQ ID NO 14)

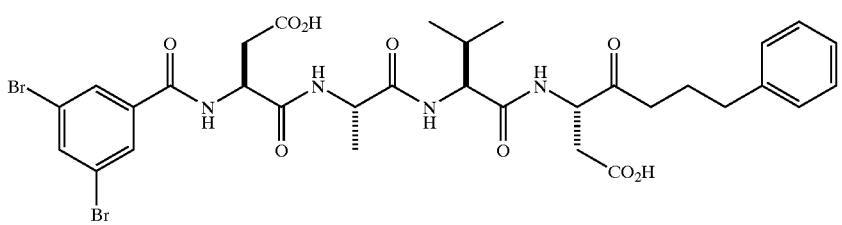

a) Preparation of the Tetrapeptide on Solid Support

Using the resin from Example 1, Step 4, and following the procedure given in the 9050 PepSynthesizer user's guide, the tetrapeptide was prepared with the following reagents: 290 mg of polymer (0.7 meq/g loading), 3,5-dibromobenzoic acid (1.44 g), Fmoc-L-Val-OH (1.65g,), Fmoc-Ala-OH (1.59 g), Fmoc-L-Asp (OtBu)-OH (1.80 g);

EXAMPLE 103

(3S)-3-[((2S)-2-[(2S)-2-((2S)-3-Carboxy-2-[(3,5-dideuteriobenzoyl)amino]propanoylamino)propanoyl]amino-3-methylbutanoyl)amino]-4-oxo-7-phenylheptanoic acid (SEQ ID NO 15)

(SEQ ID NO 15)

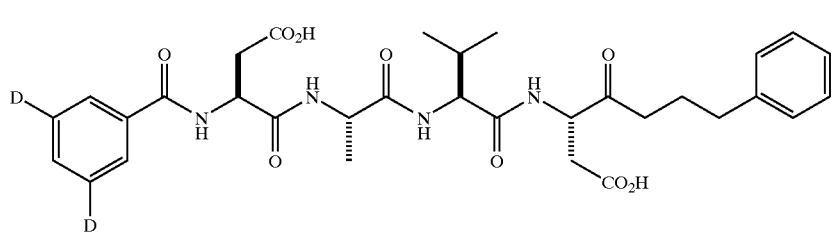

To the peptide from Example 103 (10 mg, 12.8 μmol) in 2 mL MeOH and 0.5 mL NEt₃ was added Pd/C (10%, 2 mg) and the mixture was stirred under a D₂-balloon for 20 h. The mixture was filtered through a pad of Celite, rinsed with MeOH, and evaporated to give 10 mg (100%) of the title compound: 1H NMR (400 MHz, CD₃OD) δ7.85 (s, 2H), 7.50 (s, 1H), 7.25–7.05 (m, 5H), ~4.8 (m, 1H, signal obstructed by CD₃OD), 4.60 (t, 1H), 4.38–4.30 (m, 1H), 4.18–4.08 (m, 1H), 2.90–2.45 (m, 8H), 2.21–2.08 (m, 1H), 1.85–1.72 (m, 2H), 1.40 (d, 3H), 0.95 (d, 6H); MS (–APCI) m/z 626 (M–H)⁻.

EXAMPLE 104

(3S)-3-((2S)-2-[((2S)-2-[(2S)-2-Amino-4-methoxy-4-oxobutanoyl]aminopropanoyl)amino]-3-methylbutanoylamino)-4-oxo-7-phenylheptanoic acid (SEQ ID NO 16)

a) Preparation of the Tetrapeptide on Solid Support

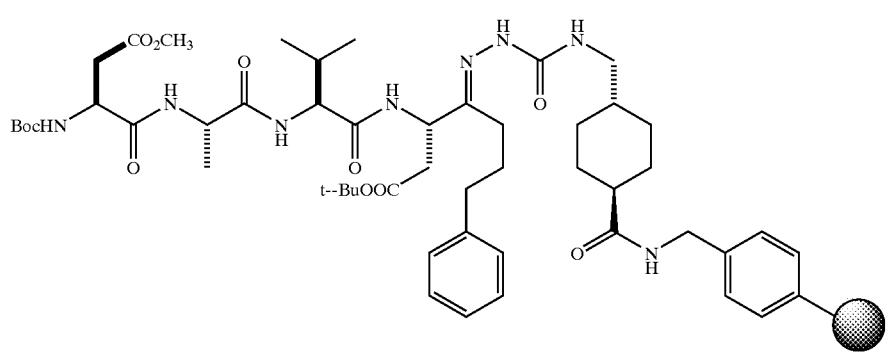

Using the resin from Example 1, Step 4, and following the procedure given in the 9050 PepSynthesizer users guide, the tetrapeptide was prepared with the following reagents: 290 mg of polymer (0.7 meq/g loading), t-Boc-L-Asp (OCH₃)—OH (1.79 g), Fmoc-L-Ala-OH (1.59 g), Fmoc-L-Val-OH (1.65 g), O-(7-azabenzotriazol-1-yl)N,N,N',N'-tetramethyluronium hexafluorophosphate (HATU) and N,N-diisopropylethylamine (DIEA) were used as coupling reagents instead of TBTU and HOBt as described in the user's guide.

b) Cleavage from Solid Support

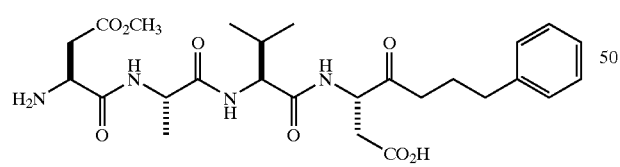

The above polymer was transferred into a fritted reaction vessel and treated with TFA/H₂O (9:1, 2 mL) and agitated for 30 min. The solution was filtered, the solid support was washed with TFA (2×0.5 mL) and the filtrate was evaporated. Trituration from Et₂O gave 71 mg of the title compound as a colorless solid: ¹H NMR (400 MHz, CD₃OD) δ7.89 (d, 1H, J=7.87 Hz), 7.28–7.08 (m, 5H), 4.59 (t, 1H, J=6.12 Hz), 4.45–4.35 (m, 1H), 4.25–4.10 (m, 2H), 3.73 (s, 3H,), 3.15–3.02 (m, 1H), 2.92–2.78 (m, 2H), 2.75–2.45 (m, 5H), 2.15–2.00 (m, 1H), 1.88–1.78 (m, 2H), 1.36 (d, 3H, J=7.16 Hz), 0.92 (2d, 6H, J=6.73 Hz); MS (+APCI) m/z 535 (M+H)⁺.

EXAMPLE 105

(3S)-3-((2S)-2-[((2S)-2-[(2S)-2-(Acetylamino)-4-methoxy-4-oxobutanoyl]aminopropanoyl)amino]-3-methylbutanoylamino)-4-oxo-7-phenylheptanoic acid (SEQ ID NO 26)

(SEQ ID NO 26)

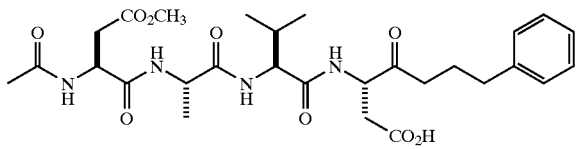

To the peptide from Example 104 (25 mg, 47 μmol) in 400 μΛ THF was added NaHCO₃ (39.5 mg in 500 μΛ H₂O) and acetyl chloride (33.5 μΛ in 500 μΛ THF). The mixture was stirred for 16 h and then poured into sat. aq. NH₄Cl. The layers were separated and the aqueous layer was extracted with EtOAc. The combined organic layers were dried over MgSO₄, filtered and evaporated. The crude material was triturated with Et₂O to give 17 mg (63%) of the product as a colorless solid: ¹H NMR (400 MHz, CD₃OD) δ7.30–7.08 (m, 5H), 4.70 (t, 1H, J=6.76 Hz), 4.62 (t, 1H, J=6.12 Hz), 4.35–4.25 (m, 1H), 4.19–4.10 (m, 1H), 3.67 (s, 3H), 2.95–2.45 (m, 8H), 2.20–2.05 (m, 1H), 1.96 (s, 3H), 1.90–1.78 (m, 2H), 1.37 (d, 3H, J=7.17 Hz), 0.94 (d, 6H, J=6.77 Hz); MS (+APCI) m/z 577 (M+H)⁺.

EXAMPLE 106

(3S)-3-((2S)-2-[((2S)-2-[(2S)-2-(Acetylamino)-3-carboxypropanoyl]aminopropanoyl)amino]-3-methylbutanoylamino)-7-(1-naphthyl)-4-oxoheptanoic acid (SEQ ID NO 17)

(SEQ ID NO 17)

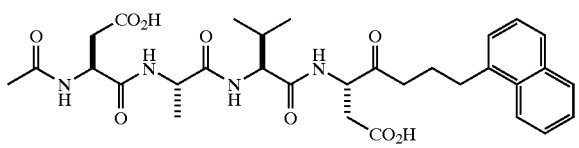

Using the resin from Example 10, Step 3, and following the procedure of Example 1, Step 5, substituting Fmoc-L-Glu(OtBu)-OH for Fmoc-L-Ala-OH (1.56 g), the title compound was obtained as a colorless solid: $^1$H NMR (400 MHz, CD$_3$OD) δ8.27 (d, 1H, J=6.2 Hz), 8.12 (d, 1H, J=8.3 Hz), 7.82 (d, 1H, J=8.0 Hz), 7.79 (d, 1H, J=7.9 Hz), 7.69 (d, 1H, J=8.0 Hz), 7.31–7.50 (m, 4H), 4.61–4.70 (m, 2H), 4.25–4.35 (m, 1H), 4.14 (brt, 1H, J=7.2 Hz), 3.02–3.09 (m, 2H), 2.83–2.92 (m, 2H), 2.53–2.80 (m, 4H), 2.05–2.18 (m, 2H), 1.92–2.02 (m, 4H), 1.37 (d, 2H, J=7.2 Hz), 0.94 (d, 6H, J=6.8 Hz); MS (−APCI) m/z 612 (M−H)$^-$.

EXAMPLE 107

(3S)-3-[((2S)-2-[(2S)-2-((2S)-3-Carboxy-2-[(4-iodobenzoyl)amino]propanoylamino)propanoyl]amino-3-methylbutanoyl)amino]-4-oxo-7-phenylheptanoic acid (SEQ ID NO 18)

(SEQ ID NO 18)

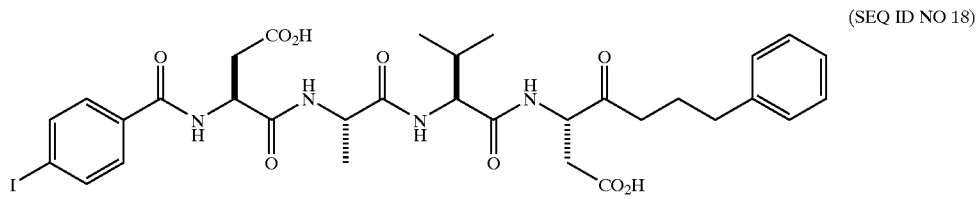

a) Preparation of the Tetrapeptide on Solid Support

Using the resin from Example 1, Step 4, and following the procedure given in the 9050 PepSynthesizer user's guide, the tetrapeptide was prepared with the following reagents: 290 mg of polymer (0.7 meq/g loading), 4-iodobenzoic acid (1.28 g), Fmoc-L-Val-OH (1.65g,), Fmoc-Ala-OH (1.59 g), Fmoc-L-Asp (OtBu)-OH (1.80 g); O-(7-azabenzotriazol-1-yl)N,N,N',N'-tetramethyluronium hexafluorophosphate (HATU) and N,N-diisopropylethylamine (DIEA) were used as coupling reagents instead of TBTU and HOBt as described in the user's guide.

b) Cleavage from Solid Support

The above polymer was transferred into a fritted reaction vessel and treated with TFA/H$_2$O (9:1, 2 mL) and agitated for 30 min. The solution was filtered, the solid support was washed with TFA (2×0.5 mL) and the filtrate was evaporated. Trituration from Et$_2$O gave 83 mg of the title compound as a colorless solid: $^1$H NMR (400 MHz, CD$_3$SOCD$_3$) δ8.71 (d, 1H, J=7.3 Hz), 8.41 (d, 1H, J=7.3 Hz), 8.05 (d, 1H, J=7.5 Hz), 7.84 (d, 2H, J=8.4 Hz), 7.74 (d, 1H, J=8.3 Hz), 7.62 (d, 2H, J=8.3 Hz), 7.26–7.13 (m, 5H), 4.85–4.75 (m, 1H), 4.50–4.45 (m, 1H), 4.40–4.28 (m, 1H), 4.18–4.08 (m, 1H), 2.85–2.60 (m, 3H), 2.55–2.35 (m, 5H), 2.00–1.89 (m, 1H), 1.80–1.65 (m, 2H), 1.18 (d, 3H, J=6.9 Hz), 0.81 (d, 3H, J=6.6 Hz), 0.79 (d, 3H, J=6.7 Hz); MS (−APCI) m/z 749 (M−H)$^-$.

EXAMPLE 200

(3S)-3-[((2S)-2-[(2S)-2-[(2S)-2-(Acetylamino)-3-carboxypropanoyl]amino-4-(methylsulfonyl)butanoyl]amino-3-methylbutanoyl)amino]-4-oxo-7-phenylheptanoic acid (SEQ ID NO 19)

(SEQ ID NO 19)

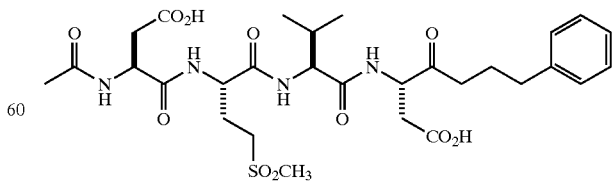

Using the resin from Example 1, Step 4, and substituting Fmoc-L-Glu(OtBu)-OH for Fmoc-L-Met(O2)-OH([1](1.80 g) in Step 5, the title compound was obtained as colorless solid: $^1$H NMR (400 MHz, CD$_3$OD) δ8.23 (d, 1H, J=7.60 Hz), 7.93 (d, 1H, J=7.34 Hz), 7.25–7.05 (m, 5H), 4.68–4.58 (m, 2H), 4.57–4.48 (m, 1H), 4.12 (t, 1H, J=7.47 Hz), 3.25–3.10 (m, 2H), 2.95 (s, 3H), 2.90–2.48 (m, 8H), 2.40–2.28 (m, 1H), 2.20–2.02 (m, 2H), 1.97 (s, 3H), 1.90–1.78 (m, 2H), 0.93 (d, 6H, J=6.57 Hz); MS (–APCI) m/z 653 (M–H)$^-$.

EXAMPLE 201

(3S)-3-((2S)-2-[((2S)-2-[(2R)-2-(Acetylamino)-3-(methylsulfanyl)propanoyl]aminopropanoyl)amino]-3-methylbutanoylamino)-4-oxo-7-phenylheptanoic acid (SEQ ID NO 20)

(SEQ ID NO 20)

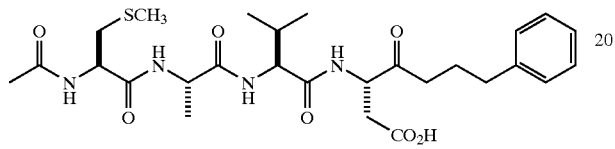

Using the resin from Example 1, Step 4, and substituting Fmoc-L-Asp(OtBu)-OH for Fmoc-L-Cys(SMe)-OH(1.56 g) and Fmoc-L-Glu(OtBu)-OH for Fmoc-L-Ala-OH (1.56 g) in Example 1, Step 5, the title compound was obtained as colorless solid: $^1$H NMR (400 MHz, CD$_3$OD) δ7.76 (d, 1H, J=8.02 Hz), 7.25–7.05 (m, 5H), 4.60 (t, 1H, J=6.03 Hz), 4.51 (t, 1H, J=7.28 Hz), 4.40–4.30 (m, 1H), 4.15 (t, 1H, J=7.56 Hz), 2.96–2.45 (m, 8H), 2.15–2.08 (m, 1H), 2.11 (s, 3H), 1.97 (s, 3H), 1.90–1.88 (m, 2H), 1.35 (d, 3H, J=7.18 Hz), 0.92 (d, 3H, J=6.76 Hz), 0.91 (d, 3H, J=6.74 Hz); MS (–APCI) m/z 563 (M–H)$^-$.

EXAMPLE 202

(3S)-3-((2S)-2-[((2S)-2-[(2R)-2-(Acetylamino)-3-(methylsulfonyl)propanoyl]aminopropanoyl)amino]-3-methylbutanoylamino)-4-oxo-7-phenylheptanoic acid (SEQ ID NO 21)

(SEQ ID NO 21)

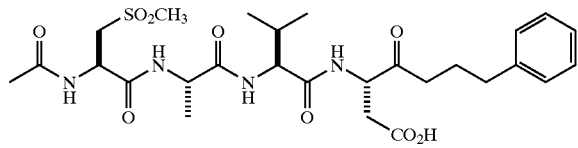

The title compound from Example 201 (20 mg, 0.035 mmol) in 1 mL MeOH at 0oC was treated with OXONE® (22 mg, 0.035 mmol) in 1 mL water. The mixture was allowed to warm to room temperature over 0.5 h and then poured into 30 mL EtOAc. Water was added, the layers were separated, and the aqueous layer was extracted with EtOAc (2×5 mL). The combined organic layers were dried over MgSO4, filtered and evaporated to give 6 mg of the title compound as colorless solid: 1H NMR (400 MHz, CD$_3$OD) 8.14 (d, 1H, J=7.81 Hz), 7.75 (d, 1H, J=7.24 Hz), 7.25–7.05 (m, 5H), 4.94 (t, 1H, J=6.59 Hz), 4.62 (t, 1H, J=6.20 Hz), 4.35–4.20 (m, 1H), 4.15–4.05 (m, 1H), 3.78–3.70 (m, 1H), 3.48–3.38 (m, 1H), 3.29 (s, 3H), 2.88–2.80 (m, 1H), 2.75–2.45 (m, 5H), 2.15–2.03 (m, 1H), 1.97 (s, 3H), 1.90–1.80(m, 2H), 1.37 (d, 3H, J=7.26 Hz), 0.93 (d, 3H, J=6.77 Hz), 0.92 (d, 3H, J=6.74 Hz); MS (–APCI) m/z 595 (M–H)–.

EXAMPLE 203

(3S)-3-((2S)-2-[((2S)-2-[(2R)-2-(Acetylamino)-3-methylsulfanyl)propanoyl]aminopropanoyl)amino]-3-ethylbutanoylamino)-7-(1-naphthyl)-4-oxoheptanoic acid (SEQ ID NO 22)

(SEQ ID NO 22)

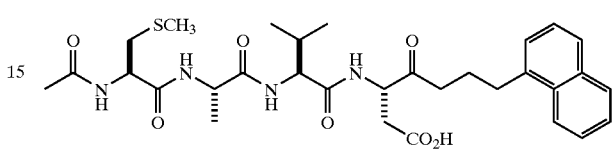

Using the resin from Example 10, Step 3, and substituting Fmoc-L-Asp(OtBu)-OH for Fmoc-L-Cys(SMe)-OH(1.56 g) and Fmoc-L-Glu(OtBu)-OH for Fmoc-L-Ala-OH (1.56 g) in Example 10, Step 4, the title compound was obtained as colorless solid: $^1$H NMR (400 MHz, CD$_3$OD) δ8.38 (d, 1H, J=6.4 Hz), 8.29 (d, 1H, J=8.3 Hz), 8.11 (d, 1H, J=8.0 Hz), 7.82 (d, 1H, J=7.4 Hz), 7.77 (d, 1H, J=8.1 Hz), 7.69 (d, 1H, J=7.9 Hz), 7.31–7.51 (m, 4H), 4.62–4.70 (m, 1H), 4.49–4.57 (m, 1H), 4.32–4.40 (m, 1H), 4.17 (brt, 1H, J=6.8 Hz), 3.01–3.10 (m, 2H), 2.82–2.94 (m, 2H), 2.56–2.76 (m, 4H), 2.05–2.16 (m, 4H), 1.92–2.01 (m, 5H), 1.38 (d, 2H, J=7.2 Hz), 0.93 (dd, 6H, J=3.9, 6.8 Hz); MS (–APCI) m/z 613 (M–H)$^-$.

EXAMPLE 204

(3S)-3-((2S)-2-[((2S)-2-[(2R)-2-(Acetylamino)-3-(methylsulfonyl)propanoyl]aminopropanoyl)amino]-3-methylbutanoylamino)-7-(1-naphthyl)-4-oxoheptanoic acid (SEQ ID NO 23)

(SEQ ID NO 23)

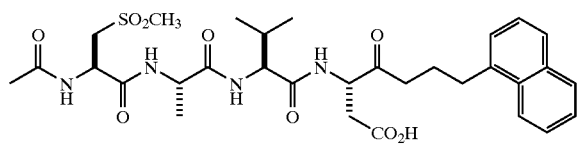

Using the title compound from Example 203, and following the procedure of Example 202, the title compound was obtained: $^1$H NMR (400 MHz, CD$_3$OD) d 8.48 (brd, 1H, J=6.3 Hz), 8.12 (d, 1H, J=8.2 Hz), 7.83 (d, 1H, J=7.8 Hz), 7.76 (d, 1H, J=7.7 Hz), 7.69 (d, 1H, J=8.3 Hz), 7.31–7.51 (m, 4H), 4.95 (t, 1H, J=6.7 Hz), 4.67 (t, 1H, J=6.3 Hz), 4.28–4.31 (m, 1H), 4.14 (brt, 1H, J=7.6 Hz), 3.76 (dd, 1H, J=6.3, 14.7 Hz), 3.41 (dd, 1H, J=7.6, 14.3 Hz), 3.00–3.09 (m, 5H), 2.88 (d, 1H, J=6.0, 16.9 Hz), 2.57–2.80 (m, 3H), 2.05–2.14 (m, 1H), 1.93–2.03 (m, 5H), 1.38 (d, 2H, J=7.2 Hz), 0.93 (d, 6H, J=6.7 Hz); MS (–APCI) m/z 646 (M–H)$^-$.

Assays for Determining Biological Activity (a) Measurement of Caspase Activity by Cleavage of a Fluorogenic Substrate A fluorogenic derivative of the tetrapeptide recognized by caspase-3 and corresponding to the P$_1$ to P$_4$ amino acids of the PARP cleavage site, Ac-DEVD-AMC (AMC, amino-4-methylcoumarin) (SEQ ID NO 11) was prepared as follows:

i) synthesis of N-Ac-Asp(OBn)-Glu(OBn)-Val-CO$_2$H, ii) coupling with Asp(OBn)-7-amino-4-methylcoumarin, iii) removal of benzyl groups.

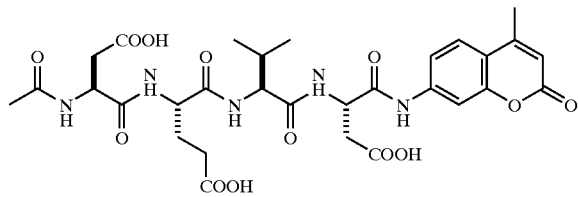

(SEQ ID NO 11)

Standard reaction mixtures (300 μL final volume), contained Ac-DEVD-AMC (SEQ ID NO 11) and purified or crude caspase-3 enzyme in 50 mM Hepes/KOH (pH 7.0), 10% (v/v) glycerol, 0.1% (w/v) CHAPS, 2 mM EDTA, 5 mM dithiothreitol, and were incubated at 25° C. Reactions were monitored continuously in a spectrofluorometer at an excitation wavelength of 380 nm and an emission wavelength of 460 nm.

(b) Cell Death Detection ELISA (Whole Cell Assay)

Colorimetric immunoassay for the qualitative and quantitative in vitro determination of cytoplasmic histone-associated-DNA-fragments (mono-and oligonucleosomes) after induced cell death. This assay was performed using the commercially available kit from Boehringer Mannheim, cat. No. 1 920 685.

c) In Vivo Myocardial Ischemia and Reperfusion Injury in Rats

Male Sprague-Dawley rats (300–400 g) were fasted overnight, and then anesthetized with intraperitoneal administration of sodium pentobarbital (65 mg/kg). To monitor heart rate and aortic pressure the left carotid artery was isolated and a cannula placed in the vessel. The aortic cannula was interfaced with a pressure transducer which was connected to a physiologic recorder. The left jugular vein was isolated and cannulated for administration of a caspase inhibitor compound or vehicle (2% dimethylsulfoxide in 0.9% NaCl). A left thoracotomy was performed in the region overlying the heart and the pericardium opened, exposing the heart. The origin of the left coronary artery was visualized and a 4.0 suture passed under the artery approximately 2–3 mm from its origin. The ends of the suture were passed through a short length of 2 mm id tubing and coronary artery occlusion effected by placing tension on the suture such that the tube compressed the artery. After initial placement of the suture/occluder, the thoracotomy was closed with a small clamp and opened only to effect occlusion and reperfusion of the artery. A Lead II electrocardiograph (ECG) signal was obtained by placing subdermal platinum leads and continuously monitored. After a baseline period of 20–30 minutes the left coronary artery was occluded for 45 minutes. The period of reperfusion was 3 hours. The caspase inhibitor or vehicle was administered as a first bolus 5 minutes before the onset of ischemia and a second bolus was administered again at the onset of reperfusion.

Additionally, an infusion was initiated immediately after the first bolus dose. Control animals received the vehicle alone in equal volumes to the caspase inhibitor treated animals. At the end of reperfusion the animals were euthanized and infarct size determined using a dual staining technique (1.5% w/v triphenyltetrazolium chloride to demarcate infarct tissue and 0.25% w/v Evan's blue to demarcate the area at risk of infarct. The heart was subsequently cut transversely into 4 slices of equal thickness, and infarct size and area at risk quantified using planimetry.

Using the above procedure, it is demonstrated that administration of a caspase inhibitor reduces infarct size in the rat subjected to 45 minutes of regional ischemia and 3 hours of reperfusion.

What is claimed is:

1. A compound of formula I

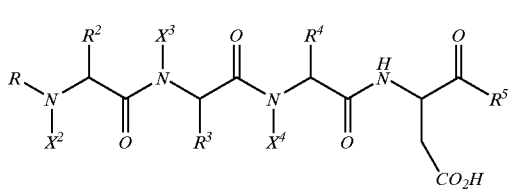

or a salt thereof, wherein:

R is selected from the group consisting of:
  (a) H and
  (b) $C(O)R^1$;

$R^1$ is selected from the group consisting of:
  (a) hydrogen,
  (b) $C_{1-6}$alkoxy,
  (c) $NR^6R^7$,
  (d) benzyloxy or mono- or disubstituted benzyloxy, wherein the substituent is selected from the group consisting of:

73

(1) methyl,
(2) halogen,
(3) methoxy and
(4) cyano,
(e) C$_{1-6}$alkyl or substituted C$_{1-6}$alkyl, wherein the substituent is selected from the group consisting of:
(1) hydroxy,
(2) halo,
(3) C$_{1-3}$alkoxy,
(4) C$_{1-3}$alkylthio.
(5) phenyl C$_{1-3}$alkoxy,
(6) phenyl C$_{1-3}$alkylthio,
(7) phenylcarboxy and
(8) carboxy,
(f) aryl or arylC$_{1-6}$alkyl wherein the aryl group is selected from the group consisting of:
(1) phenyl,
(2) naphthyl.
(3) pyridyl,
(4) furyl.
(5) thienyl,
(6) thiazolyl,
(7) isothiazolyl,
(8) imidazolyl,
(9) benzimidazolyl,
(10) pyrazinyl,
(11) pyrimidyl,
(12) quinolyl,
(13) isoquinolyl,
(14) benzofuryl,
(15) benzothienyl,
(16) pyrazolyl,
(17) indolyl,
(18) purinyl,
(19) isoxazolyl and
(20) oxazolyl, and
(g) mono and di-substituted aryl as defined above in items (1) to (20) of (f), wherein the substituents are independently selected from:
(1) halo,
(2) amino,
(3) nitro,
(4) hydroxy,
(5) cyano,
(6) carboxy,
(7) formyl,
(8) amino carbonyl,
(9) C$_{1-6}$alkyl,
(10) C$_{1-6}$fluoroalkyl,
(11) C$_{1-6}$alkylcarbonyl
(12) C$_{1-6}$alkoxycarbonyl,
(13) C$_{1-6}$alkoxy,
(14) C$_{1-6}$alkylthio,
(15) C$_{1-6}$alkylsulfonyl and
(16) deuterio;
R$^2$ is selected from the group consisting of:
(a) CH$_2$CO$_2$H,
(b) CH$_2$CO$_2$C$_{1-4}$alkyl,
(c) CH$_2$SC$_{1-4}$alkyl and
(d) CH$_2$S(O)$_2$C$_{1-4}$alkyl;
R$^3$ is selected from the group consisting of:
(a) H,
(b) CH$_3$,
(c) CH(CH$_3$)$_2$,
(d) CH$_2$CH(CH$_3$)$_2$,
(e) CH$_2$Ph,
(f) CH$_2$PHOH,

74

(g) CH$_2$OH,
(h) CH$_2$SH,
(i) CH$_2$CH$_2$SCH$_3$,
(j) CH(CH$_3$)CH$_2$CH$_3$,
(k) CH(CH$_3$)OH,
(l) CH$_2$COOH,
(m) CH$_2$CH$_2$ COOH,
(n) CH$_2$CH$_2$CH$_2$NHCNH(NH$_2$),
(o) CH$_2$CH$_2$CH$_2$CH$_2$NH$_2$,
(p) CH$_2$C(O)NH$_2$,
(q) CH$_2$CH$_2$C(O)NH$_2$,
(r) CH$_2$CH$_2$CO$_2$C$_{1-4}$alkyl,
(s) CH$_2$CH$_2$S(O)$_2$C$_{1-4}$alkyl,

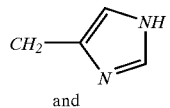

(t)

and

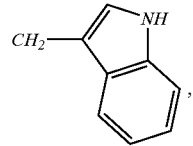

(u)

, or R$^3$ and X$^3$ together form a saturated monocyclic ring having the following structure:

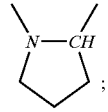

;

R$^4$ is selected from the group consisting of:
(a) H,
(b) CH$_3$,
(c) CH(CH$_3$)$_2$,
(d) CH$_2$CH(CH$_3$)$_2$,
(e) CH$_2$Ph
(t) CH$_2$PhOH,
(g) CH$_2$OH,
(h) CH$_2$SH
(i) CH$_2$CH$_2$SCH$_3$,
(j) CH(CH$_3$)CH$_2$CH$_3$,
(k) CH(CH$_3$)OH,
(l) CH$_2$COOH,
(m) CH$_2$CH$_2$COOH,
(n) CH$_2$CH$_2$CH$_2$NHCNH(NH$_2$),
(o) CH$_2$CH$_2$CH$_2$CH$_2$NH$_2$,
(p) CH$_2$C(O)NH$_2$,
(q) CH$_2$CH$_2$C(O)NH$_2$,

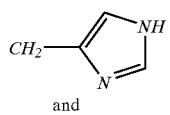

(r)

and

-continued

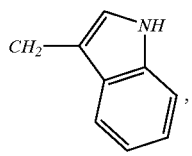
(s)

or $R^4$ and $X^4$ together form a saturated monocyclic ring having the following structure:

$R^5$ is selected from the group consisting of:
(a) $C_{1-6}$alkyl,
(b) aryl$C_{1-8}$alkyl wherein the aryl is selected from the group consisting of:
 (1) phenyl,
 (2) naphthyl,
 (3) pyridyl,
 (4) furyl,
 (5) thienyl,
 (6) thiazolyl,
 (7) isothiazolyl,
 (8) imidazolyl,
 (9) benzimidazolyl,
 (10) pyrazinyl,
 (11) pyrimidyl,
 (12) quinolyl,
 (13) isoquinolyl,
 (14) benzofuryl,
 (15) benzothienyl,
 (16) pyrazolyl,
 (17) indolyl,
 (18) purinyl,
 (19) isoxazolyl,
 (20) oxazolyl and
 (21) coumarinyl, and
  the aryl may be optionally mono- or di-substituted with a substituent independently selected from:
 (1) halo,
 (2) amino,
 (3) nitro,
 (4) hydroxy,
 (5) cyano,
 (6) carboxy,
 (7) formyl,
 (8) amino carbonyl,
 (9) $C_{1-6}$alkyl,
 (10) $C_{1-6}$fluoroalkyl,
 (11) $C_{1-6}$alkylcarbonyl,
 (12) $C_{1-6}$alkoxycarbonyl,
 (13) $C_{1-6}$alkoxy,
 (14) $C_{1-6}$alkylthio and
 (15) $C_{1-6}$alkylsulfonyl;
$R^6$ and $R^7$ are independently selected from the group consisting of:
(a) $C_{1-4}$alkyl,
(b) $C_{1-4}$fluoroalkyl and
(c) benzyl or mono- or disubstituted benzyl wherein the substituent is selected from the group consisting of:
 (1) methyl,
 (2) halogen,
 (3) methoxy and
 (4) cyano,
or $R^6$ and $R^7$ may be joined to form a pyrrolidine, piperidine, morpholine, thiamorpholine or N—$R^8$ substituted piperazine wherein $R^8$ is H or $C_{1-3}$alkyl; and
$X^2$, $X^3$ and $X^4$ are independently H, or
$X^3$ and $R^3$, or $X^4$ and $R^4$ may together form a saturated monocyclic ring having the following structure:

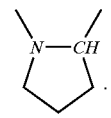

2. A compound according to claim 1 which is (SEQ ID NO 16)

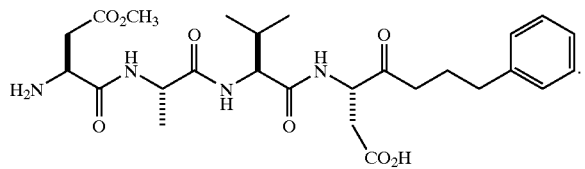

3. A pharmaceutical composition comprising a compound as defined in claim 1 in combination with a carrier.

4. A compound of formula I

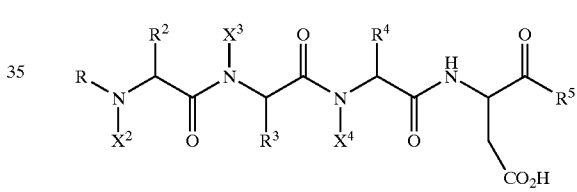
I or a salt thereof, wherein:
R is selected from the group consisting of:
(a) H and
(b) C(O)$R^1$;
$R^1$ is selected from the group consisting of:
(a) hydrogen,
(b) $C_{1-6}$alkoxy,
(c) N$R^6R^7$,
(d) benzyloxy or mono- or disubstituted benzyloxy, wherein the substituent is selected from the group consisting of:
 (1) methyl,
 (2) halogen,
 (3) methoxy and
 (4) cyano,
(e) $C_{1-6}$alkyl or substituted $C_{1-6}$alkyl, wherein the substituent is selected from the group consisting of:
 (1) hydroxy,
 (2) halo,
 (3) $C_{1-3}$alkoxy,
 (4) $C_{1-3}$alkylthio,
 (5) phenyl $C_{1-3}$alkoxy,
 (6) phenyl $C_{1-3}$alkylthio,
 (7) phenylcarboxy and
 (8) carboxy,
(f) aryl or aryl$C_{1-6}$alkyl wherein the aryl group is selected from the group consisting of:

(1) phenyl,
(2) naphthyl,
(3) pyridyl,
(4) furyl,
(5) thienyl,
(6) thiazolyl,
(7) isothiazolyl,
(8) imidazolyl,
(9) benzimidazolyl,
(10) pyrazinyl,
(11) pyrimidyl,
(12) quinolyl,
(13) isoquinolyl,
(14) benzofuryl,
(15) benzothienyl,
(16) pyrazolyl,
(17) indolyl,
(18) purinyl,
(19) isoxazolyl and
(20) oxazolyl, and (g) mono and di-substituted aryl as defined above in items (1) to (20) of (f), wherein the substituents are independently selected from:
(1) halo,
(2) amino,
(3) nitro,
(4) hydroxy,
(5) cyano,
(6) carboxy,
(7) formyl,
(8) amino carbonyl,
(9) $C_{1-6}$alkyl,
(10) $C_{1-6}$fluoroalkyl,
(11) $C_{1-6}$alkylcarbonyl,
(12) $C_{1-6}$alkoxycarbonyl,
(13) $C_{1-6}$alkoxy,
(14) $C_{1-6}$alkylthio,
(15) $C_{1-6}$alkylsulfonyl and
(16) deuterio;

$R^2$ is selected from the group consisting of:
(a) H,
(b) $CH_3$,
(c) $CH(CH_3)_2$,
(d) $CH_2CH(CH_3)_2$,
(e) $CH_2Ph$,
(f) $CH_2OH$,
(g) $CH_2SH$,
(h) $CH_2CH_2SCH_3$,
(i) $CH(CH_3)CH_2CH_3$,
(j) $CH(CH_3)OH$,
(k) $CH_2COOH$,
(l) $CH_2CH_2COOH$,
(m) $CH_2CH_2CH_2NHCNH(NH_2)$,
(n) $CH_2CH_2CH_2CH_2NH_2$,
(o) $CH_2C(O)NH_2$,
(p) $CH_2CH_2C(O)NH_2$,
(q) $CH_2CO_2C_{1-4}$alkyl,
(r) $CH_2SC_{1-4}$alkyl,
(s) $CH_2S(O)_2C_{1-4}$alkyl,

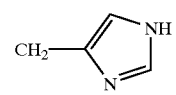

and (t)

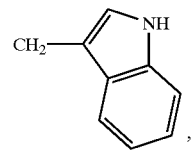

, or $R^2$ and $X^2$ together form a saturated monocyclic ring having the following structure:

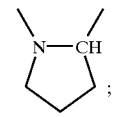

;

$R^3$ is selected from the group consisting of:
(a) $CH_3$,
(b) $CH_2CH_2CO_2H$,
(c) $CH_2CH_2CO_2C_{1-4}$alkyl and
(d) $CH_2CH_2S(O)_2C_{1-4}$alkyl;

$R^4$ is selected from the group consisting of:
(a) H,
(b) $CH_3$,
(c) $CH(CH_3)_2$,
(d) $CH_2CH(CH_3)_2$,
(e) $CH_2Ph$,
(f) $CH_2PhOH$,
(g) $CH_2OH$,
(h) $CH_2SH$,
(i) $CH_2CH_2SCH_3$,
(j) $CH(CH_3)CH_2CH_3$,
(k) $CH(CH_3)OH$,
(l) $CH_2COOH$,
(m) $CH_2CH_2COOH$,
(n) $CH_2CH_2CH_2NHCNH(NH_2)$,
(o) $CH_2CH_2CH_2CH_2NH_2$,
(p) $CH_2C(O)NH_2$,
(q) $CH_2CH_2C(O)NH_2$,

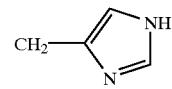

and (r)

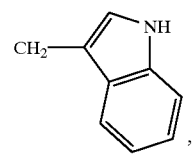

, (s)

or $R^4$ and $X^4$ together form a saturated monocyclic ring having the following structure:

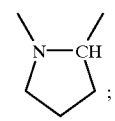

;

$R^5$ is selected from the group consisting of:
(a) $C_{1-6}$alkyl,
(b) aryl$C_{1-8}$alkyl wherein the aryl is selected from the group consisting of:

(1) phenyl,
(2) naphthyl,
(3) pyridyl,
(4) furyl,
(5) thienyl,
(6) thiazolyl,
(7) isothiazolyl,
(8) imidazolyl,
(9) benzimidazolyl,
(10) pyrazinyl,
(11) pyrimidyl,
(12) quinolyl,
(13) isoquinolyl,
(14) benzofuryl,
(15) benzothienyl,
(16) pyrazolyl,
(17) indolyl,
(18) purinyl,
(19) isoxazolyl,
(20) oxazolyl and
(21) coumarinyl, and
   the aryl may be optionally mono- or di-substituted with a substituent independently selected from:
(1) halo,
(2) amino,
(3) nitro,
(4) hydroxy,
(5) cyano,
(6) carboxy,
(7) formyl,
(8) amino carbonyl,
(9) $C_{1-6}$alkyl,
(10) $C_{1-6}$fluoroalkyl,
(11) $C_{1-6}$alkylcarbonyl,
(12) $C_{1-6}$alkoxycarbonyl,
(13) $C_{1-6}$alkoxy,
(14) $C_{1-6}$alkylthio and
(15) $C_{1-6}$alkylsulfonyl;

$R^6$ and $R^7$ are independently selected from the group consisting of:
(a) $C_{1-4}$alkyl,
(b) $C_{1-4}$fluoroalkyl and
(c) benzyl or mono- or disubstituted benzyl wherein the substituent is selected from the group consisting of:
(1) methyl,
(2) halogen,
(3) methoxy and
(4) cyano, or $R^6$ and $R^7$ may be joined to form a pyrrolidine, piperidine, morpholine, thiamorpholine or N—$R^8$ substituted piperazine wherein $R^8$ is H or $C_{1-3}$alkyl; and $X^2$, $X^3$ and $X^4$ are independently H, or $X^2$ and $R^2$, or $X^4$ and $R^4$ may together form a saturated monocyclic ring having the following structure:

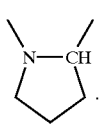

5. A pharmaceutical composition comprising a compound as defined in claim 4 in combination with a carrier.

6. A compound of formula I

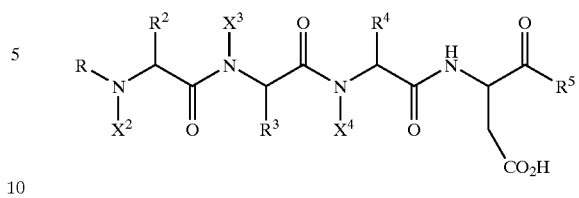

or a salt thereof, wherein:

R is selected from the group consisting of:
(a) H and
(b) $C(O)R^1$;

$R^1$ is selected from the group consisting of:
(a) hydrogen,
(b) $C_{1-6}$alkoxy,
(c) $NR^6R^7$,
(d) benzyloxy or mono- or disubstituted benzyloxy, wherein the substituent is selected from the group consisting of:
(1) methyl,
(2) halogen,
(3) methoxy and
(4) cyano,
(e) $C_{1-6}$alkyl or substituted $C_{1-6}$alkyl, wherein the substituent is selected from the group consisting of:
(1) hydroxy,
(2) halo,
(3) $C_{1-3}$alkoxy,
(4) $C_{1-3}$alkylthio,
(5) phenyl $C_{1-3}$alkoxy,
(6) phenyl $C_{1-3}$alkylthio,
(7) phenylcarboxy and
(8) carboxy,
(f) aryl or aryl$C_{1-6}$alkyl wherein the aryl group is selected from the group consisting of:
(1) phenyl,
(2) naphthyl,
(3) pyridyl,
(4) furyl,
(5) thienyl,
(6) thiazolyl,
(7) isothiazolyl,
(8) imidazolyl,
(9) benzimidazolyl,
(10) pyrazinyl,
(11) pyrimidyl,
(12) quinolyl,
(13) isoquinolyl,
(14) benzofuryl,
(15) benzothienyl,
(16) pyrazolyl,
(17) indolyl,
(18) purinyl,
(19) isoxazolyl and
(20) oxazolyl, and
(g) mono and di-substituted aryl as defined above in items (1) to (20) of (f), wherein the substituents are independently selected from:
(1) halo,
(2) amino,
(3) nitro,
(4) hydroxy,
(5) cyano,
(6) carboxy, (7) formyl,
(8) amino carbonyl,
(9) $C_{1-6}$alkyl,
(10) $C_{1-6}$fluoroalkyl,
(11) $C_{1-6}$alkylcarbonyl,
(12) $C_{1-6}$alkoxycarbonyl,
(13) $C_{1-6}$alkoxy,
(14) $C_{1-6}$alkylthio,
(15) $C_{1-6}$alkylsulfonyl and
(16) deuterio;

$R^2$ is selected from the group consisting of:
(a) H,
(b) $CH_3$,
(c) $CH(CH_3)_2$,
(d) $CH_2CH(CH_3)_2$,
(e) $CH_2Ph$,
(f) $CH_2OH$,
(g) $CH_2SH$,
(h) $CH_2CH_2SCH_3$,
(i) $CH(CH_3)CH_2CH_3$,
(j) $CH(CH_3)OH$,
(k) $CH_2COOH$,
(l) $CH_2CH_2COOH$,
(m) $CH_2CH_2CH_2NHCNH(NH_2)$,
(n) $CH_2CH_2CH_2CH_2NH_2$,
(o) $CH_2C(O)NH_2$,
(p) $CH_2CH_2C(O)NH_2$,
(q) $CH_2CO_2C_{1-4}$alkyl,
(r) $CH_2SC_{1-4}$alkyl,
(s) $CH_2S(O)_2C_{1-4}$alkyl,

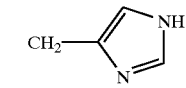
and

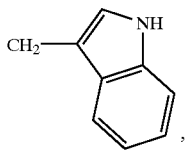
, or $R^2$ and $X^2$ together form a saturated monocyclic ring having the following structure:

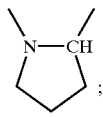
;

$R^3$ is selected from the group consisting of:
(a) H,
(b) $CH_3$,
(c) $CH(CH_3)_2$,
(d) $CH_2CH(CH_3)_2$,
(e) $CH_2Ph$,
(f) $CH_2PhOH$,
(g) $CH_2OH$,
(h) $CH_2SH$,
(i) $CH_2CH_2SCH_3$,
(j) $CH(CH_3)CH_2CH_3$,
(k) $CH(CH_3)OH$,
(l) $CH_2COOH$,
(m) $CH_2CH_2COOH$,
(n) $CH_2CH_2CH_2NHCNH(NH_2)$,
(o) $CH_2CH_2CH_2CH_2NH_2$,
(p) $CH_2C(O)NH_2$,
(q) $CH_2CH_2C(O)NH_2$,
(r) $CH_2CH_2CO_2C_{1-4}$alkyl,
(s) $CH_2CH_2S(O)_2C_{1-4}$alkyl,

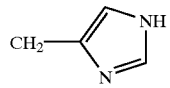
and

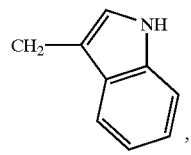
, or $R^3$ and $X^3$ together form a saturated monocyclic ring having the following structure:

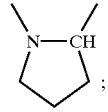
;

$R^4$ is isopropyl;
$R^5$ is selected from the group consisting of:
(a) $C_{1-6}$alkyl,
(b) aryl$C_{1-8}$alkyl wherein the aryl is selected from the group consisting of:
(1) phenyl,
(2) naphthyl,
(3) pyridyl,
(4) furyl,
(5) thienyl,
(6) thiazolyl,
(7) isothiazolyl,
(8) imidazolyl,
(9) benzimidazolyl,
(10) pyrazinyl,
(11) pyrimidyl,
(12) quinolyl,
(13) isoquinolyl,
(14) benzofuryl,
(15) benzothienyl,
(16) pyrazolyl,
(17) indolyl,
(18) purinyl,
(19) isoxazolyl,
(20) oxazolyl and
(21) coumarinyl and
(c) aryl as defined above in items (1) to (21) of (b), wherein the aryl portions may be optionally mono- or di-substituted with a substituent independently selected from:
(1) halo,
(2) amino,
(3) nitro,
(4) hydroxy,
(5) cyano,
(6) carboxy,
(7) formyl,
(8) amino carbonyl, (9) $C_{1-6}$alkyl,
(10) $C_{1-6}$fluoroalkyl,
(11) $C_{1-6}$alkylcarbonyl,
(12) $C_{1-6}$alkoxycarbonyl,
(13) $C_{1-6}$alkoxy,
(14) $C_{1-6}$alkylthio and
(15) $C_{1-6}$alkylsulfonyl;

$R^6$ and $R^7$ are independently selected from the group consisting of:
(a) $C_{1-4}$alkyl,
(b) $C_{1-4}$fluoroalkyl and
(c) benzyl or mono- or disubstituted benzyl wherein the substituent is selected from the group consisting of:
(1) methyl,
(2) halogen,
(3) methoxy and
(4) cyano, or $R^6$ and $R^7$ may be joined to form a pyrrolidine, piperidine, morpholine, thiamorpholine or N—$R^8$ substituted piperazine wherein $R^8$ is H or $C_{1-3}$alkyl; and $X^2$, $X^3$ and $X^4$ are independently H, or $X^2$ and $R^2$, or $X^3$ and $R^3$ may together form a saturated monocyclic ring having the following structure:

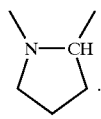

7. A pharmaceutical composition comprising a compound as defined in claim 6 in combination with a carrier.

8. A compound of formula II

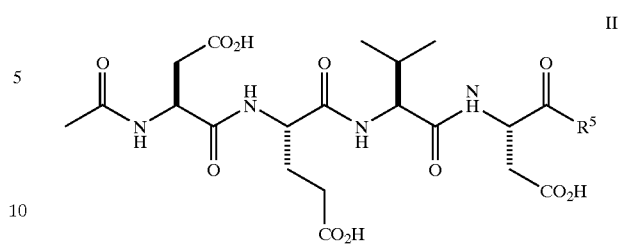

or a salt thereof, wherein:
$R^5$ is selected from the group consisting of:
(a) $C_{1-6}$alkyl and
(b) aryl$C_{1-8}$alkyl wherein the aryl is selected from the group consisting of:
(1) phenyl,
(2) naphthyl,
(3) pyridyl and
(4) coumarinyl,
and the aryl may be optionally mono- or di-substituted with a substituent independently selected from:
(1) halo,
(2) hydroxy,
(3) cyano,
(4) carboxy,
(5) amino carbonyl,
(6) $C_{1-3}$alkyl,
(7) $C_{1-3}$fluoroalkyl,
(8) $C_{1-3}$alkylcarbonyl,
(9) $C_{1-3}$alkoxycarbonyl,
(10) $C_{1-3}$alkoxy,
(11) $C_{1-3}$alkylthio and
(12) $C_{1-3}$alkylsulfonyl.

9. A compound according to claim 8 wherein $R^5$ is selected from the group consisting of:
(a) methyl,
(b) propyl,
(c) phenyl$C_{1-5}$alkyl,
(d) 4-methoxyphenylpropyl and
(e) napthylpropyl.

10. A compound according to claim 9 selected from the following group:

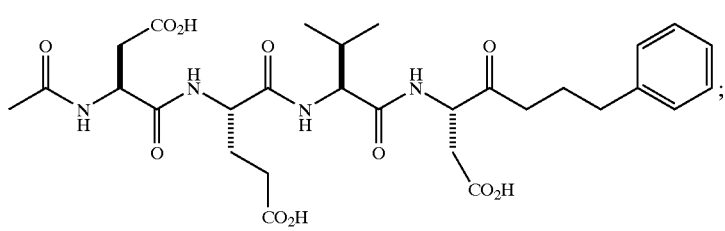

(SEQ ID NO1)

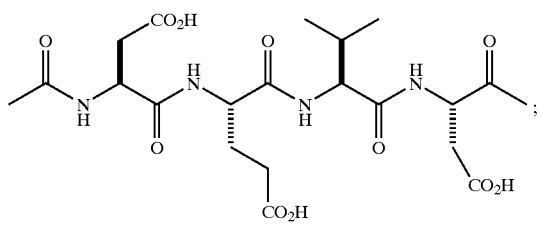

(SEQ ID NO 2)

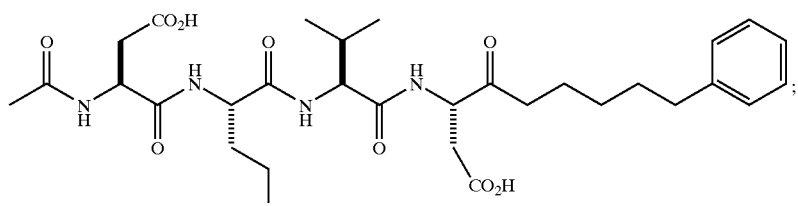
(SEQ ID NO 3)
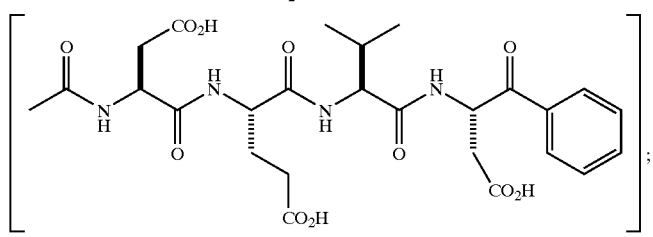
(SEQ ID NO 5)
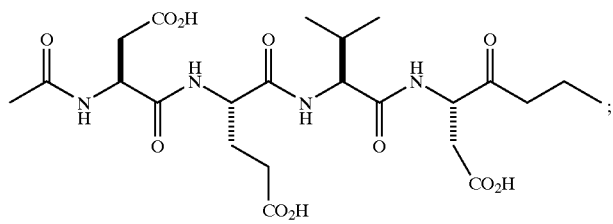
(SEQ ID NO 6)
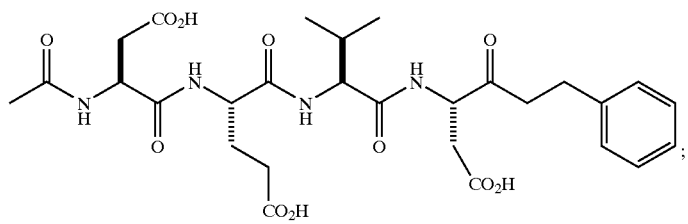
(SEQ ID NO 7)
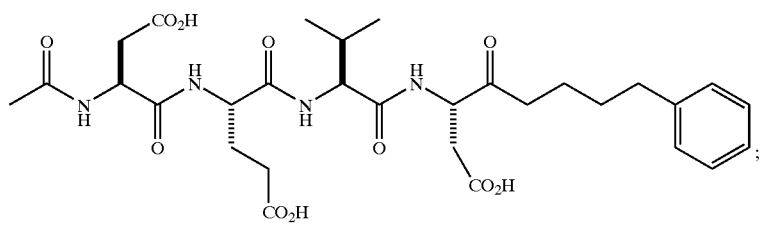
(SEQ ID NO 8)
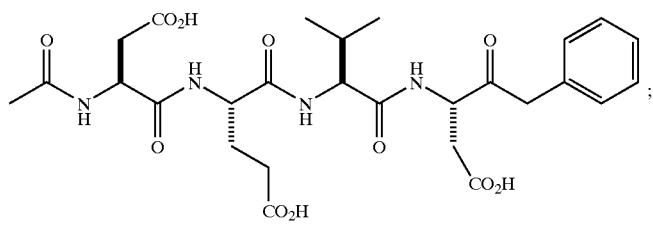
(SEQ ID NO 9)
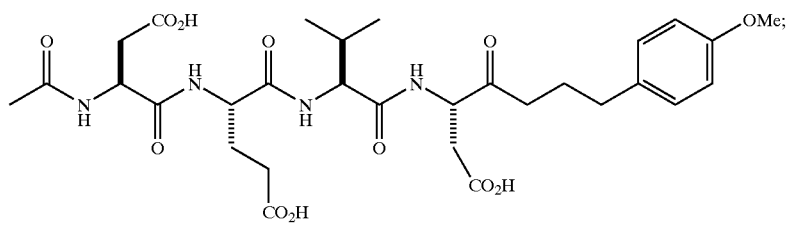
and (SEQ ID NO 10)

[Structure of Ac-Asp-Glu-Val-Asp(CO-CH2CH2-naphthyl) peptide]

[Structure of Ac-Asp-Glu-Val-Asp-NH-coumarin peptide]

11. A pharmaceutical composition comprising a compound as defined in claim 8 in combination with a carrier.

12. A compound of formula III

III

[Structure of formula III showing R1-NH-Asp(CO2H)-Ala-Val-Asp(CO2H)-R5 tetrapeptide]

or a salt thereof, wherein:
R$^1$ is selected from the group consisting of:
  (a) $C_{1-6}$alkyl or substituted $C_{1-6}$alkyl, wherein the substituent is selected from the group consisting of:
    (1) hydroxy,
    (2) halo,
    (3) $C_{1-3}$alkoxy,
    (4) $C_{1-3}$alkylthio,
    (5) phenyl$C_{1-3}$alkoxy,
    (6) phenyl$C_{1-3}$alkylthio,
    (7) phenylcarboxy and
    (8) carboxy,
  (b) aryl or aryl$C_{1-6}$alkyl wherein the aryl group is selected from the group consisting of:
    (1) phenyl and
    (2) naphthyl, and
  (c) mono and di-substituted aryl as defined above in items (1) to (2) wherein the substituents are independently selected from:
    (1) halo,
    (2) hydroxy,
    (3) cyano,
    (4) carboxy,
    (5) amino carbonyl,
    (6) $C_{1-3}$alkyl,
    (7) $C_{1-3}$fluoroalkyl,
    (8) $C_{1-3}$alkylcarbonyl,
    (9) $C_{1-3}$alkoxycarbonyl,
    (10) $C_{1-3}$alkoxy,
    (11) $C_{1-3}$alkylthio,
    (12) $C_{1-3}$alkylsulfonyl and
    (13) deuterio; and R$^5$ is aryl$C_{1-8}$alkyl wherein aryl is selected from the group consisting of phenyl, naphthyl, pyridyl, and mono-, or di-substituted derivatives thereof, wherein the substituents are individually selected from the group consisting of:
  (1) halo,
  (2) hydroxy,
  (3) cyano,
  (4) carboxy,
  (5) amino carbonyl,
  (6) $C_{1-3}$alkyl,
  (7) $C_{1-3}$fluoroalkyl,
  (8) $C_{1-3}$alkylcarbonyl,
  (9) $C_{1-3}$alkoxycarbonyl,
  (10) $C_{1-3}$alkoxy,
  (11) $C_{1-3}$alkylthio and
  (12) $C_{1-3}$alkylsulfonyl.

13. A compound according to claim 12 wherein:
R1 is selected from the group consisting of:
  (a) methyl,
  (b) phenyl and
  (c) mono- or disubstituted phenyl, wherein the substituents are selected from the group consisting of:
    (1) halo and
    (2) deuterio; and R5 is aryl$C_{3-5}$alkyl wherein aryl is selected from the group consisting of phenyl and naphthyl.

14. A compound according to claim 13 selected from the following group:

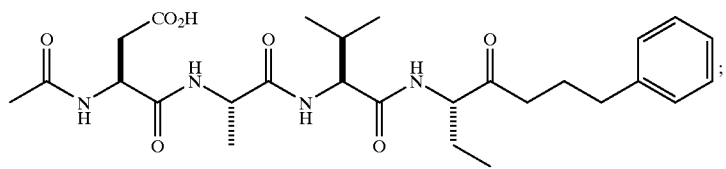
(SEQ ID NO 12)
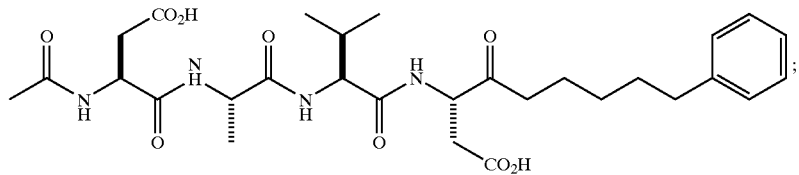
(SEQ ID NO 13)
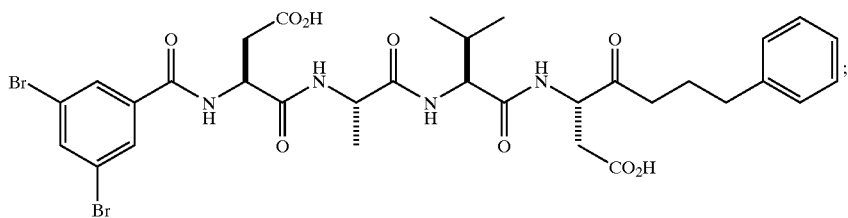
(SEQ ID NO 14)
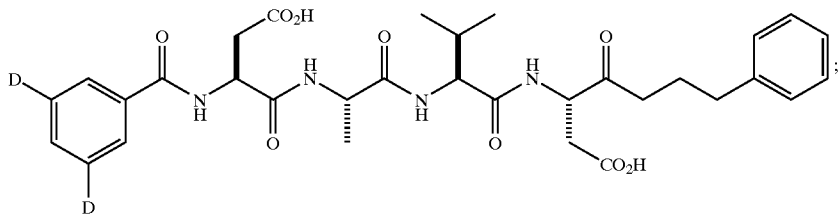
(SEQ ID NO 15)
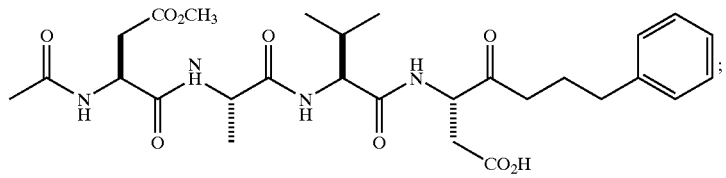
(SEQ ID NO 26)
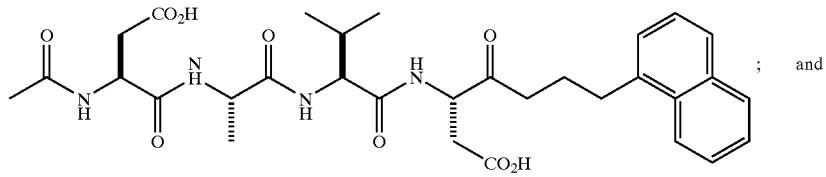
(SEQ ID NO 17) ; and
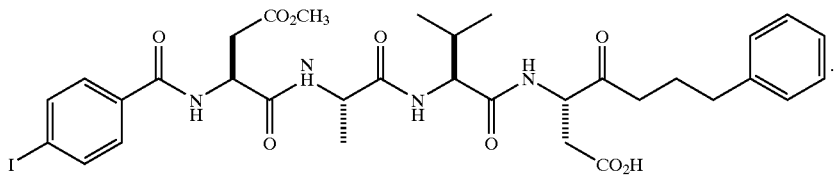
(SEQ ID NO 18) .

15. A pharmaceutical composition comprising a compound as defined in claim 12 in combination with a carrier.

16. A compound of formula IV

*[Structure of formula IV shown]* or a salt thereof, wherein:

$R^9$ is selected from the group consisting of:
(a) $CO_2H$,
(b) $CO_2C_{1-4}$alkyl,
(c) $SC_{1-4}$alkyl and
(d) $S(O)_2C_{1-4}$alkyl;

$R^{10}$ is selected from the group consisting of:
(a) H,
(b) $CH_2CO_2H$,
(c) $CH_2CO_2C_{1-4}$alkyl and
(d) $CH_2S(O)_2C_{1-4}$alkyl; and Ar is selected from the group consisting of:
(a) phenyl and
(b) napthyl.

17. A compound according to claim 16 wherein:

$R^9$ is selected from the group consisting of:
(a) $CO_2H$,
(b) $SCH_3$ and
(c) $S(O)_2CH_3$; and $R^{10}$ is selected from the group consisting of:
(a) H and
(d) $CH_2S(O)_2CH_3$.

18. A compound according to claim 17 selected from the following group:

(SEQ ID NO 19)
*[Structure shown]*

(SEQ ID NO 20)
*[Structure shown]*

(SEQ ID NO 21)
*[Structure shown]*

(SEQ ID NO 22)
*[Structure shown]* and (SEQ ID NO 23)
*[Structure shown]*

19. A pharmaceutical composition comprising a compound as defined in claim 16 in combination with a carrier.

20. A compound selected from the following group:

(a) (3S)-3-((2S )-2-[((2S)-2-[(2S)-2-(Acetylamino)-3-carboxypropanoyl]amino-4-carboxybutanoyl)amino]-3-methylbutanoylamino)-4-oxo-7-phenylheptanoic acid (SEQ ID NO 1);

(b) (4S)-4-[(2S)-2-(Acetylamino)-3-carboxypropanoyl]amino-5-[(1S)-1-([(1S)-1-(carboxymethyl)-2-oxopropyl]aminocarbonyl)-2-methylpropyl]amino-5-oxopentanoic acid (SEQ ID NO 2);

(c) (3S)-3-((2S)-2-[((2S)-2-[(2S)-2-(Acetylamino)-3-carboxypropanoyl]amino-4-carboxybutanoyl)amino]-3-methylbutanoylamino)-4-oxo-9-phenylnonanoic acid (SEQ ID NO 3);

(d) (3S)-3-((2S)-2-[((2S)-2-[(2S)-2-(Acetylamino)-3-carboxypropanoyl]amino-4-carboxybutanoyl)amino]-3-methylbutanoylamino)-4-oxoheptanoic acid (SEQ ID NO 5);

(e) (3S)-3-((2S)-2-[((2S)-2-[(2S)-2-(Acetylamino)-3-carboxypropanoyl]amino-4-carboxybutanoyl)amino]-3-methylbutanoylamino)-4-oxo-6-phenylhexanoic acid (SEQ ID NO 6);

(f) (3S)-3-((2S)-2-[((2S)-2-[(2S)-2-(Acetylamino)-3-carboxypropanoyl]amino-4-carboxybutanoyl)amino]-3-methylbutanoylamino)-4-oxo-8-phenyloctanoic acid (SEQ ID NO 7);

(g) (3S)-3-((2S)-2-[((2S)-2-[(2S)-2-(Acetylamino)-3-carboxypropanoyl]amino-4-carboxybutanoyl)amino]-3-methylbutanoylamino)-4-oxo-5-phenylpentanoic acid (SEQ ID NO 8);

(h) (3S)-3-((2S)-2-[((2S)-2-[(2S)-2-(Acetylamino)-3-carboxypropanoyl]amino-4-carboxybutanoyl)amino]-3-methylbutanoylamino)-7-(4-methoxyphenyl)-4-oxoheptanoic acid (SEQ ID NO 9);

(i) (3S)-3-((2S)-2-[((2S)-2-[(2S)-2-(Acetylamino)-3-carboxypropanoyl]amino-4-carboxybutanoyl)amino]-3-methylbutanoylamino)-7-(1-naphthyl)-4-oxoheptanoic acid (SEQ ID NO 10);

(j) (3S)-3-((2S)-2-[((2S)-2-[(2S)-2-(Acetylamino)-3-carboxypropanoyl]aminopropanoyl)amino]-3-methylbutanoylamino)-4-oxo-7-phenylheptanoic acid (SEQ ID NO 12);

(k) (3S)-3-((2S)-2-[((2S)-2-[(2S)-2-(Acetylamino)-3-carboxypropanoyl]aminopropanoyl)amino]-3-methylbutanoylamino)-4-oxo-9-phenylnonanoic acid (SEQ ID NO 13);

(l) (3S)-3-[((2S)-2-[(2S)-2-((2S)-3-Carboxy-2-[(3,5-dibromobenzoyl)amino]propanoylamino)propanoyl]

amino-3-methylbutanoyl)amino]-4-oxo-7-phenylheptanoic acid (SEQ ID NO 14);

(m) (3S)-3-[((2S)-2-[(2S)-2-((2S)-3-Carboxy-2-[(3,5-dideuteriobenzoyl)amino]propanoylamino)propanoyl] amino-3-methylbutanoyl)amino]-4-oxo-7-phenylheptanoic-acid (SEQ ID NO 15);

(n) (3S)-3-((2S)-2-[((2S)-2-[(2S)-2-Amino-4-methoxy-4-oxobutanoyl]aminopropanoyl)amino]-3-methylbutanoylamino)-4-oxo-7-phenylheptanoic acid (SEQ ID NO 16);

(o) (3S)-3-((2S)-2-[((2S)-2-[(2S)-2-(Acetylamino)-4-methoxy-4-oxobutanoyl]aminopropanoyl)amino]-3-methylbutanoylamino)-4-oxo-7-phenylheptanoic acid (SEQ ID NO 26);

(p) (3S)-3-((2S)-2-[((2S)-2-[(2S)-2-(Acetylamino)-3-carboxypropanoyl]aminopropanoyl)amino]-3-methylbutanoylamino)-7-(1-naphthyl)-4-oxoheptanoic acid (SEQ ID NO 17);

(q) (3S)-3-[((2S)-2-[(2S)-2-((2S)-3-Carboxy-2-[(4-iodobenzoyl)amino]propanoylamino)propanoyl]amino-3-methylbutanoyl)amino]-4-oxo-7-phenylheptanoic acid (SEQ ID NO 18);

(r) (3S)-3-[((2S)-2-[(2S)-2-[(2S)-2-(Acetylamino)-3-carboxypropanoyl]amino-4-(methylsulfonyl)butanoyl] amino-3-methylbutanoyl)amino]-4-oxo-7-phenylheptanoic acid (SEQ ID NO 19);

(s) (3S)-3-((2S)-2-[((2S)-2-[(2R)-2-(Acetylamino)-3-(methylsulfanyl)propanoyl]aminopropanoyl)amino]-3-methylbutanoylamino)-4-oxo-7-phenylheptanoic acid (SEQ ID NO 20);

(t) (3S)-3-((2S)-2-[((2S)-2-[(2R)-2-(Acetylamino)-3-(methylsulfonyl)propanoyl]aminopropanoyl)amino]-3-methylbutanoylamino)-4-oxo-7-phenylheptanoic acid (SEQ ID NO 21);

(u) (3S)-3-((2S)-2-[((2S)-2-[(2R)-2-(Acetylamino)-3-(methylsulfanyl)propanoyl]aminopropanoyl)amino]-3-methylbutanoylamino)-7-(1-naphthyl)-4-oxoheptanoic acid (SEQ ID NO 22); and (v) (3S)-3-((2S)-2-[((2S)-2-[(2R)-2-(Acetylamino)-3-(methylsulfonyl)propanoyl]aminopropanoyl)amino]-3-methylbutanoylamino)-7-(1-naphthyl)-4-oxoheptanoic acid (SEQ ID NO 23).

21. A method of inhibiting caspase-3 in a mammal in need thereof comprising administering to said mammal a compound according to claim 1 for a time and under conditions effective to inhibit caspase-3.

22. A method of inhibiting caspase-3 in a mammal in need thereof comprising administering to said mammal a compound according to claim 4 for a time and under conditions effective to inhibit caspase-3.

23. A method of inhibiting caspase-3 in a mammal in need thereof comprising administering to said mammal a compound according to claim 6 for a time and under conditions effective to inhibit caspase-3.

24. A method of inhibiting caspase-3 in a mammal in need thereof comprising administering to said mammal a compound according to claim 8 for a time and under conditions effective to inhibit caspase-3.

25. A method of inhibiting caspase-3 in a mammal in need thereof comprising administering to said mammal a compound according to claim 12 for a time and under conditions effective to inhibit caspase-3.

26. A method of inhibiting caspase-3 in a mammal in need thereof comprising administering to said mammal a compound according to claim 16 for a time and under conditions effective to inhibit caspase-3.

* * * * *

SEQUENCE LISTING

```
<160> NUMBER OF SEQ ID NOS:  25

<210> SEQ ID NO 1
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: 3-phenylpropyl replaces hydroxy at the carboxy
      terminus

<400> SEQUENCE: 1

Asp Glu Val Asp
 1

<210> SEQ ID NO 2
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
```

```
<221> NAME/KEY: MOD_RES
<222> LOCATION: 4
<223> OTHER INFORMATION: Methyl replaces hydroxy at the carboxy terminus

<400> SEQUENCE: 2

Asp Glu Val Asp
 1

<210> SEQ ID NO 3
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: 5-phenylpentyl replaces hydroxy at the carboxy
      terminus

<400> SEQUENCE: 3

Asp Glu Val Asp
 1

<210> SEQ ID NO 4
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: Phenyl replaces hydroxy at the carboxy terminus

<400> SEQUENCE: 4

Asp Glu Val Asp
 1

<210> SEQ ID NO 5
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: Propyl replaces hydroxy at the carboxy terminus

<400> SEQUENCE: 5

Asp Glu Val Asp
 1

<210> SEQ ID NO 6
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: 2-phenylethyl replaces hydroxy at the carboxy
      terminus

<400> SEQUENCE: 6
```

Asp Glu Val Asp
1

<210> SEQ ID NO 7
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: 4-phenylbutyl replaces hydroxy at the carboxy
      terminus

<400> SEQUENCE: 7

Asp Glu Val Asp
1

<210> SEQ ID NO 8
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: Benzyl replaces hydroxy at the carboxy terminus

<400> SEQUENCE: 8

Asp Glu Val Asp
1

<210> SEQ ID NO 9
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: 3-(4-methoxyphenyl)propyl replaces hydroxy at
      the carboxy terminus

<400> SEQUENCE: 9

Asp Glu Val Asp
1

<210> SEQ ID NO 10
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: 3-(1-naphthyl)propyl replaces hydroxy at the
      carboxy terminus

<400> SEQUENCE: 10

Asp Glu Val Asp
1

```
<210> SEQ ID NO 11
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: 4-methylcoumarin-7-ylamino replaces hydroxy at
      the carboxy terminus

<400> SEQUENCE: 11

Asp Glu Val Asp
 1

<210> SEQ ID NO 12
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: 3-phenylpropyl replaces hydroxy at the carboxy
      terminus

<400> SEQUENCE: 12

Asp Ala Val Asp
 1

<210> SEQ ID NO 13
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: 5-phenylpentyl replaces hydroxy at the carboxy
      terminus

<400> SEQUENCE: 13

Asp Ala Val Asp
 1

<210> SEQ ID NO 14
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: MOD_RES
<222> LOCATION: 1
<223> OTHER INFORMATION: 3,5-dibromobenzoyl replaces hydrogen at the
      amino terminus
<221> NAME/KEY: MOD_RES
<222> LOCATION: 4
<223> OTHER INFORMATION: 3-phenylpropyl replaces hydroxy at the carboxy
      terminus

<400> SEQUENCE: 14

Asp Ala Val Asp
 1
```

```
<210> SEQ ID NO 15
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: MOD_RES
<222> LOCATION: 1
<223> OTHER INFORMATION: 3,5-dideuteriobenzoyl replaces hydrogen at the
      amino terminus
<221> NAME/KEY: MOD_RES
<222> LOCATION: 4
<223> OTHER INFORMATION: 3-phenylpropyl replaces hydroxy at the carboxy
      terminus

<400> SEQUENCE: 15

Asp Ala Val Asp
 1

<210> SEQ ID NO 16
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: MOD_RES
<222> LOCATION: 4
<223> OTHER INFORMATION: 3-phenylpropyl replaces hydroxy at the carboxy
      terminus

<400> SEQUENCE: 16

Asp Ala Val Asp
 1

<210> SEQ ID NO 17
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: 3-(1-naphthyl)propyl replaces hydroxy at the
      carboxy terminus

<400> SEQUENCE: 17

Asp Ala Val Asp
 1

<210> SEQ ID NO 18
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: MOD_RES
<222> LOCATION: 1
<223> OTHER INFORMATION: 4-iodobenzoyl replaces hydrogen at the amino
      terminus
<221> NAME/KEY: MOD_RES
<222> LOCATION: 4
<223> OTHER INFORMATION: 3-phenylpropyl replaces hydroxy at the carboxy
      terminus

<400> SEQUENCE: 18

Asp Ala Val Asp
 1

<210> SEQ ID NO 19
```

```
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: VARIANT
<222> LOCATION: 2
<223> OTHER INFORMATION: Xaa is 2-amino-4-(methylsulfonyl)butanoyl
<221> NAME/KEY: MOD_RES
<222> LOCATION: 4
<223> OTHER INFORMATION: 3-phenylpropyl replaces hydroxy at the carboxy
      terminus

<400> SEQUENCE: 19

Asp Xaa Val Asp
 1

<210> SEQ ID NO 20
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: VARIANT
<222> LOCATION: 1
<223> OTHER INFORMATION: Xaa is
      2-(acetylaminio)-3-(methylsulfanyl)propanoyl
<221> NAME/KEY: MOD_RES
<222> LOCATION: 4
<223> OTHER INFORMATION: 3-phenylpropyl replaces hydroxy at the carboxy
      terminus

<400> SEQUENCE: 20

Xaa Ala Val Asp
 1

<210> SEQ ID NO 21
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: VARIANT
<222> LOCATION: 1
<223> OTHER INFORMATION: Xaa is 2-(acetylamino)-3-(methylsulfonyl)
      propanoyl
<221> NAME/KEY: MOD_RES
<222> LOCATION: 4
<223> OTHER INFORMATION: 3-phenylpropyl replaces hydroxy at the carboxy
      terminus

<400> SEQUENCE: 21

Xaa Ala Val Asp
 1

<210> SEQ ID NO 22
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: VARIANT
<222> LOCATION: 1
<223> OTHER INFORMATION: Xaa is 2-(acetylamino)-3-(methylsulfanyl)
      propanoyl
<221> NAME/KEY: MOD_RES
<222> LOCATION: 4
<223> OTHER INFORMATION: 3-(1-naphthyl)propyl replaces hydroxy at the
      carboxy terminus

<400> SEQUENCE: 22
```

```
Xaa Ala Val Asp
1

<210> SEQ ID NO 23
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: VARIANT
<222> LOCATION: 1
<223> OTHER INFORMATION: Xaa is 2-(acetylamino)-3-(methylsufonyl)
      propanoyl
<221> NAME/KEY: MOD_RES
<222> LOCATION: 4
<223> OTHER INFORMATION: 3-(1naphthyl)propyl replaces hydroxy at the
      carboxy terminus

<400> SEQUENCE: 23

Xaa Ala Val Asp
1

<210> SEQ ID NO 24
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: hydrogen replaces hydroxy at the carboxy
      terminus

<400> SEQUENCE: 24

Tyr Val His Asp
1

<210> SEQ ID NO 25
<211> LENGTH: 4
<212> TYPE: PRT
<213> ORGANISM: Artificial Sequence
<220> FEATURE:
<223> OTHER INFORMATION: Completely synthetic amino acid sequence
<221> NAME/KEY: ACETYLATION
<222> LOCATION: 1
<221> NAME/KEY: MOD_RES
<222> LOCATION: 4
<223> OTHER INFORMATION: hydrogen replaces hydroxy a the carboxy
      terminus

<400> SEQUENCE: 25

Asp Glu Val Asp
1
```